(12) United States Patent
Leadlay et al.

(10) Patent No.: US 7,482,137 B2
(45) Date of Patent: Jan. 27, 2009

(54) HYBRID GLYCOSYLATED PRODUCTS AND THEIR PRODUCTION AND USE

(75) Inventors: Peter Francis Leadlay, Cambridge (GB); James Staunton, Cambridge (GB); Sabine Gaisser, Cambridge (GB)

(73) Assignee: Biotica Technology Limited, Essex (GB)

( * ) Notice: Subject to any disclaimer, the term of this patent is extended or adjusted under 35 U.S.C. 154(b) by 0 days.

(21) Appl. No.: 11/580,263

(22) Filed: Oct. 12, 2006

(65) Prior Publication Data

US 2007/0092944 A1    Apr. 26, 2007

Related U.S. Application Data

(63) Continuation of application No. 10/257,549, filed as application No. PCT/GB01/01743 on Apr. 17, 2001, now abandoned, which is a continuation-in-part of application No. 09/694,218, filed on Oct. 23, 2000, now abandoned.

(30) Foreign Application Priority Data

Apr. 13, 2000 (GB) .................................. 0009207.2

(51) Int. Cl.
  C12N 9/10 (2006.01)
  C12N 1/21 (2006.01)
  C07H 21/04 (2006.01)
  C12P 21/06 (2006.01)

(52) U.S. Cl. .................. 435/68.1; 435/75; 435/101; 435/193; 536/23.1

(58) Field of Classification Search ................ 435/68.1, 435/75, 101, 193; 536/23.1
See application file for complete search history.

(56) References Cited

U.S. PATENT DOCUMENTS

| | | | |
|---|---|---|---|
| 3,598,805 | A | 8/1971 | Jones |
| 3,697,547 | A | 10/1972 | Kurath et al. |
| 4,439,426 | A | 3/1984 | Toscano et al. |
| 5,712,146 | A | 1/1998 | Khosla et al. |
| 5,871,983 | A | 2/1999 | Baltz et al. |
| 5,998,194 | A | 12/1999 | Summers, Jr. et al. |

FOREIGN PATENT DOCUMENTS

| | | |
|---|---|---|
| EP | 0098732 | 1/1984 |
| GB | 2256197 | 2/1992 |
| WO | 91/16334 | 10/1991 |
| WO | 93/10248 | 5/1993 |
| WO | 93/13663 | 7/1993 |
| WO | 95/08548 | 3/1995 |
| WO | 96/21038 | 7/1996 |
| WO | 96/40968 | 12/1996 |
| WO | 97/23630 | 7/1997 |
| WO | 98/01546 | 5/1998 |
| WO | 98/49315 | 11/1998 |
| WO | 99/05283 | 2/1999 |
| WO | 99/22722 | 5/1999 |
| WO | 00/00618 | 1/2000 |
| WO | 0004044 | 1/2000 |

OTHER PUBLICATIONS

Gaisser, Sabine, et al., "In vivo Expression of Glycosyltransferases in *Saccharopolyspora erythraea*"; 11th International Symposium on the biology of Actinomycetes, Crete, Greece; Oct. 28, 1999.
Decker, H. et al., Novel Genetically Engineered Tetracenomycins, Angew. Chem. Int. Ed. Engl. (1995) 34:1107-1110.
Gaisser, et al., A defined system for hybrid macrolide biosynthesis in *Saccharopolyspora erythraea*, Molecular Microbiology, 36(2):391-401, (2000).
Cortes et al., An unusually large multifunctional polypeptide in the erythromycin-producing polyketide synthase of *Saccharopolyspora erythraea*, Nature (1990) 348: 176-178.
Donadio et al., Modular Organization of Genes Required for Complex Polyketide Biosynthesis, Science (1991) 252: 675-67.
Donadio et al., An erythrmycin analog produced by reprogramming of polyketide synthesis, PNAS USA (1993) 90:7119-7123.
Hutchinson and Fujii, Polyketide Synthase Gene Manipulation: A Structure-Function Approach Engineering Novel Antibiotics, Ann. Rev. Microbial. (1995) 49:201-238.
Bibb et al., Analysis of the nucleotide sequence of the *Streptomyces glaucescens* tcml genes to provide key information about the enzymology of polyketide antibiotic biosynthesis, EMBO J (1 989) 8:2727-2736.
Sherman et al., Structure and deduced function of the granaticin-producing polyketide synthase gene cluster of *Streptomyces violaceoruber* Tu22, EMBO J (1989) 8:2717-2725.

(Continued)

*Primary Examiner*—Chih-Min Kam
(74) *Attorney, Agent, or Firm*—Dann, Dorfman, Herrell & Skillman; Robert C. Netter

(57) ABSTRACT

The present invention relates to hybrid glycosylated products, and in particular, to natural products such as polyketides and glycopeptides, and to processes for their preparation. The invention is particularly concerned with recombinant cells in which a cloned microbial glycosyltransferase can be conveniently screened for its ability to generate specific glycosylated derivatives when supplied with polyketide, peptide, or polyketide-peptides as substrates. The invention demonstrates that cloned glycosyltransferases when rapidly screened for their ability to attach a range of activated sugars to a range of exogenously supplied or endogenously generated aglycone templates, show a surprising flexibility towards both aglycone and sugar substrates, and that this process allows the production of glycosylated polyketides in good yield. This overcomes the problem not only of supplying novel sugar attachments to individual polyketides, including polyketides altered by genetic engineering, but also of increasing the diversity of polyketide libraries by combinatorial attachment of sugars.

2 Claims, 40 Drawing Sheets

OTHER PUBLICATIONS

Fernandez-Moreno et al., Nucleotide Sequence and Deduced Functions of a Set of Cotranscribed Genes of *Streptomyces coelicolor* A3(2) Including the Polyketide Synthase for the Antibiotic Actinorhodin, Journal of Biological Chemistry (1992) 267:19278-19290.

Bartel et al., Biosynthesis of Anthraquinones by Interspecies cloning of Actinorhodin Biosynthesis Genes in Streptomyces: Clarification of Actinorhodin in Gene Functions, J. Bacteriol. (1990) 172:4816-4826.

Davis and Chater, Spore colour in *Streptomyces coelicolor* A3(2) involves the developmentally regulated synthesis of a compound biosynthetically related to polyketide antibiotics, Molecular Microbiology, (1990) 4(10):1679-1691.

Shen et al., The *Streptomyces glaucescens* tcmKL Polyketide Synthase and tcmN Polyketide Cyclase Genes Govern the Size and Shape of Aromatic Polyketides, J. Am. Chem. Soc. (1995) 117:6811-6821.

Meurer et al., Iterative type II polyketide synthases and heteronucleases exhibit context dependent behavior in the biosynthesis of linear and angular decapolyketides, Chemistry and Biology (1997) 4:433-443.

Funa et al., A new pathway for polyketide synthesis in microorganisms, Nature Biotechnology (1999) 400:897-899.

Ferrer et al., Structure of chalcone synthase and the molecular basis of plant polyketide biosynthesis, Nature Structural Biology (1999) 6:775-784.

Lui and Thorson, Pathways and Mechanisms in the Biogenesis of Novel Deoxysugars by Bacteria, Ann. Rev. Microbiol. (1994) 48: 223-256.

Dillon et al., Molecular Characterization of a gene from *Saccharopolyspora erythraea* (*Streptomyces erythraeus*) which is involved in eythromycin biosynthesis, Mol. Microbiol. (1989) 3:1405-1414.

Haydock et al., Cloning and sequence analysis of genes involved in erythromycin biosynthesis in *Saccharopolyspora erythraea*: sequence similarities between EryG and a family of S-adenosylmethionine-dependent methyltransferases, Mol. Gen. Genet. (1991) 230;120-128.

Salah-Bey et al., Targeted gene inactivation for the elucidation of deoxysugar biosynthesis in the erythromycin producer *Saccharopolyspora erythraea*, Mol. Gen. Genet. (1998) 257:542-553.

Gaisser et al., Analysis of seven genes from the eryAI-eryK region of the erythromycin biosynthetic gene cluster in *Saccharopolyspora erythraea*, Mol. Gen. Genet. (1997) 256:239-251.

Gaisser et al., Analysis of eryBI, eryBIII, and eryBVII from the erythromycin biosynthetic gene cluster in *Saccharopolyspora erythraea*, Mol. Gen. Genet. (1998) 258:78-88.

Summers et al., Sequencing and mutagenesis of genes from the erythromycin biosynthetic gene cluster of *Saccharopolyspora erythraea* that are involved in L-mycarose and D-desosamine production, Microbiology (1997) 143:3251-3262.

Borisova et al., Biosynthesis of Desosamine: Construction of a New Macrolide Carrying a Genetically Designed Sugar Moiety, Org. Lett. (1999) 1:133-136.

Zhao et al., Engineering a Methylmycin/Pikromycin-Calicheamicin hybrid Construction of Two New Macrolides Carrying a Designed Sugar Moiety, Amer. Chem. Soc. (1999) 121:9881-9882.

Solenberg et al., Production of hybrid glycopeptide antibiotics in vitro and in *Streptomyces toyocaensis*, Chem. Biol. (1997) 4:195-202.

Madduri, et al., Production of the Antitumor drug epiruicin (4'-epidoxorubicin) and its precursor by a genetically engineered strain of *Streptomyces peucetius*, Nature Biotechnology (1998) 16:69-74.

Rowe et al., Construction of new vectors for high-level expression in actinomycetes, Gene (1998) 16:69-74.

Pereda et al., Nucleotide sequence of the ermE distal flank of the erythromycin biosynthesis cluster in *Saccharomyces erythraea*, Gene (1997) 193:65-71.

Gandecha et al., Analysis of four tylosin biosynthetic genes from the tylLM region of the *Stretomyces fradiae* genome, Gene (1997) 184:197-203.

Xue et al., A gene cluster for macrolide antibiotic biosynthesis in *Streptomyces venezuelae*: Architecture of Metabolic Delivery, PNAS (1998) USA 95:12111-12116.

Fouces et al., The tylosin biosynthetic cluster from *Streptomyces fradiae*: genetic organization of the left region, Microbiol. (1999) 145:855-868.

Hernandez et al., Characterization of a *Streptomyces antibioticus* gene cluster encoding a glycosyltransferase involved in oleandomycin inactivation, Gene (1993) 134:139-140.

Spagnoli et al., Biological Conversion of Erythronolide B, an Intermediate of Erythromycin Biogenesis, Into New "Hybrid" Macrolide Antibiotics, J Antibiotics (1982) 36: 365-375.

Trefzer et al., Genes and Enzymes involved in deoxysugar biosynthesis in bacteria, Nat. Prod. Rep. (1999) 16:283-299.

Doumith et al., Interspecies complementation in *Saccharopolyspora erythraea*, Mol. Microbiol. (1999) 34(5):1039-1048.

Miller et al., Purification, cloning, and heterologous expression of a catalytically efficient flavonol 3-0-galactosyltransferase, J. Biol. Chem. (1999) 274(48):34011-34019.

ΔeryBVΔeryCIIIΔeryA

Fig.4
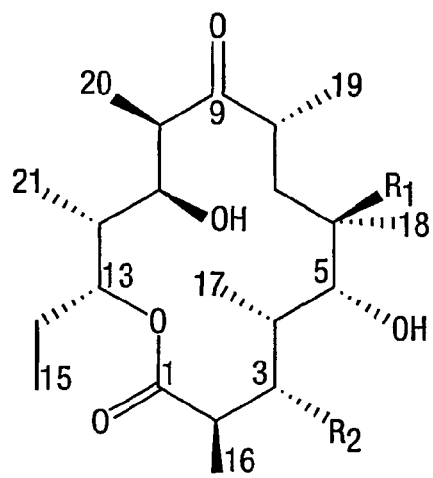
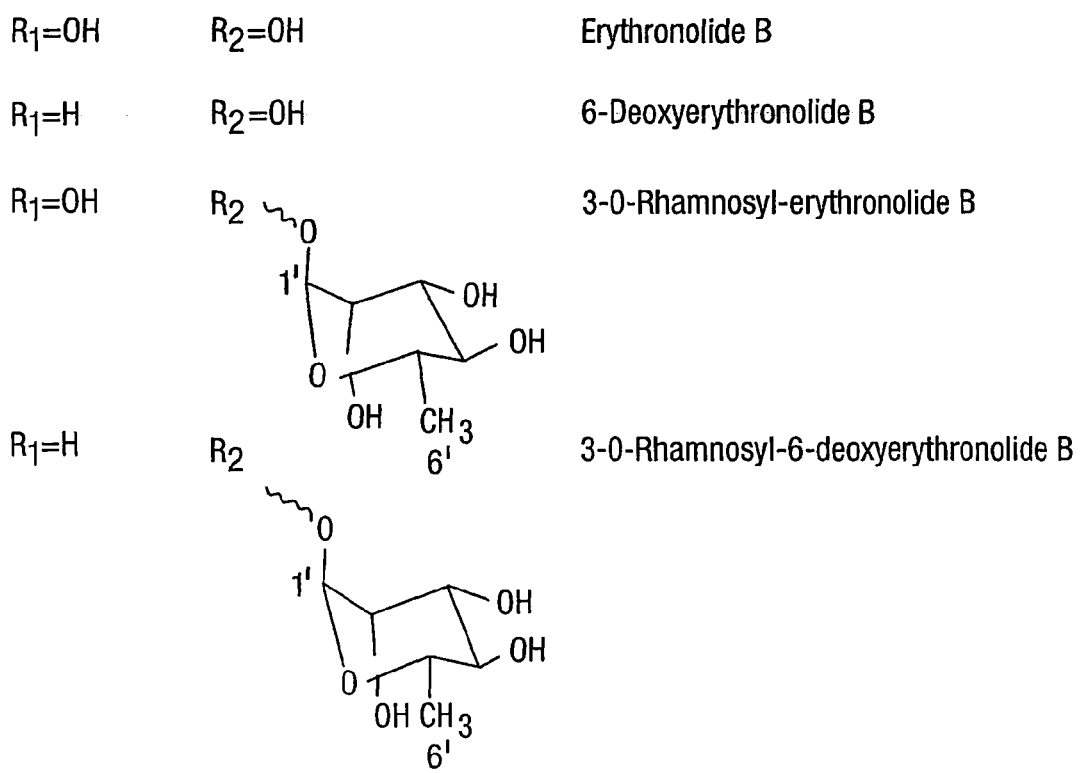
| R₁=OH | R₂=OH | Erythronolide B |
| R₁=H | R₂=OH | 6-Deoxyerythronolide B |
| R₁=OH | R₂=(rhamnosyl) | 3-O-Rhamnosyl-erythronolide B |
| R₁=H | R₂=(rhamnosyl) | 3-O-Rhamnosyl-6-deoxyerythronolide B |

5-O-Desosaminyl-tylactone

5-O-Glucosyl-tylactone

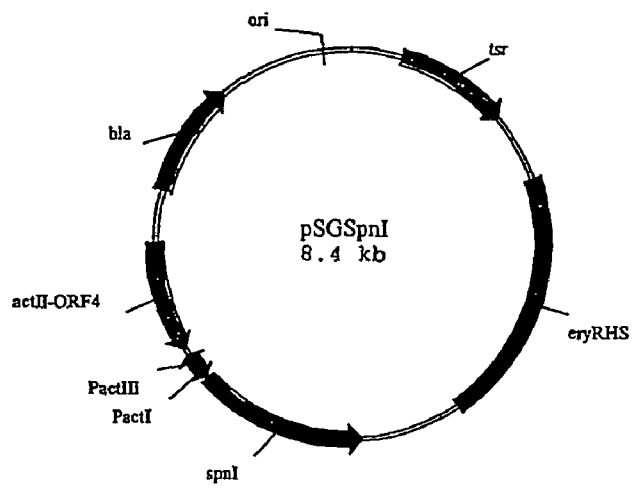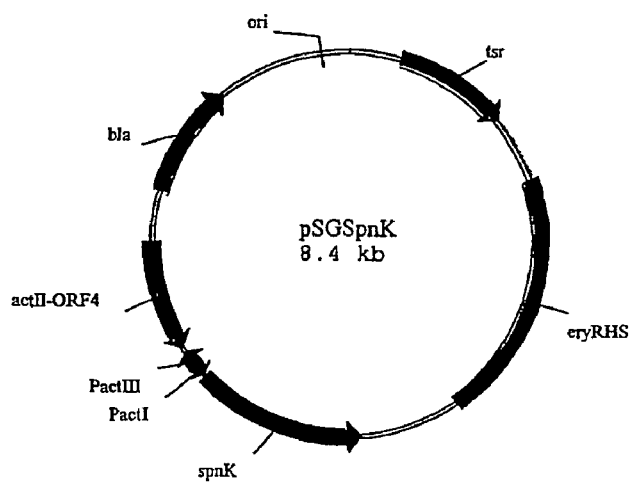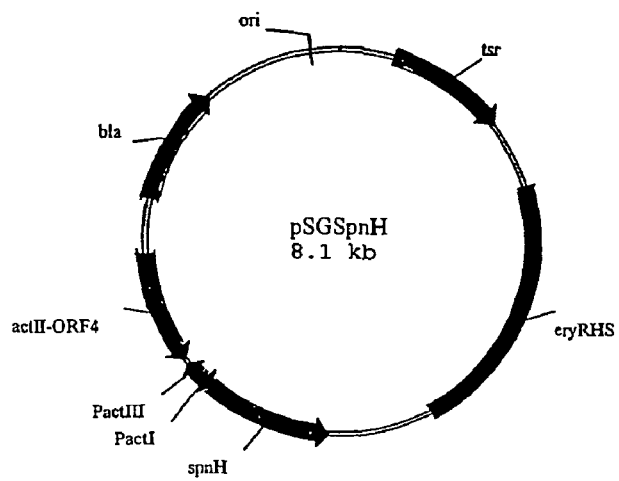
Fig. 6

```
  403 CATGGCGGGGAAGATCGGGCCGTTCGACATTGTCATCGACGACGGCAGCC 354
      |||||  ||||||||||| ||||||||||||||||||||||||||||||
17344 CATGGTGGCGAAGATCGGCCCGTTCGACATTGTCATCGACGACGGCAGCC 17393

353 ATGTCAACGACCACGTCAAGAAATCCTTCCAATCCCTGTTTCCGCACGTC 304
      ||||||||||||||||||||||||||||||||||||||||||||||||||
17394 ATGTCAACGACCACGTCAAGAAATCCTTCCAATCCCTGTTTCCGCACGTC 17443

303 CGCCCAGGTGGTTTGTACGTCATCGAGGATCTCCAGACGGCGTACTGGCC 254
      ||||||||||||||||||||||||||||||||||||||||||||||||||
17444 CGCCCAGGTGGTTTGTACGTCATCGAGGATCTCCAGACGGCGTACTGGCC 17493

253 CGGCTACGGCGGTCGCGATGGGGAACCCGCGGCCCAGCGCACCTCGATCG 204
      ||||||||||||||||||||||||||||||||||||||||||||||||||
17494 CGGCTACGGCGGTCGCGATGGGGAACCCGCGGCCCAGCGCACCTCGATCG 17543

203 ACATGCTCAAAGAACTGATCGACGGCCTGCATTATCAGGAGCGCGAATCG 154
      ||||||||||||||||||||||||||||||||||||||||||||||||||
17544 ACATGCTCAAAGAACTGATCGACGGCCTGCATTATCAGGAGCGCGAATCG 17593

153 CGGTGCGGGACCGAGCCCTCCTACACGGAACGGAACGTGGCGGCCCTGCA 104
      ||||||||||||||||||||||||||||||||||||||||||||||||||
17594 CGGTGCGGGACCGAGCCCTCCTACACGGAACGGAACGTGGCGGCCCTGCA 17643

103 CTTCTACCACAACCTGGTATTCGTGGAGAAAGGGCTCAACGCTGAGCCTG  54
      |||||||||||||||||||||||||||||||||||||||||||||| |||
17644 CTTCTACCACAACCTGGTATTCGTGGAGAAAGGGCTCAACGCTGAGACTG 17693

1 MSEIAVAPWSVVERLLLAAGAGPAKLQEAVQVAGLDAVADAIVDELVVRC  50
      ||||||||||||||||||||||||||||||||||||||||||||||||||
    1 MSEIAVAPWSVVERLLLAAGAGPAKLQEAVQVAGLDAVADAIVDELVVRC  50

51 DPLSLDESVRIGLEITSGAQLVRRTVELDHAGLRLAAVAEAAAVLRFDAV 100
      ||||||||||||||||||||||||||||||||||||||||||||||||||
   51 DPLSLDESVRIGLEITSGAQLVRRTVELDHAGLRLAAVAEAAAVLRFDAV 100

101 DLLEGLFGPVDGRRHNSREVRWSDSMTQFSPDQGLAGAQRLLAFRNRVST 150
      ||||||||||||||||||||||||||||||||||||||||||||||||||
  101 DLLEGLFGPVDGRRHNSREVRWSDSMTQFSPDQGLAGAQRLLAFRNRVST 150

151 AVHAVLAAAATRRADLGALAVRYGSDKWADLHWYTEHYEHHFSRFQDAPV 200
      ||||||||||||||||||||||||||||||||||||||||||||||||||
  151 AVHAVLAAAATRRADLGALAVRYGSDKWADLHWYTEHYEHHFSRFQDAPV 200

201 RVLEIGIGGYHAPELGGASLRMWQRYFRRGLVYGLDIFEKAGNEGHRVRK 250
      ||||||||||||||||||||||||||||||||||||||||||||||||||
  201 RVLEIGIGGYHAPELGGASLRMWQRYFRRGLVYGLDIFEKAGNEGHRVRK 250

251 LRGDQSDAEFLEDMAGKIGPFDIVIDDGSHVNDHVKKSFQSLFPHVRPGG 300
      ||||||||||||   |||||||||||||||||||||||||||||||||||
  251 LRGDQSDAEFLEDMVAKIGPFDIVIDDGSHVNDHVKKSFQSLFPHVRPGG 300

301 LYVIEDLQTAYWPGYGGRDGEPAAQRTSIDMLKELIDGLHYQERESRCGT 350
      ||||||||||||||||||||||||||||||||||||||||||||||||||
  301 LYVIEDLQTAYWPGYGGRDGEPAAQRTSIDMLKELIDGLHYQERESRCGT 350

351 EPSYTERNVAALHFYHNLVFVEKGLNAEPAAPGFVPRQALGVEGG 395
      |||||||||||||||||||||||||||||||| ||||||||||||
  351 EPSYTERNVAALHFYHNLVFVEKGLNAETAAPGFVPRQALGVEGG 395
```

Figure 6B

Fig. 7.
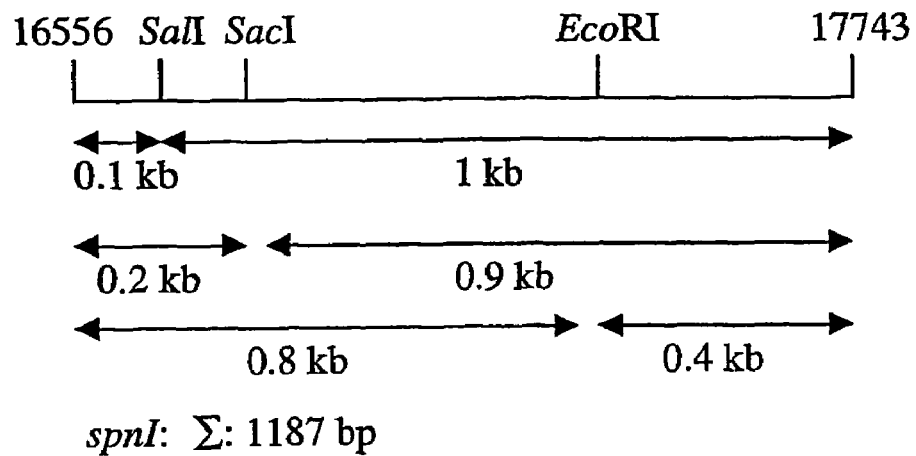
*spnI*: Σ: 1187 bp
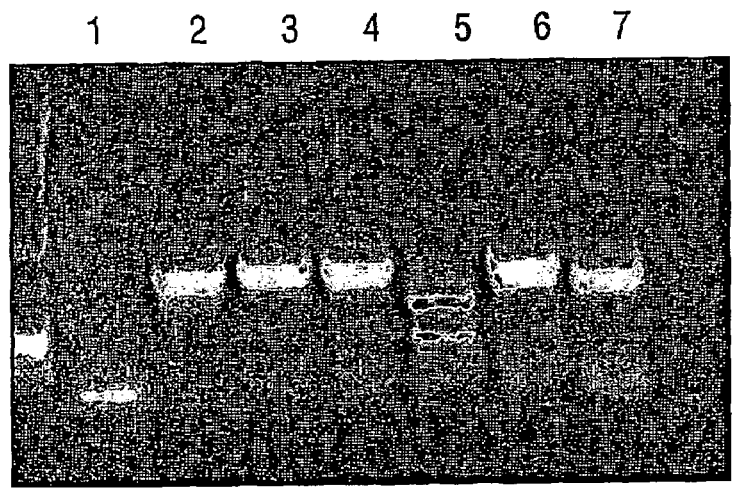
1: control SGT2 genomic DNA and primers: no PCR product
2: SGT2pSGSpnI: undigested
3: SGT2pSGSpnI: *SmaI* digested
4: SGT2pSGSpnI: *SphI* digested
5: SGT2pSGSpnI: *EcoRI* digested
6: SGT2pSGSpnI: *SacI* digested
7: SGT2pSGSpnI: *SalI* digested

Fig. 8.
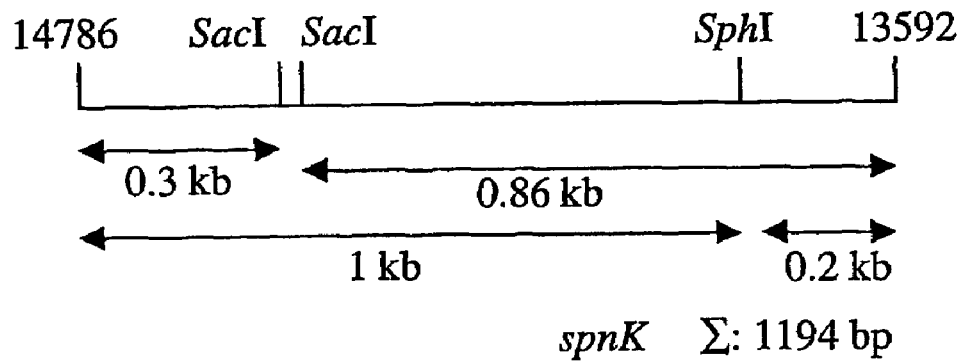
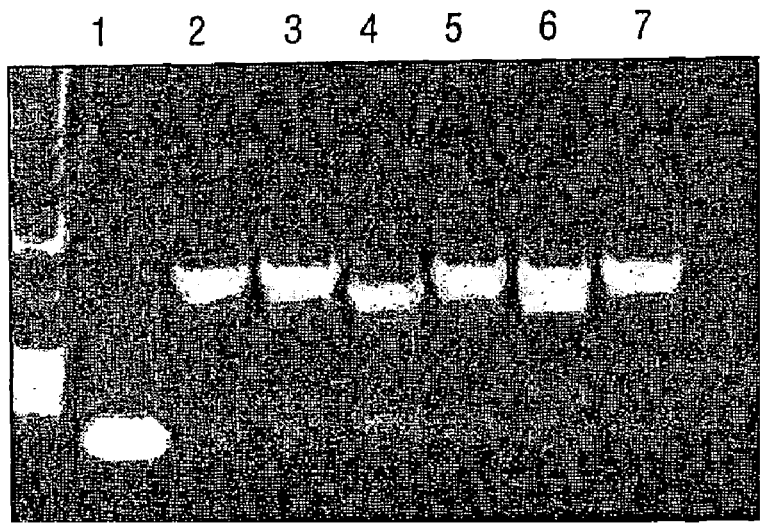
1: control SGT2 genomic DNA and primers: no PCR product
2: SGT2pSGSpnK: undigested
3: SGT2pSGSpnK: *SmaI* digested
4: SGT2pSGSpnK: *SphI* digested
5: SGT2pSGSpnK: *EcoRI* digested
6: SGT2pSGSpnK: *SacI* digested
7: SGT2pSGSpnK: *SalI* digested

Fig. 9.
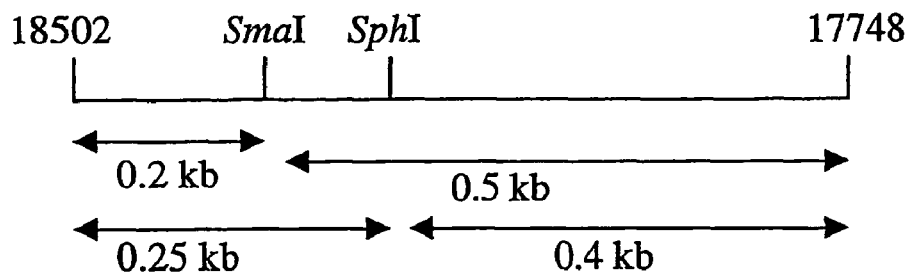
*spnH* Σ: 754 bp
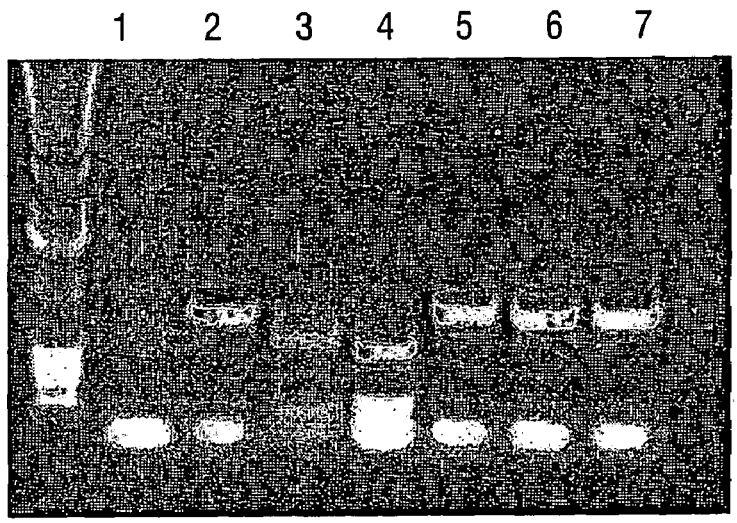
1: control SGT2 genomic DNA and primers: no PCR product
2: SGT2pSGSpnH: undigested
3: SGT2pSGSpnH: *Sma*I digested
4: SGT2pSGSpnH: *Sph*I digested
5: SGT2pSGSpnH: *Eco*RI digested
6: SGT2pSGSpnH: *Sac*I digested
7: SGT2pSGSpnH: *Sal*I digested 3-O-(2'-O-methylrhamnosyl)erythronolide B

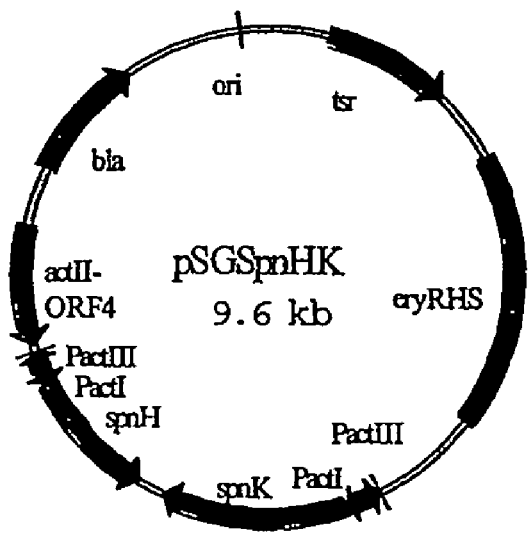
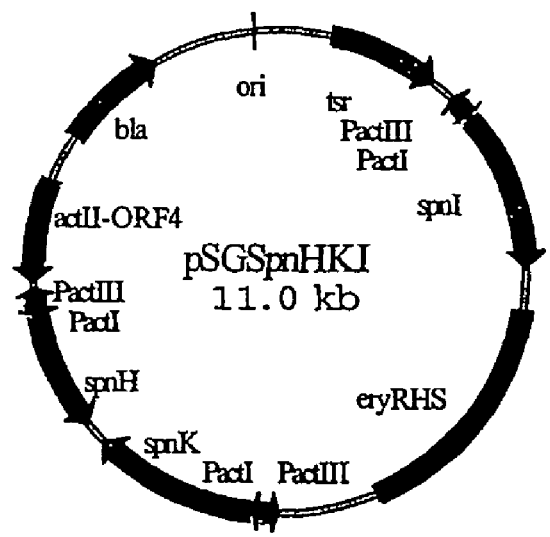
Fig. 13

3-O-(2',3'-bis-O-methylrhamnosyl)erythronolide B

3-O-(2',3',4'-tris-O-methylrhamnosyl)erythronolide B

A
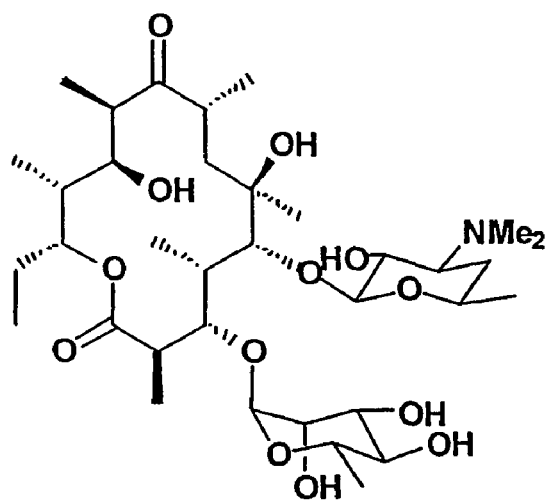
B
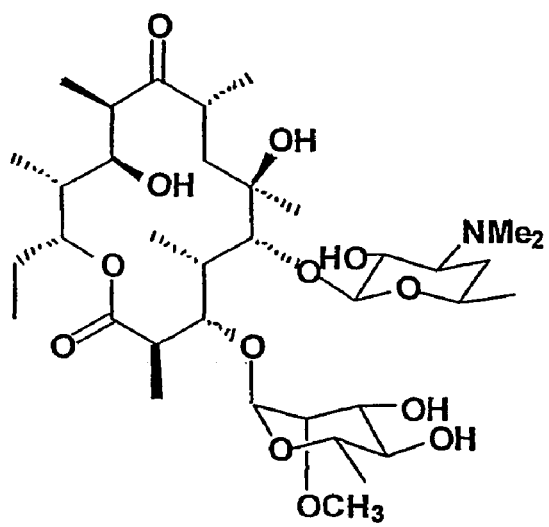
C
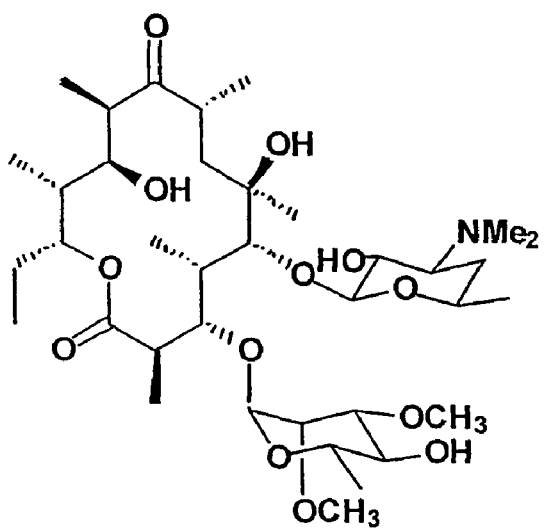
Fig. 16

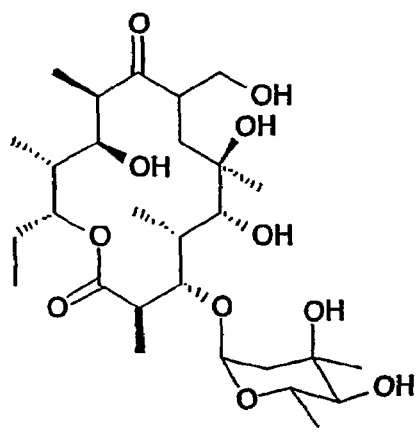
8a-hydroxy-3-O-mycarosyl erythronolide B
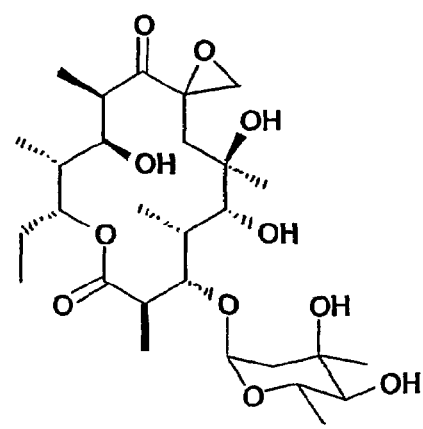
8,8a-epoxy-3-O-mycarosyl erythronolide B
Fig. 21

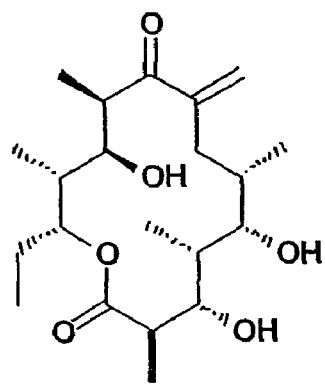
8,8a-dehydro-6-deoxyerythronolide B
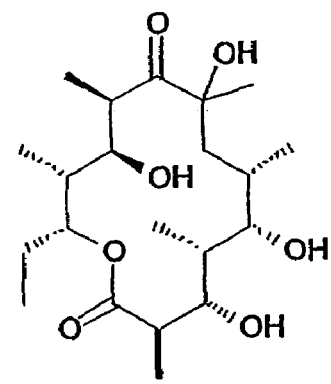
8-hydroxy-6-deoxyerythronolide B
Fig. 22

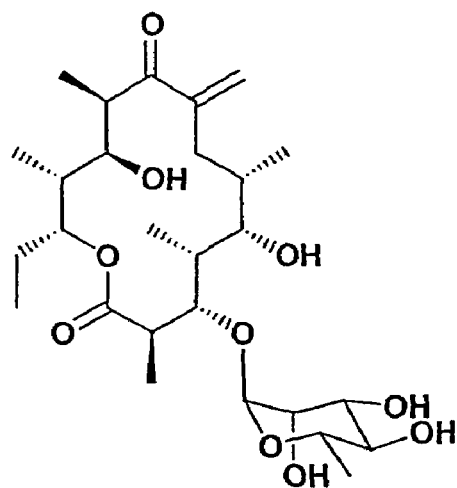
3-O-rhamnosyl-8,8a-dehydro-6-deoxyerythronolide B
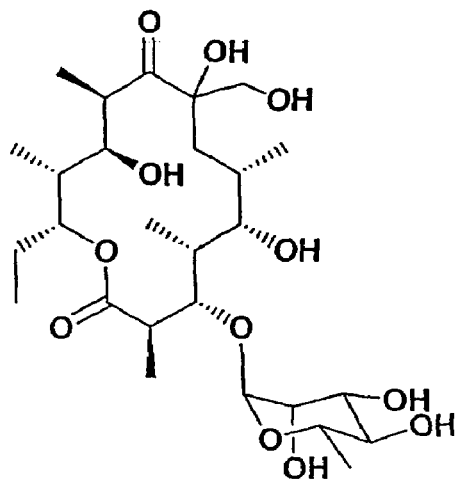
3-O-rhamnosyl-8,8a-dihydroxy-6-deoxyerythronolide B
Fig. 24

```
       CCCCGGCTGACGGCGGCGGGACCCGTCGTACGACGGCGGCGTTCCCCTGTCGTCGGCGGG
  1300 +---------+---------+---------+---------+---------+--------- 1359
       GGGGCCGACTGCCGCCGCCCTGGGCAGCATGCTGCCGCCGCAAGGGGACAGCAGCCGCCC a       P  R  L  T  A  A  G  P  V  V  R  R  R  R  S  P  V  V  G  G  -

CYTOCHROME P450 MONOOXYGENASE OLEP1

CTGCACCGGGCTCCGGTGGCCGCCGCATGAGCATCGCGTCGAACGGCGCGCGCTCGGCCC
  1360 +---------+---------+---------+---------+---------+--------- 1419
       GACGTGGCCCGAGGCCACCGGCGGCGTACTCGTAGCGCAGCTTGCCGCGCGCGAGCCGGG a       L  H  R  A  P  V  A  A  A  *
c          A  P  G  S  G  G  R  R  M  S  I  A  S  N  G  A  R  S  A  P -

CCCGCCGGCCCCTGCGCGTGATGATGACCACCTTCGCGGCCAACACGCACTTCCAGCCGC
  1420 +---------+---------+---------+---------+---------+--------- 1479
       GGGCGGCCGGGGACGCGCACTACTACTGGTGGAAGCGCCGGTTGTGCGTGAAGGTCGGCG c         R  R  P  L  R  V  M  M  T  T  F  A  A  N  T  H  F  Q  P  L  -
                      OLEG1 START (PUBLISHED)

TGGTTCCCCTGGCCTGGGCAC
  1480 +---------+---------+ 1500
       ACCAAGGGGACCGGACCCGTG c         V  P  L  A  W  A     -
```

Fig. 25

23-O-rhamnosyl-5-O-mycaminosyl-tylactone rha = rhamnose

23-O-rhamnosyl-5-O-desosaminyl-tylactone rha = rhamnose

5-O-(2'-O-)-bis-glucosyl-tylactone

Fig.32.
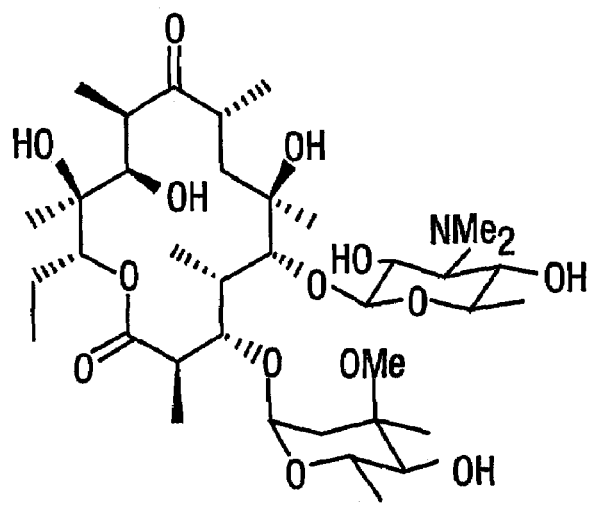
5-O-mycaminosyl-erythromycin A
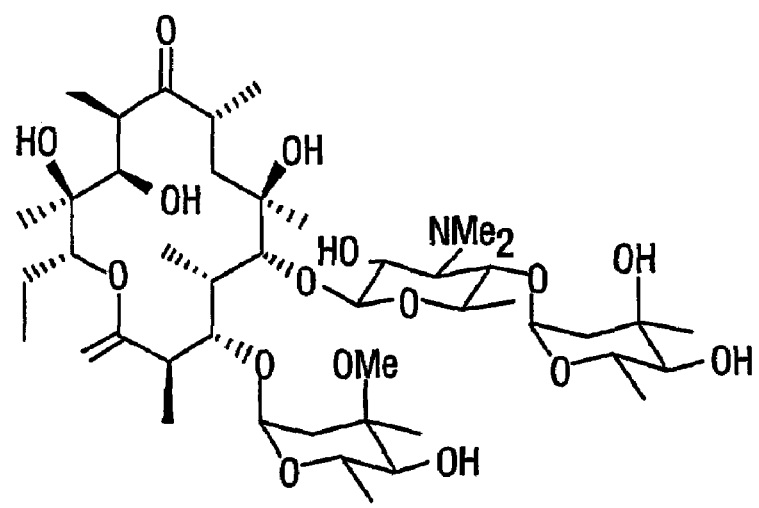
5-O-mycaminosyl-(4'-O-mycarosyl-)erythromycin A

```
  1 MTGLPRPAVRVPFHDLRDVHAATGVESEIGGALLRVAARGRYLLGAELAA  50
    ||||||||||||||||||||||||||||| |||||||| |||||||||||
  1 MTGLPRPAVRVPFHDLRDVHAATGVESEIGAALLRVAAGGRYLLGAELAA  50

51 FEERFAEYCGNAHCVAVGSGLDDARLALWALGVGEGDEVIVPSHTFIASW 100
    |||||||||||||||||||||| ||||||||||||||||||||||||||
 51 FEERFAEYCGNAHCVAVGSGLDALRLALWALGVGEGDEVIVPSHTFIASW 100

101 LAVSATGATPVPVEPGDPGEPGPGAFLLDPDRLEAALTPRTRAVMPVHLY 150
    ||||||||||||||||||||||:|||||||||||||||||||||||||||
101 LAVSATGATPVPVEPGDPGQPGPGAFLLDPDRLEAALTPRTRAVMPVHLY 150

151 GHPVDLDPVGAFAEPHGLAVVEDAAQA.TARYRGRRIGSGHRTAFSFYPG 199
    |||||||||||| ||||||||||||||  ||||||||||| |||||||
151 GHPVDLDPVGAFAERHGLAVVEDAAQAHGARYRGRRIGSGHATAFSFYPG 200

200 KNLGALGDGGAVVTSDPELADRLRLLRNYGAREKYRHEERGTNSRLDELQ 249
    |||||||||||||||||||||||||||||||||||||||||||||||||
201 KNLGALGDGGAVVTSDPELADRLRLLRNYGAREKYRHEERGTNSRLDELQ 250

250 AAVLSVKLPYLDAWNTRRREIAARYGEALAGLPGVTVPEGRV.AEPVWHQ 298
    |||||||||||||||||||||||||||||||||||||||    ||||||
251 AAVLSVKLPYLDAWNTRRREIAARYGEALAGLPGVTVPEAAAWAEPVWHQ 300

299 YVLRSPYRDRLRRRLAEAGVETLVHYPVAVHASGAYAGAGPCPAGGLPRA 348
    |||||||||||||||||||||||||||||||||||||||||||||||||
301 YVLRSPYRDRLRRRLAEAGVETLVHYPVAVHASGAYAGAGPCPAGGLPRA 350

349 ERLAGEVLSLPIGPHLPDEAVEVVIAAVQSAALDSWEEGP 388
    |||||||||||||||||||||||||||||||||||||||
351 ERLAGEVLSLPIGPHLPDEAVEVVIAAVQSAALDSWEEGP 390
```

Fig. 33

Fig.36.
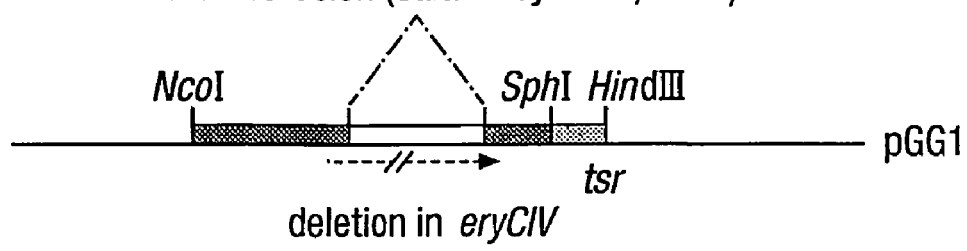
BalI/BcII fusion (Salah-Bey et al., 1998)
deletion in eryCIV
Transform into S.erythraea WT
Two thiostrepton sensitive clones-no2 and 5-were isolated
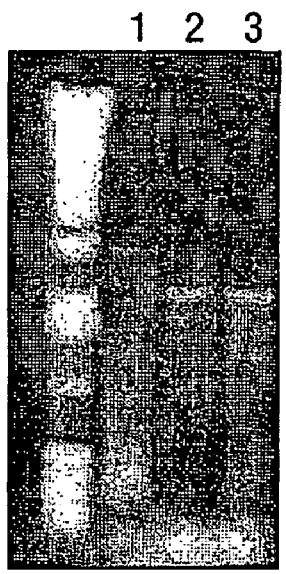
1: PCR using WT genomic as template
2: PCR using no2 genomic as template
3: PCR using no3 genomic as template
← The eryCIV deletion is inserted into the genome
Σ: S.erythraea GG1 was isolated

SEQUENCE LISTING

```
<160> NUMBER OF SEQ ID NOS: 60

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: SpeI/NheI
      ligation site

<400> SEQUENCE: 1
gagcactagc gg                                                           12

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: NcoI site
      introduced at C-terminus of eryCIII; NcoI ligation site

<400> SEQUENCE: 2
gacgaccatc gaggagaaga cgacgcgcat cgcggttac                              39

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: NcoI site
      introduced at C-terminus of eryCIII; NcoI ligation site

<400> SEQUENCE: 3
gtaaccgcga tgcgcgtcgt cttctcctcc atggtcgtc                              39

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: NcoI site
      introduced at C-terminus of eryCIII; NcoI ligation site

<400> SEQUENCE: 4

Met Arg Val Val Phe Ser Ser Met Val Val
1               5                   10
```

<210> SEQ ID NO 5
<211> LENGTH: 350
<212> TYPE: DNA
<213> ORGANISM: Saccharopolyspora spinosa

<400> SEQUENCE: 5

```
catggcgggg aagatcgggc cgttcgacat tgtcatcgac gacggcagcc atgtcaacga      60
ccacgtcaag aaatccttcc aatccctgtt tccgcacgtc cgcccaggtg gtttgtacgt     120
catcgaggat ctccagacgg cgtactggcc cggctacggc ggtcgcgatg gggaacccgc     180
ggcccagcgc acctcgatcg acatgctcaa gaactgatc gacggcctgc attatcagga     240
gcgcgaatcg cggtgcggga ccgagcccctc ctacacggaa cggaacgtgg cggccctgca     300
cttctaccac aacctggtat tcgtggagaa agggctcaac gctgagcctg              350
```

<210> SEQ ID NO 6
<211> LENGTH: 350
<212> TYPE: DNA
<213> ORGANISM: Saccharopolyspora spinosa

<400> SEQUENCE: 6

```
catggtggcg aagatcggcc cgttcgacat tgtcatcgac gacggcagcc atgtcaacga      60
ccacgtcaag aaatccttcc aatccctgtt tccgcacgtc cgcccaggtg gtttgtacgt     120
catcgaggat ctccagacgg cgtactggcc cggctacggc ggtcgcgatg gggaacccgc     180
ggcccagcgc acctcgatcg acatgctcaa gaactgatc gacggcctgc attatcagga     240
gcgcgaatcg cggtgcggga ccgagcccctc ctacacggaa cggaacgtgg cggccctgca     300
cttctaccac aacctggtat tcgtggagaa agggctcaac gctgagactg              350
```

<210> SEQ ID NO 7
<211> LENGTH: 395
<212> TYPE: PRT
<213> ORGANISM: Saccharopolyspora spinosa

<400> SEQUENCE: 7

Met Ser Glu Ile Ala Val Ala Pro Trp Ser Val Val Glu Arg Leu Leu
1               5                   10                  15

Leu Ala Ala Gly Ala Gly Pro Ala Lys Leu Gln Glu Ala Val Gln Val
                20                  25                  30

Ala Gly Leu Asp Ala Val Ala Asp Ala Ile Val Asp Glu Leu Val Val
            35                  40                  45

Arg Cys Asp Pro Leu Ser Leu Asp Glu Ser Val Arg Ile Gly Leu Glu
        50                  55                  60

Ile Thr Ser Gly Ala Gln Leu Val Arg Arg Thr Val Glu Leu Asp His
65                  70                  75                  80

Ala Gly Leu Arg Leu Ala Ala Val Ala Glu Ala Ala Val Leu Arg
                85                  90                  95

Phe Asp Ala Val Asp Leu Leu Glu Gly Leu Phe Gly Pro Val Asp Gly
                100                 105                 110

Arg Arg His Asn Ser Arg Glu Val Arg Trp Ser Asp Ser Met Thr Gln
            115                 120                 125

Phe Ser Pro Asp Gln Gly Leu Ala Gly Ala Gln Arg Leu Leu Ala Phe
        130                 135                 140

Arg Asn Arg Val Ser Thr Ala Val His Ala Val Leu Ala Ala Ala Ala
145                 150                 155                 160

```
Thr Arg Arg Ala Asp Leu Gly Ala Leu Ala Val Arg Tyr Gly Ser Asp
                165                 170                 175

Lys Trp Ala Asp Leu His Trp Tyr Thr Glu His Tyr Glu His His Phe
            180                 185                 190

Ser Arg Phe Gln Asp Ala Pro Val Arg Val Leu Glu Ile Gly Ile Gly
        195                 200                 205

Gly Tyr His Ala Pro Glu Leu Gly Ala Ser Leu Arg Met Trp Gln
    210                 215                 220

Arg Tyr Phe Arg Arg Gly Leu Val Tyr Gly Leu Asp Ile Phe Glu Lys
225                 230                 235                 240

Ala Gly Asn Glu Gly His Arg Val Arg Lys Leu Arg Gly Asp Gln Ser
                245                 250                 255

Asp Ala Glu Phe Leu Glu Asp Met Ala Gly Lys Ile Gly Pro Phe Asp
            260                 265                 270

Ile Val Ile Asp Asp Gly Ser His Val Asn Asp His Val Lys Lys Ser
        275                 280                 285

Phe Gln Ser Leu Phe Pro His Val Arg Pro Gly Gly Leu Tyr Val Ile
    290                 295                 300

Glu Asp Leu Gln Thr Ala Tyr Trp Pro Gly Tyr Gly Arg Asp Gly
305                 310                 315                 320

Glu Pro Ala Ala Gln Arg Thr Ser Ile Asp Met Leu Lys Glu Leu Ile
                325                 330                 335

Asp Gly Leu His Tyr Gln Glu Arg Glu Ser Arg Cys Gly Thr Glu Pro
            340                 345                 350

Ser Tyr Thr Glu Arg Asn Val Ala Ala Leu His Phe Tyr His Asn Leu
        355                 360                 365

Val Phe Val Glu Lys Gly Leu Asn Ala Glu Pro Ala Ala Pro Gly Phe
    370                 375                 380

Val Pro Arg Gln Ala Leu Gly Val Glu Gly Gly
385                 390                 395

<210> SEQ ID NO 8
<211> LENGTH: 395
<212> TYPE: PRT
<213> ORGANISM: Saccharopolyspora spinosa

<400> SEQUENCE: 8

Met Ser Glu Ile Ala Val Ala Pro Trp Ser Val Val Glu Arg Leu Leu
  1               5                  10                  15

Leu Ala Ala Gly Ala Gly Pro Ala Lys Leu Gln Glu Ala Val Gln Val
                20                  25                  30

Ala Gly Leu Asp Ala Val Ala Asp Ala Ile Val Asp Glu Leu Val Val
            35                  40                  45

Arg Cys Asp Pro Leu Ser Leu Asp Glu Ser Val Arg Ile Gly Leu Glu
        50                  55                  60

Ile Thr Ser Gly Ala Gln Leu Val Arg Arg Thr Val Glu Leu Asp His
 65                  70                  75                  80

Ala Gly Leu Arg Leu Ala Ala Val Ala Glu Ala Ala Val Leu Arg
                85                  90                  95

Phe Asp Ala Val Asp Leu Leu Glu Gly Leu Phe Gly Pro Val Asp Gly
            100                 105                 110

Arg Arg His Asn Ser Arg Glu Val Arg Trp Ser Asp Ser Met Thr Gln
        115                 120                 125

Phe Ser Pro Asp Gln Gly Leu Ala Gly Ala Gln Arg Leu Leu Ala Phe
    130                 135                 140
```

Arg Asn Arg Val Ser Thr Ala Val His Ala Val Leu Ala Ala Ala
145                 150                 155                 160

Thr Arg Arg Ala Asp Leu Gly Ala Leu Ala Val Arg Tyr Gly Ser Asp
                165                 170                 175

Lys Trp Ala Asp Leu His Trp Tyr Thr Glu His Tyr Glu His His Phe
            180                 185                 190

Ser Arg Phe Gln Asp Ala Pro Val Arg Val Leu Glu Ile Gly Ile Gly
        195                 200                 205

Gly Tyr His Ala Pro Glu Leu Gly Gly Ala Ser Leu Arg Met Trp Gln
    210                 215                 220

Arg Tyr Phe Arg Arg Gly Leu Val Tyr Gly Leu Asp Ile Phe Glu Lys
225                 230                 235                 240

Ala Gly Asn Glu Gly His Arg Val Arg Lys Leu Arg Gly Asp Gln Ser
                245                 250                 255

Asp Ala Glu Phe Leu Glu Asp Met Val Ala Lys Ile Gly Pro Phe Asp
            260                 265                 270

Ile Val Ile Asp Asp Gly Ser His Val Asn Asp His Val Lys Lys Ser
        275                 280                 285

Phe Gln Ser Leu Phe Pro His Val Arg Pro Gly Gly Leu Tyr Val Ile
    290                 295                 300

Glu Asp Leu Gln Thr Ala Tyr Trp Pro Gly Tyr Gly Gly Arg Asp Gly
305                 310                 315                 320

Glu Pro Ala Ala Gln Arg Thr Ser Ile Asp Met Leu Lys Glu Leu Ile
                325                 330                 335

Asp Gly Leu His Tyr Gln Glu Arg Glu Ser Arg Cys Gly Thr Glu Pro
            340                 345                 350

Ser Tyr Thr Glu Arg Asn Val Ala Ala Leu His Phe Tyr His Asn Leu
        355                 360                 365

Val Phe Val Glu Lys Gly Leu Asn Ala Glu Thr Ala Ala Pro Gly Phe
    370                 375                 380

Val Pro Arg Gln Ala Leu Gly Val Glu Gly Gly
385                 390                 395

<210> SEQ ID NO 9
<211> LENGTH: 201
<212> TYPE: DNA
<213> ORGANISM: Streptomyces antibioticus

<400> SEQUENCE: 9
ccccggctga cggcggcggg acccgtcgta cgacggcggc gttcccctgt cgtcggcggg      60
ctgcaccggg ctccggtggc cgccgcatga gcatcgcgtc gaacggcgcg cgctcggccc     120
cccgccggcc cctgcgcgtg atgatgacca ccttcgcggc caacacgcac ttccagccgc     180
tggttcccct ggcctgggca c                                               201

<210> SEQ ID NO 10
<211> LENGTH: 201
<212> TYPE: DNA
<213> ORGANISM: Streptomyces antibioticus

<400> SEQUENCE: 10
gtgcccaggc caggggaacc agcggctgga agtgcgtgtt ggccgcgaag gtggtcatca      60
tcacgcgcag gggccggcgg ggggccgagc gcgcgccgtt cgacgcgatg ctcatgcggc     120
ggccaccgga gcccggtgca gcccgccgac gacagggaa cgccgccgtc gtacgacggg     180
tcccgccgcc gtcagccggg g                                              201

```
<210> SEQ ID NO 11
<211> LENGTH: 29
<212> TYPE: PRT
<213> ORGANISM: Streptomyces antibioticus

<400> SEQUENCE: 11
```

Pro Arg Leu Thr Ala Ala Gly Pro Val Val Arg Arg Arg Ser Pro
 1               5                  10                  15

Val Val Gly Gly Leu His Arg Ala Pro Val Ala Ala Ala
            20                  25

```
<210> SEQ ID NO 12
<211> LENGTH: 46
<212> TYPE: PRT
<213> ORGANISM: Streptomyces antibioticus

<400> SEQUENCE: 12
```

Ala Pro Gly Ser Gly Gly Arg Arg Met Ser Ile Ala Ser Asn Gly Ala
 1               5                  10                  15

Arg Ser Ala Pro Arg Arg Pro Leu Arg Val Met Met Thr Thr Phe Ala
            20                  25                  30

Ala Asn Thr His Phe Gln Pro Leu Val Pro Leu Ala Trp Ala
        35                  40                  45

```
<210> SEQ ID NO 13
<211> LENGTH: 388
<212> TYPE: PRT
<213> ORGANISM: Streptomyces fradiae

<400> SEQUENCE: 13
```

Met Thr Gly Leu Pro Arg Pro Ala Val Arg Val Pro Phe His Asp Leu
 1               5                  10                  15

Arg Asp Val His Ala Ala Thr Gly Val Glu Ser Glu Ile Gly Gly Ala
            20                  25                  30

Leu Leu Arg Val Ala Ala Arg Gly Arg Tyr Leu Leu Gly Ala Glu Leu
        35                  40                  45

Ala Ala Phe Glu Glu Arg Phe Ala Glu Tyr Cys Gly Asn Ala His Cys
    50                  55                  60

Val Ala Val Gly Ser Gly Leu Asp Asp Ala Arg Leu Ala Leu Trp Ala
65                  70                  75                  80

Leu Gly Val Gly Glu Gly Asp Glu Val Ile Val Pro Ser His Thr Phe
                85                  90                  95

Ile Ala Ser Trp Leu Ala Val Ser Ala Thr Gly Ala Thr Pro Val Pro
            100                 105                 110

Val Glu Pro Gly Asp Pro Gly Glu Pro Gly Pro Gly Ala Phe Leu Leu
        115                 120                 125

Asp Pro Asp Arg Leu Glu Ala Ala Leu Thr Pro Arg Thr Arg Ala Val
    130                 135                 140

Met Pro Val His Leu Tyr Gly His Pro Val Asp Leu Asp Pro Val Gly
145                 150                 155                 160

Ala Phe Ala Glu Pro His Gly Leu Ala Val Val Glu Asp Ala Ala Gln
                165                 170                 175

Ala Thr Ala Arg Tyr Arg Gly Arg Arg Ile Gly Ser Gly His Arg Thr
            180                 185                 190

Ala Phe Ser Phe Tyr Pro Gly Lys Asn Leu Gly Ala Leu Gly Asp Gly
        195                 200                 205

```
Gly Ala Val Val Thr Ser Asp Pro Glu Leu Ala Asp Arg Leu Arg Leu
            210                 215                 220

Leu Arg Asn Tyr Gly Ala Arg Glu Lys Tyr Arg His Glu Glu Arg Gly
225                 230                 235                 240

Thr Asn Ser Arg Leu Asp Glu Leu Gln Ala Ala Val Leu Ser Val Lys
                245                 250                 255

Leu Pro Tyr Leu Asp Ala Trp Asn Thr Arg Arg Glu Ile Ala Ala
            260                 265                 270

Arg Tyr Gly Glu Ala Leu Ala Gly Leu Pro Gly Val Thr Val Pro Glu
                275                 280                 285

Gly Arg Val Ala Glu Pro Val Trp His Gln Tyr Val Leu Arg Ser Pro
        290                 295                 300

Tyr Arg Asp Arg Leu Arg Arg Leu Ala Glu Ala Gly Val Glu Thr
305                 310                 315                 320

Leu Val His Tyr Pro Val Ala Val His Ala Ser Gly Ala Tyr Ala Gly
                325                 330                 335

Ala Gly Pro Cys Pro Ala Gly Gly Leu Pro Arg Ala Glu Arg Leu Ala
            340                 345                 350

Gly Glu Val Leu Ser Leu Pro Ile Gly Pro His Leu Pro Asp Glu Ala
        355                 360                 365

Val Glu Val Val Ile Ala Ala Val Gln Ser Ala Ala Leu Asp Ser Trp
    370                 375                 380

Glu Glu Gly Pro
385

<210> SEQ ID NO 14
<211> LENGTH: 390
<212> TYPE: PRT
<213> ORGANISM: Streptomyces fradiae

<400> SEQUENCE: 14

Met Thr Gly Leu Pro Arg Pro Ala Val Arg Val Pro Phe His Asp Leu
  1               5                  10                  15

Arg Asp Val His Ala Ala Thr Gly Val Glu Ser Glu Ile Gly Ala Ala
                20                  25                  30

Leu Leu Arg Val Ala Ala Gly Gly Arg Tyr Leu Leu Gly Ala Glu Leu
            35                  40                  45

Ala Ala Phe Glu Glu Arg Phe Ala Glu Tyr Cys Gly Asn Ala His Cys
    50                  55                  60

Val Ala Val Gly Ser Gly Leu Asp Ala Leu Arg Leu Ala Leu Trp Ala
65                  70                  75                  80

Leu Gly Val Gly Glu Gly Asp Glu Val Ile Val Pro Ser His Thr Phe
                85                  90                  95

Ile Ala Ser Trp Leu Ala Val Ser Ala Thr Gly Ala Thr Pro Val Pro
                100                 105                 110

Val Glu Pro Gly Asp Pro Gly Gln Pro Gly Pro Gly Ala Phe Leu Leu
            115                 120                 125

Asp Pro Asp Arg Leu Glu Ala Ala Leu Thr Pro Arg Thr Arg Ala Val
    130                 135                 140

Met Pro Val His Leu Tyr Gly His Pro Val Asp Leu Asp Pro Val Gly
145                 150                 155                 160

Ala Phe Ala Glu Arg His Gly Leu Ala Val Val Glu Asp Ala Ala Gln
                165                 170                 175

Ala His Gly Ala Arg Tyr Arg Gly Arg Arg Ile Gly Ser Gly His Ala
```

-continued

```
                180                 185                 190
Thr Ala Phe Ser Phe Tyr Pro Gly Lys Asn Leu Gly Ala Leu Gly Asp
        195                 200                 205
Gly Gly Ala Val Val Thr Ser Asp Pro Glu Leu Ala Asp Arg Leu Arg
    210                 215                 220
Leu Leu Arg Asn Tyr Gly Ala Arg Glu Lys Tyr Arg His Glu Glu Arg
225                 230                 235                 240
Gly Thr Asn Ser Arg Leu Asp Glu Leu Gln Ala Ala Val Leu Ser Val
                245                 250                 255
Lys Leu Pro Tyr Leu Asp Ala Trp Asn Thr Arg Arg Arg Glu Ile Ala
            260                 265                 270
Ala Arg Tyr Gly Glu Ala Leu Ala Gly Leu Pro Gly Val Thr Val Pro
        275                 280                 285
Glu Ala Ala Ala Trp Ala Glu Pro Val Trp His Gln Tyr Val Leu Arg
    290                 295                 300
Ser Pro Tyr Arg Asp Arg Leu Arg Arg Arg Leu Ala Glu Ala Gly Val
305                 310                 315                 320
Glu Thr Leu Val His Tyr Pro Val Ala Val His Ala Ser Gly Ala Tyr
                325                 330                 335
Ala Gly Ala Gly Pro Cys Pro Ala Gly Gly Leu Pro Arg Ala Glu Arg
            340                 345                 350
Leu Ala Gly Glu Val Leu Ser Leu Pro Ile Gly Pro His Leu Pro Asp
        355                 360                 365
Glu Ala Val Glu Val Val Ile Ala Ala Val Gln Ser Ala Ala Leu Asp
    370                 375                 380
Ser Trp Glu Glu Gly Pro
385                 390
```

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 15
ggcgatgtgc cagcccgcga agtt                                    24

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 16
agccgtcacc ggccatggtc gtcggcatct                              30

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 17
gggggatccc atatgcgggt actgctgacg tccttcg                      37

<210> SEQ ID NO 18

-continued

```
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 18
gaaaagatct gccggcgtgg cggcgcgtga gttcctc                    37

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 19
gaaaagatct tcgtggttct ctccttcctg cggccag                    37

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 20
gggggatccc atatgcgcgt cgtcttctcc tccat                      35

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 21
ggcggatccc atatgcgcgt actgctgacc tgcttcgcc                  39

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 22
ccagatctgc ccgcatggtt cccgcctcct cgtcc                      35

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 23
gtggagatct cctttccggc gcggatcggg accg                       34

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 24
```

```
gggggatccc atatgcgggt actgctgacc tgtatcg                              37

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 25
ggaggatccc atatgcgcgt cctgctgacc tcgttcg                              37

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 26
ggggtgcaga tctgtgccgg gcgtcggccg gcggg                                35

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 27
ccgcccggcc cagatctccg cggccctcat gcgt                                 34

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 28
ttgaggccgc agcgacatat gtcctcgtcc ggga                                 35

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 29
gggcatatgc gcatagcgtt gctgaccatg ggct                                 34

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 30
ggccagatct gccgggggtg tgtgccgtgg tccggg                               36

<210> SEQ ID NO 31
<211> LENGTH: 41
<212> TYPE: DNA
```

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 31
ccggatccca tatgaccacc cagaccactc ccgcccacat c         41

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 32
cgagatctca aagcggatct ctgccggtcg gaacgga              37

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 33
cttcatatga gtgagatcgc agttgccccc tggtcg               36

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 34
aacagatctg ccgccctcga cgccgagcgc ttgcc                35

<210> SEQ ID NO 35
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 35
tcatccatat gtccacaacg cacgagatcg aaaccgt              37

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 36
tctgcagatc tctcgtcctc cgcgctgttc acgtcggcca           40

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 37
ttctagagat ctaccacaac ctggtattcg tggagaa              37

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 38
aacatatgcc ctcccagaac gcgctgtacc tgg                                    33

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 39
ctccagcaaa ggacacaccc atatgaccga tacgcaca                               38

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 40
cggcagatct gccggccgtc accaggagac gatctgg                                37

<210> SEQ ID NO 41
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 41
ggggaagctt gccgacgatg acgacgacca ccggacgaac gcatcgatta attaag           56

<210> SEQ ID NO 42
<211> LENGTH: 67
<212> TYPE: DNA
<213> ORGANISM: Artificial Sequence
<220> FEATURE:
<223> OTHER INFORMATION: Description of Artificial Sequence: Primer

<400> SEQUENCE: 42
ggggaattca gatctggtct agaggtcagc ccgcatggtt cccgcctcct cgtccgcgtc       60
cgccgct                                                                 67

<210> SEQ ID NO 43
<211> LENGTH: 69
<212> TYPE: DNA
<213> ORGANISM: Artificial Sequence
<220> FEATURE:
<223> OTHER INFORMATION: Description of Artificial Sequence: Primer

<400> SEQUENCE: 43
gggtctagat ccggacgaac gcatcgatta attaaggagg acagatatga gtgagatcgc       60
agttgcccc                                                               69

<210> SEQ ID NO 44
<211> LENGTH: 68

<212> TYPE: DNA
<213> ORGANISM: Artificial Sequence
<220> FEATURE:
<223> OTHER INFORMATION: Description of Artificial Sequence: Primer

<400> SEQUENCE: 44

```
ggggtctaga ggtcagccgc cctcgacgcc gagcgcttgc cggggcacga accccggcgc      60
ggcaggct                                                              68
```

<210> SEQ ID NO 45
<211> LENGTH: 68
<212> TYPE: DNA
<213> ORGANISM: Artificial Sequence
<220> FEATURE:
<223> OTHER INFORMATION: Description of Artificial Sequence: Primer

<400> SEQUENCE: 45

```
gggtctagat ccggacgaac gcatcgatta attaaggagg acagatatgt ccacaacgca      60
cgagatcg                                                              68
```

<210> SEQ ID NO 46
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 46

```
ggggtctaga ggtcactcgt cctccgcgct gttcacgtcg gccaggtgca atatgtc         57
```

<210> SEQ ID NO 47
<211> LENGTH: 66
<212> TYPE: DNA
<213> ORGANISM: Artificial Sequence
<220> FEATURE:
<223> OTHER INFORMATION: Description of Artificial Sequence: Primer

<400> SEQUENCE: 47

```
gggtctagat ccggacgaac gcatcgatta attaaggagg acagatatgc gcgtcgtctt      60
ctcctc                                                                66
```

<210> SEQ ID NO 48
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 48

```
ggggtctaga ggtcatcgtg gttctctcct tcctgcggcc agttcctcgc a               51
```

<210> SEQ ID NO 49
<211> LENGTH: 75

<212> TYPE: DNA
<213> ORGANISM: Artificial Sequence
<220> FEATURE:
<223> OTHER INFORMATION: Description of Artificial Sequence: Primer

<400> SEQUENCE: 49
gggtctagat ccggacgaac gcatcgatta attaaggagg acagatatga ccgatacgca    60
caccggaccg acacc    75

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 50
ggggtctaga ggtcaccagg agacgatctg gcgttccagt ccgcggatca    50

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 51
ccgccatatg agcatcgcgt cgaacggcgc gcgctcggc    39

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 52
tcagatctcc gccttcccgc catcgcgccg gtggcat    37

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 53
ggcggggaga gaggagagca tatgaacacg gcagccggcc cgacc    45

<210> SEQ ID NO 54
<211> LENGTH: 46
<212> TYPE: DNA
<213> ORGANISM: Artificial Sequence
<220> FEATURE:
<223> OTHER INFORMATION: Description of Artificial Sequence: Primer

```
<400> SEQUENCE: 54 cccctctag aggtcactcg gggacatacg gggcgacggg cagccg                       46

<210> SEQ ID NO 55
<211> LENGTH: 70
<212> TYPE: DNA
<213> ORGANISM: Artificial Sequence
<220> FEATURE:
<223> OTHER INFORMATION: Description of Artificial Sequence: Primer

<400> SEQUENCE: 55
gggggtctag atcttaatta aggaggacaa ccatggccca ttcatccgcc acggccggac       60
cgcaggccga                                                             70

<210> SEQ ID NO 56
<211> LENGTH: 71
<212> TYPE: DNA
<213> ORGANISM: Artificial Sequence
<220> FEATURE:
<223> OTHER INFORMATION: Description of Artificial Sequence: Primer

<400> SEQUENCE: 56
gggggtctag aggcatatgt gtcctcctta attaatcacc gggtttctcc cttcgctccg       60
gggagcccgg t                                                           71

<210> SEQ ID NO 57
<211> LENGTH: 65
<212> TYPE: DNA
<213> ORGANISM: Artificial Sequence
<220> FEATURE:
<223> OTHER INFORMATION: Description of Artificial Sequence: Primer

<400> SEQUENCE: 57 cccctctag atcttaatta aggaggacac ccatgacagg gctgccgcgg cccgccgtcc        60
gggtg                                                                  65

<210> SEQ ID NO 58
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 58
gggggtctag aggtcacggg ccttcctccc aggagtccag cgcggcgga                  49

<210> SEQ ID NO 59
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 59
gcctgacgaa gggtcctgcc atatggctca tattgcatt                             39

<210> SEQ ID NO 60
<211> LENGTH: 38
<212> TYPE: DNA
<213> ORGANISM: Artificial Sequence
<220> FEATURE:
<223> OTHER INFORMATION: Description of Artificial Sequence: Primer
```

```
<400> SEQUENCE: 60
gcgtgggccg gccggagatc tggccgcggg ggacagca                              38
```

HYBRID GLYCOSYLATED PRODUCTS AND THEIR PRODUCTION AND USE

This application is a continuation of U.S. application Ser. No. 10/257,549, filed Mar. 25, 2003, now abandoned, which is a 371 application of PCT/GB01/01743, filed Apr. 17, 2001, which is a continuation-in-part of U.S. application Ser. No. 09/694,218, filed Oct. 23, 2000, now abandoned and which claims priority to GB application No. 0009207.2, filed Apr. 13, 2000, The entire disclosure of each of the foregoing applications are incorporated by reference herein.

FIELD OF THE INVENTION

The present invention relates to hybrid glycosylated products, and in particular, to natural products such as polyketides and glycopeptides, and to processes for their preparation. The invention is particularly concerned with recombinant cells in which a cloned microbial glycosyltransferase can be conveniently tested for its ability to generate specific glycosylated derivatives when supplied with polyketide, peptide, or polyketide-peptides as substrates.

BACKGROUND OF THE INVENTION

Glycosylation is important for the bioactivity of many natural products, including antibacterial compounds such as the polyketide erythromycin A and the glycopeptide vancomycin, and antitumour compounds such as the aromatic polyketide daunorubicin and the glycopeptide-polyketide bleomycin. Polyketides are a large and structurally diverse class of natural products that includes many compounds possessing antibiotic or other pharmacological properties, such as erythromycin, tetracyclines, rapamycin, avermectin, monensin, epothilones and FK506. In particular, polyketides are abundantly produced by *Streptomyces* and related actinomycete bacteria. They are synthesised by the repeated stepwise condensation of acylthioesters in a manner analogous to that of fatty acid biosynthesis. The greater structural diversity found among natural polyketides arises from the selection of (usually) acetate or propionate as "starter" or "extender" units; and from the differing degree of processing of the β-keto group observed after each condensation. Examples of processing steps include reduction to β-hydroxyacyl-, reduction followed by dehydration to 2-enoyl-, and complete reduction to the saturated acylthioester. The stereochemical outcome of these processing steps is also specified for each cycle of chain extension. The polyketide chains are usually cyclised in specific ways and subject to further enzyme-catalysed modifications to produce the final polyketide. Naturally-occurring peptides produced by non-ribosomal peptide synthetases are likewise synthesised by repeated stepwise assembly, in this case of activated amino acids, and the chains produced are similarly subject to further modifications to produce the fully bioactive molecules. Mixed polyketide-peptide compounds, hereinafter defined as incorporating both ketide and amino acid units, are also known and their bioactivity is also influenced by their pattern of glycosylation and other modification. The compounds so produced are particularly valuable because they include large numbers of compounds of known utility, for example as anthelminthics, insecticides, immunosuppressants, antifungal or antibacterial agents.

*Streptomyces* and closely-related genera of filamentous bacteria are abundant producers of polyketide metabolites. Although large numbers of therapeutically important polyketides have been identified, there remains a need to obtain novel polyketides that have enhanced properties or that possess completely novel bioactivity. The inexorable rise in the incidence of pathogenic organisms with resistance to antibiotics such as 14-membered macrolides or glycopeptides represents a significant threat to human and animal health. Current methods of obtaining novel polyketide metabolites include large-scale screening of naturally-occurring strains of *Streptomyces* and other organisms, either for direct production of useful molecules, or for the presence of enzymatic activities that can bioconvert an existing polyketide, which is added to the growth medium, into specific derivatives. These procedures are time-consuming and costly, and biotransformation using whole cells may in addition be limited by side-reactions or by a low concentration or activity of the intracellular enzyme responsible for the bioconversion. Given the complexity of bioactive polyketides, they are not readily amenable to total chemical synthesis in large scale. Chemical modification of existing polyketides has been widely used, but many desirable alterations are not readily achievable by this means.

Meanwhile, methods have been developed for the biosynthesis of altered polyketides and non-ribosomally-synthesised polypeptides by the engineering of the corresponding genes encoding the polyketide synthases and polypeptide synthetases respectively. The biosynthesis of polyketides is initiated by a group of chain-forming enzymes known as polyketide synthases. Two classes of polyketide synthase (PKS) have been described in actinomycetes. One class, named Type I PKSs, represented by the PKSs for the macrolides erythromycin, oleandomycin, avermectin and rapamycin, consists of a different set or "extension module" of enzymes for each cycle of polyketide chain extension (Cortes, J. et al. Nature (1990) 348:176-178). The term "extension module" as used herein refers to the set of contiguous domains, from a β-ketoacyl-ACP synthase ("KS") domain to the next acyl carrier protein ("ACP") domain, which accomplishes one cycle of polyketide chain extension.

In-frame deletion of the DNA encoding part of the ketoreductase domain in module 5 of the erythromycin-producing PKS (also known as 6-deoxyerythronolide B synthase, DEBS) has been shown to lead to the formation of erythromycin analogues 5,6-dideoxy-3-α-mycarosyl-5-oxo-erythronolide B, 5,6-dideoxy-5-oxoerythronolide B and 5,6-dideoxy, 6 β-epoxy-5-oxoerythronolide B (Donadio, S. et al. Science (1991) 252:675-679). Likewise, alteration of active site residues in the enoylreductase domain of module 4 in DEBS, by genetic engineering of the corresponding PKS-encoding DNA and its introduction into *Saccharopolyspora erythraea*, led to the production of 6,7-anhydroerythromycin C (Donadio, S. et al. Proc Natl. Acad. Sci. USA (1993) 90:7119-7123). WO 93/13663 describes additional types of genetic manipulation of the DEBS genes that are capable of producing altered polyketides. However many such attempts are reported to have been unproductive (Hutchinson, C. R. and Fujii, I. Annu. Rev. Microbiol. (1995) 49:201-238, at p. 231).

WO 98/01546 describes the engineering of hybrid Type I PKS genes which utilise portions of PKS genes derived from more than one natural PKS, particularly derived from different organisms, and the use of such recombinant genes for the production of altered polyketide metabolites.

The second class of PKS, named Type II PKSs, is represented by the synthases for aromatic compounds. Type II PKSs contain only a single set of enzymatic activities for chain extension and these are re-used in successive cycles (Bibb, M. J. et al. EMBO J. (1989) 8:2727-2736; Sherman, D. H. et al. EMBO J. (1989) 8:2717-2725; Femandez-Moreno, M. A. et al. J. Biol. Chem. (1992) 267:19278-19290). The "extender" units for the Type II pKSs are usually acetate units, and the presence of specific cyclases dictates the preferred pathway for cyclisation of the completed chain into an aromatic product (Hutchinson, C. R. and Fujii, I. Annu. Rev. Microbiol. (1995) 49:201-238). Hybrid polyketides have been obtained by the introduction of clones Type II PKS gene-containing DNA into another strain containing a different Type II PKS gene cluster, for example by introduction of DNA derived from the gene cluster for actinorhodin, a blue-pigmented polyketide from *Streptomyces coelicolor*, into an anthraquinone polyketide-producing strain of *Streptomyces galileus* (Bartel, P. L. et al. J. Bacteriol. (1990) 172:4816-4826).

The minimal number of domains required for polyketide chain extension on a Type II PKS when expressed in a *Streptomyces coelicolor* host cell (the "minimal PKS") has been defined for example in WO 95/08548 as containing the following three polypeptides which are products of the act I genes: first KS; secondly a polypeptide termed the CLF with end-to-end amino acid sequence similarity to the KS but in which the essential active site residue of the KS, namely a cysteine residue, is substituted either by a glutamine residue, or in the case of the PKS for a spore pigment such as the whiE gene product (Chater, K. F. and Davis, N. K. Mol. Microbiol. (1990) 4:1679-1691) by a glutamic acid residue; and finally an ACP. The CLF has been stated for example in WO 95/08548 to be a factor that determines the chain length of the polyketide chain that is produced by the minimal PKS. However, it has been found (Shen, B. et al. J. Am. Chem. Soc. (1995) 117:6811-6821) that when the CLF for the octaketide actinorhodin is used to replace the CLF for the decaketide tetracenomycin in host cells of *Streptomyces glaucescens*, the polyketide product is not found to be altered from a decaketide to an octaketide. An alternative nomenclature has been proposed in which KS is designated KSα and CLF is designated KSβ, to reflect this lack of confidence in the correct assignment of the function of CLF (Meurer, G. et al. Chemistry and Biology (1997) 4:433-443). International Patent Application WO 00/00618 has recently shown that CLF and its counterpart in Type I PKS multienzymes, the so-called KSQ domain, are involved in initiation of polyketide chain synthesis. WO 95/08548 for example describes the replacement of actinorhodin PKS genes by heterologous DNA from other Type II PKS gene clusters, to obtain hybrid polyketides.

This ability to engineer PKS genes of both Type I and Type II raises the possibility of combinatorial biosynthesis of polyketides to produce diverse libraries of novel natural products which may be screened for desirable bioactivities. However, the aglycones produced by the recombinant PKS genes may be only partially, or not at all, processed by glycosyltransferases and other modifying enzymes into analogues of the mature polyketides. There is therefore an additional need to provide processes for efficient conversion of such novel aglycones into specific glycosylated products. Further, the invention of efficient processes for glycosylation would provide a new means to increase very significantly the diversity of combinatorial polyketide libraries, by utilisation of recombinant cells containing alternative cloned glycosyltransferases and alternative complements of activated sugars.

The well-known influence of glycosylation on biological activity has encouraged intensive research into the genes and enzymes governing the synthesis and attachment of specific sugar units to polyketide and polypeptide metabolites (for a review see Trefzer, A. et al. Natural Products Reports (1999) 16:283-299). Surveys of such metabolites have revealed a high diversity in the type of glycosyl substitution that is found, including a very large number of different deoxyhexoses and deoxyaminohexoses (see for a review Liu, H.-W. and Thorson, J. S. Annu. Rev. Microbiol. (1994) 48:223-256) review). The sequencing of biosynthetic gene clusters for numerous glycosylated polyketides and peptides has revealed the presence of such sugar biosynthetic genes, and also genes encoding the glycosyltransferases that transfer the glycosyl group from an activated form of the sugar, eg dTDP- or dUDP-forms, to the aglycone acceptor. For example, the eryB genes and the eryC genes of the erythromycin biosynthetic gene cluster in *Saccharopolyspora erythraea* have been identified as involved in the biosynthesis and attachment of respectively, L-mycarose and D-desosamine to the aglycone precursor of erythromycin A (Dhillon, N. et al., Mol. Microbiol. (1989) 3:1405-1414; Haydock et al. Mol. Gen. Genet. (1991) 230:120-128; Salah-Bey, K. et al. Mol Gen. Genet (1998) 257:542-553; Gaisser, S. et al., Mol. Gen. Genet. (1998) 258:78-88; Gaisser, S. et al. (1997) Mol. Gen. Genet. 256: 239-251; Summers, D. et al. Microbiology (1997) 143: 3251-3262). Both WO 97/23630 and WO 99/05283 describe the preparation of an altered erythromycin by deletion of a specific sugar biosynthetic gene, so that an altered sugar becomes attached to the aglycone. Thus WO 99/05283 describes low but detectable levels of erythromycins in which for example desosamine is replaced by mycaminose (eryCIV knockout), or desmethylmycarosyl erythromycins (eryBIII knockout) are produced.

Meanwhile methymycin analogues have been produced in which desosamine has been replaced by D-quinuvose (Borisova, S. A. et al. Org. Lett. (1999) 1:133-136), or through the incorporation of the calH gene of the calicheamycin gene cluster from *Micromonospora echinospora* into the methymycin producing strain (Zhao, L. et al. J. Amer. Chem. Soc. (1999) 121:9881-9882). Similarly, hybrid glycopeptides have been produced by using cloned glycosyltransferases from the vancomycin-producing *Amycolatopsis orientalis* to add D-xylose or D-glucose to aglycones of closely-related glycopeptides according to U.S. Pat. No. 5,871,983 (1999) (Solenberg, P. et al. Chem. Biol (1997) 4:195-202). Hybrid aromatic polyketides have also been produced, by interspecies complementation of a mutant individual sugar biosynthetic gene-with a similar gene with a different stereospecificity. Thus instead of the natural daunosamine, 4'epi-daunosamine is produced in recombinant *Streptomyces peucetius* and attached by the daunosamine glycosyltransferase to the aglycone to yield the antitumour derivative epirubicin in place of doxorubicin (Madduri, K. et al. Nature Biotechnology (1998) 16:69-74). In all these cases, the specificity of the glycosyltransferase allowed the substitution of an alternative activated sugar, but the aglycone and glycosyltransferase were not heterologous to each other. It has been found that when oleandrose glycosyltransferase oleG2 of *Streptomyces antibioticus* is cloned into the erythromycin-producing *Saccharopolyspora erythraea*, in addition to other products, the novel erythromycin in which cladinose/mycarose at C-3 is replaced by rhamnose, was obtained (Doumith, M. et al, Mol. Microbiol. (1999) 34:1039-1048). It was assumed that the activated rhamnose is produced by the host cells, and is recruited by the oleG2 glycosyltransferase in competition with the activated mycarose known to be present.

SUMMARY OF THE INVENTION

The present invention shows that cloned glycosyltransferases when rapidly screened for their ability to attach a range of activated sugars to a range of exogenously supplied or endogenously generated aglycone templates, show a surprising flexibility towards both aglycone and sugar substrates, and that this process allows the production of glycosylated polyketides in good yield. This overcomes the problem not only of supplying novel sugar attachments to individual polyketides, including polyketides altered by genetic engineering, but also of increasing the diversity of polyketide libraries by combinatorial attachment of sugars. It is particularly surprising that new glycosylated products can be produced in systems in which one or more of the components are heterologous to each other, the components being selected from the aglycone template, the sugar moiety or moieties, the glycosyltransferase, the host cell and/or genes encoding enzymes capable of modifying the sugar moiety, either before or after attachment to the aglycone template. In preferred embodiments, two, three, four or all of the components are heterologous to each other.

Accordingly, in a first aspect, the present invention provides a process for producing a hybrid glycosylated product by transferring one or more sugar moieties to an aglycone template, the process comprising:
    transforming microorganism host cells with nucleic acid encoding a glycosyltransferase (GT); and,
    providing an aglycone template to the GT so that the GT transfers one or more sugar moieties to the aglycone template to produce a hybrid glycosylated product;
    wherein one or more of the sugar moiety or moieties, the aglycone template, the glycosyltransferase or the host cells are heterologous to the other components.

Preferably, the hybrid glycosylated product is other than compounds M1 to M4 disclosed in Doumith et al (supra), e.g. an erythromycin in which cladinose/mycarose at C-3 is replaced by rhamnose.

In a further aspect, the present invention provides host cells transformed with nucleic acid encoding a glycosyltransferase (GT), wherein the GT is heterologous to the host cells and transfers one or more sugar moieties to an aglycone template within the cells to produce a hybrid glycosylated product.

In a further aspect, the present invention provides a process for producing a hybrid glycosylated product, the process comprising culturing the host cells defined above and isolating the product thus produced. In embodiments in which the aglycone template is supplied to the host cells, rather than being produced by the host cell, the process may comprise the additional step of supplying the aglycone template to the cells.

In further aspects, the present invention provides hybrid glycosylation products as obtainable by any of the processes disclosed herein.

In some embodiments of the present invention, a "hybrid glycosylated product" is one in which the aglycone template and the sugar moiety or moieties are heterologous to each other. In the processes described herein, one or more of the components of the system used to produce or modify the hybrid glycosylated product may be heterologous to one another. These components include the aglycone template, the sugar moiety or moieties, the microorganism strain/host cells, the glycosyltransferase which catalyses the attachment of the sugar moiety to the aglycone template and modifying genes capable of modifying the sugar moiety either before or after attachment to the aglycone template. The hybrid glycosylated product may also be subject of further processing or derivatisation, either by the strain or after isolating from culture medium.

In the present invention, an "aglycone template" is a polyketide, a peptide or a mixed polyketide-peptide which is capable of further processing, e.g. by a glycosyltransferase, to transfer one or more activated sugar moieties to the template.

The aglycone template may include forms of glycosylation other than that introduced by the heterologous GT. The cells may additionally contain one or more heterologous modifying genes, including but not limited to genes encoding enzymes or other proteins capable of carrying out methyl transfer, hydroxylation, or epoxidation reactions, on sugar moiety, before or after attachment to the aglycone template. Alternatively or additionally, further diversity in hybrid products can be obtained by deleting or modifying one or more homologous modifying genes.

In some embodiments, the aglycone template may be produced by the microorganism strain, either naturally or by transforming the strain with one or more genes or gene clusters capable of producing the template. By way of example, where a microorganism strain naturally produces a polyketide, the process may employ the polyketide aglycone template endogenously produced by the strain or the strain may be engineered to delete or inactivate the production of this template. In this latter case, the cells may be transformed with one or more PKS genes or a PKS gene cluster for the production of a heterologous template or, additionally or alternatively, one or more templates can be exogenously supplied to the host cells, e.g. in the screening method described below.

As mentioned above, the aglycone may be produced by the host cells by additionally cloning into the cell a recombinant polyketide synthase gene or genes either of type I or type II. The recombinant PKS genes may consist either of natural PKS genes or of mutated versions of natural PKS genes, or of hybrid PKS genes consisting of portions from at least two different natural type I PKS gene clusters, or natural type II PKS gene clusters, and may consist of a library of hybrid PKS genes of either type I or type II. Examples of PKS gene assemblies include those which produce the type I polyketide macrolides rifamycin, avermectin, rapamycin, immunomycin, or erythromycin, narbomycin, oleandomycin, pikromycin, spiramycin or tylosin; polyenes such as amphotericin B, candicidin, nystatin or pimaricin; polyethers such as monensin, salinomycin, semduramycin or tetronasin; and type II polyketides such as actinorhodin, daunorubicin, oxytetracycline or tetracycline.

A preferred host cell strain is actinomycete, more preferably strains such as *Saccharopolyspora erythraea, Streptomyces coelicolor, Streptomyces avermitilis, Streptomyces griseofuscus, Streptomyces cinnamonensis, Streptomyces fradiae, Streptomyces longisporoflavus, Streptomyces hygroscopicus, Micromonospora griseorubida, Streptomyces lasaliensis, Streptomyces venezuelae, Streptomyces antibioticus, Streptomyces lividans, Streptomyces rimosus, Streptomyces albus, Amycolatopsis mediterranei,* and *Streptomyces tsukubaensis.* Examples of preferred strains and preferred modifications to those strains to adapt them for use in the present invention are set out below.

Examples of glycosyltransferases suitable for use in accordance with the present invention (listing the GTs, their normal biosynthetic contexts and normal substrate specificities):

From the erythromycin pathway of *Saccharopolyspora erythraea*: desosaminyltransferase eryCIII and mycarosyltransferase eryBV.

From the megalomycin pathway of *Micromonospora megalomicea*: desosaminyltransferase megCIII, mycarosyltransferase megBV and megosaminyltransferase.

From the oleandomycin pathway of *Streptomyces antibioticus*: oleandrosyltransferase oleG2 (also transfers rhamnose and olivose) and desosaminyltransferase oleG1.

From the tylosin pathway of *Streptomyces fradiae*: mycaminosyltransferase tylMII deoxyallose transferase tylN and mycarosyltransferase tylCV.

From the midecamycin pathway of *Streptomyces mycarofaciens*: mycaminosyltransferase midi, deoxyallose transferase and mycarosyltransferase.

From the pikromycin/narbomycin pathway of *Streptomyces venezuelae*: desosaminyltransferase desVII.

From the spinosyn pathway of *Saccharopolyspora spinosa*: rhamnosyltransferase and forosaminyltransferase.

From the amphotericin pathway of *Streptomyces nodosus*: mycaminosyltransferase amphDI.

From the avermectin pathway of *Streptomyces avernitilis*: oleandrosyltransferase.

From the nystatin pathway of *Streptomyces*: mycaminosyltransferase.

From the polyene 67-121C pathway of *Actinoplanes caerulens*: mycosaminyltransferase, mannosyltransferase (transferring to the mycosamine).

From the elloramycin pathway of *Streptomyces olivaceaous* Tu2353: rhamnosyltransferase elmGT.

From the mithramycin pathway of *Streptomyces argillaceus*: olivosyltransferase mtmGIV.

From the daunomycin pathway of *Streptomyces peucetius*: daunosaminyltransferase dnrS.

From the urdamycin pathway of *Streptomyces fradiae* Tu2717: rhodinosyltransferase urdGT1c, olivosyltransferase urdGT1b, rhodinosyltransferase urdGT1a and olivosyltransferase urdGT2.

Preferably, the process further comprises the step of deleting or inactivating one or more genes in the microorganism host cells involved in the production of the aglycone template and/or in its subsequent processing, thereby to suppress or alter the production of the natural aglycone template or product.

In a further aspect, the present invention provides a process for producing a library capable of producing a plurality of hybrid glycosylated products, the process comprising:
  transforming microorganism host cells with nucleic acid encoding one or more glycosyltransferases (GT); and,
  providing one or more aglycone templates to the GTs so that the GTs transfer one or more sugar moieties to the aglycone template to produce said plurality of hybrid glycosylated products;
  wherein one or more of the sugar moiety or moieties, the aglycone template, the glycosyltransferase or the host cells are heterologous to the other components.

In further aspects, the present invention provides a process which further comprises screening the library for a hybrid glycosylated product having a desired characteristic.

In preferred embodiments, the library comprises 2 hybrid glycosylated products, more preferably at least 10 hybrid glycosylated products, more preferably at least 50 hybrid glycosylated products and still more preferably at least 100 hybrid glycosylated products.

In one embodiment, the present invention provides a process for screening for a hybrid glycosylated product, the process comprising:
  producing one or more different microorganism host cells, each host cell being transformed with nucleic acid encoding a glycosyltransferase (GT), wherein the GT is heterologous to the microorganism strain, to form a library of host cells;
  supplying the library with one or more aglycone templates;
  screening the library for hybrid glycosylated products produced by the GTs transferring one or more sugar moieties to the aglycone templates.

Preferably, the processes described herein further comprise isolating a host cell producing a desired hybrid glycosylated product, and treating it further (e.g. culturing the cells and isolating the product produced) so that the product can be made in bulk. Preferably, in order to maximise diversity in the hybrid products, the screening method employs at least two different host cells and/or aglycone templates and/or glycosyltransferases and/or activated sugar moieties and/or heterologous modifying genes capable of modifying the sugar moiety before or after transfer to the aglycone template, more preferably at least 3, more preferably at least 5, more preferably at least 10, more preferably at least 20 and most preferably at least 50 different cells and/or templates.

This screening method allows a large number of novel hybrid products to be generated and screened maximising the number and variety of products that can be made and tested. Desired hybrid products can be detected by their biological activity (e.g. as antibiotics).

It will be evident to those skilled in the art that production of hybrid glycosides may be done in a number of alternative ways using the present invention, e.g.:
  (1) by including all the required genes in the same cell, whether introduced separately or as a single cassette; or
  (2) stepwise, the product of one fermentation with a recombinant cell containing some of the expressed genes (either after purification or used as a filtered supernatant) in its turn being fed to a second bioconversion strain containing the rest of the expressed genes.

In the latter case, the process of the invention may comprise the steps of:
  producing one of the aglycone template or the sugar moiety in first host cells as a first product;
  optionally, purifying the first product from a culture of the first host cells; and,
  adding the first product to a second host cell comprising one or more genes encoding the other of the aglycone template or the sugar moiety and one or more glycosyltransferases, so that the sugar moiety is transferred to the glycosyltransferase, to produce the hybrid glycosylated product.

The first product may be in various degrees of purification, i.e. it may be employed as a filtered supernatant, in an isolated form or in any degree of purification compatible with production in the second host cells.

In some embodiments, the host cells may additionally contain cloned and expressed genes for sugar biosynthesis, either an entire group of genes needed to furnish a naturally occurring or novel deoxysugar, for example all the specific eryB genes from *Saccharopolyspora erythraea* or elsewhere required to make activated dTDP-mycarose from metabolic intermediates common to actinomycete cells, or such gene sets missing certain genes so that altered activated sugars are provided, or certain individual genes only that modify the type of activated sugars produced by endogenous deoxyhexose biosynthetic pathways. Thus, the present invention includes the possibility of transforming the host cells with one or more genes for modifying the aglycone template, e.g. to provide alternative positions at which glycosylation can be introduced, to modify existing functionality in the template or which are involved in the downstream processing of the hybrid glycosylation products.

The cells may be additionally cultivated in the presence of cerulenin, which specifically suppresses endogenous polyketide biosynthesis, or additionally or alternatively mutated to delete or otherwise inactivate one or more of the PKS genes naturally present within the cells, in either case the result is to decrease competition with the supplied aglycone.

In a further aspect, the present invention provides the hybrid glycosylated products produced by any one of the processes described herein.

In a further aspect, the present invention provides novel hybrid glycosylated products resulting from the attachment of sugar moieties to aglycone templates. Examples of hybrid products include those comprising:
(a) one or more natural sugars linked to an erythronolide at the 7-position.
(b) one or more rhamnose or substituted (e.g. methyl) rhamnose sugars linked to an erythronolide
(c) one or more mycarose or substituted mycarose sugars linked to an erythronolide;
and combinations of (a), (b) and (c) sugar substituents on an erythronolide (e.g. erythronolide B).

Examples of hybrid products based on an erythromycin template include those comprising:
(a) one or more natural sugars linked to erythromycin at the 7-position;
(b) one or more mycarose or substituted mycarose sugars linked to an erythromycin;
(c) one or more mycaminose or substituted mycaminose sugars linked to an erythromycin;
and combinations of (a), (b) and (c) sugar substituents on an erythromycin (e.g. erythromycin A).

Examples of hybrid products based on a tylactone template include those comprising:
(a) one or more glucose or substituted glucose sugars linked to a tylactone;
(b) one or more desosaminose or substituted desosaminose sugars linked to a tylactone;
(c) one or more mycaminose or substituted mycaminose sugars linked to a tylactone;
(d) one or more rhamnose or substituted rhamnose sugars linked to a tylactone;
and combinations of (a), (b), (c) and (d) sugars substituents such as a rhamnose and a mycaminose sugar linked to a tylactone (e.g. 23-O-rhamnosyl 5-O-mycaminosyl tylactone).

Specific examples of hybrid products of the invention are:
3-O-(2'-O-methylrhamnosyl)erythronolide B
3-O-(2',3'-bis-O-methylrhamnosyl)erythronolide B
3-O-(2',3',4'-tris-O-methylrhamnosyl)erythronolide B
8a-hydroxy-3-O-mycarosyl erythronolide B
8,8a-epoxy-3-O-mycarosyl erythronolide B
8,8a-dehydro-6-deoxyerythronolide B
8-hydroxy-6-deoxyerythronolide B
3-O-(2'-O-methylrhamnosyl)erythromycin D
3-O-(2',3'-bis-O-methylrhamnosyl)erythromycin D
3-O-2',3',4'-tris-O-methyl rhamnosyl)erythromycin D
5-O-mycaminosyl-erythromycin A
5-O-mycaminosyl-4"-O-mycarosyl erythromycin A
5-O-glucosyl-tylactone
5-O-desosaminyl-tylactone
23-O-rhamnosyl 5-O-mycaminosyl tylactone
5-O (2'-O)-bis-glucosyl-tylactone
3-O-rhamnosyl-8,8a-dehydro-6-deoxyerythronolide B
3-O-rhamnosyl-8,8a-dihydroxy-erythronolide B
3,5 di-O-mycarosyl erythronolide B.

In a further aspect, the present invention provides a process for assembling a gene set in a cassette for transformation of a host cell for carrying out the processes described herein. The strategy to prepare gene cassettes with different combinations of glycosyltransferase- and methyltransferase genes is adapted from a technique previously described (WO 00/77181A2) to build gene cassettes expressed under the control of the actII-Orf4 regulator The expression of these gene cassettes in a suitable strain background is a powerful approach to generate novel post-PKS modified polyketides in a random or directed fashion. The method is based upon the introduction of XbaI restriction sites at the 3' and 5'-end of the PCR fragments. The introduction of a XbaI site at the 5'-end of the PCR fragment which is sensitive to the Dam methylase of the strain background will protect this site from further XbaI digest. To retain the Shine Dalgarno sequence 5' of the respective gene the pSG142 derived constructs which contain these genes were used as a template. Using plasmid DNA isolated from dam host strains (such as $E.\ coli$ ET 12567—McNeil et al, (1992) Gene, 111, 61-68), the amplified genes can be isolated as XbaI fragments. Using a host strain with an active Dam methylase such as $E.\ coli$ DH10B these fragments can be sequentially cloned into gene cassettes. This technique provides the means to build gene cassettes of different length and different order using the same strategy over and over again. An overview of the strategy described here and the isolated gene cassettes is depicted in FIG. 18. In some cases, expression of the terminal gene surprisingly was increased when nucleic acid encoding a histidine tag was fused to the 3' end of the gene cassette.

Where more than one gene is required to be introduced and expressed in the said host cells, many ways will readily occur to the person skilled in the art as to how this goal may be achieved in a way that ensures that there will be coordinated expression of all the required gene products. However, the present invention further provides a novel process and expression cassette for achieving this goal which, in one embodiment, allows the stepwise contiguous head to tail assembly of individual sugar pathway genes, or of heterologous modifying genes, or of both types of gene, and thereby not only places them on a single region of DNA under the control of a common promoter, but also thereby facilitates their further genetic manipulation together as a single unit or cassette. Each gene to form part of such a cassette assembly can be either a natural or modified gene, or synthetic versions of a natural genes, and such natural genes may be obtained either from the said host cells or may be heterologous to the said host cells.

Accordingly, in a still further aspect, the present invention provides an expression cassette comprising one or more glycosyltransferase genes and one or more auxiliary genes, operably linked under the control of a promoter. As described above, the auxiliary genes may be genes encoding proteins involved in the biosynthesis of one or more sugars (a 'sugar pathway gene') to enable a host cell transformed with the expression cassette to produce one or more sugar moieties for subsequent transfer to an aglycone template. Other examples of heterologous auxiliary genes include enzymes involved in the processing of sugar moieties or the aglycone template, either before or after the sugar moiety is transferred to the aglycone by the GT. Examples of these enzymes include methyltransferases and P450s which are responsible for hydroxylation of the aglycone template. Preferably, the genes in the cassette are under the control of a single, preferably strong, promoter. Further, the present inventors have found that by incorporating a nucleic acid sequence encoding a histidine tag adjacent to (or immediately 3') the terminal gene in the expression cassette so that expression of genes in the cassette which are distal to the promoter is improved.

In a further aspect, the present invention provides a process of producing an expression cassette comprising one or more glycosyltransferase genes and one or more auxiliary genes, the process comprising operably linking the genes together under the control of a promoter. The process may comprise the further step of transforming a host cell with the expression cassette and expressing the genes comprised within it to produce the GT and proteins encoded by the auxiliary genes.

In a further aspect, the present invention provides a host cell transformed with such an expression cassette.

Embodiments of the present invention will now be described by way of example and not limitation with reference to the accompanying figures.

BRIEF DESCRIPTION OF THE FIGURES

FIG. 4: Structure of 3-O-rhamnosyl-erythronolide B+3-O-rhamnosyl-6-deoxy-erythronolide B.

FIG. 6: Overview of the plasmids pSGSpnI, pSGSpnK and pSGSpnH.

FIG. 6B: Comparison of the DNA (top) and amino acid (bottom) sequence of spnI/SpnI (DNA: SEQ ID NO: 5; amino acid: SEQ ID NO: 7) and the published sequence accession AY007564 (DNA: SEQ ID NO: 6; amino acid: SEQ ID NO: 8). The changes included into the corrected nucleotide and amino acid sequence are underlined.

FIG. 7: Analysis of spnI using chromosomal DNA of SGT2pSGSpnI as a template.

FIG. 8: Analysis of spnK using chromosomal DNA of SGT2pSGSpnK as a template.

FIG. 9: Analysis of spnh using chromosomal DNA of SGT2pSGSpnH as a template.

FIG. 13: Overview of the plasmids pSGSpnHK and pSGSpnHKI.

FIG. 16: Structures of 3-O-rhamnosyl-erythromycin D (A); 3-O-(2'-O-methylrhamnosyl) erythromycin D (B); and 3-O-(2',3'-bis-O-methylrhamnosyl)erythromycin D (C).

FIG. 21: Structures of 8a-hydroxy-3-O-mycarosyl erythronolide B and 8,8a-epoxy-3-O-mycarosyl erythronolide B.

FIG. 22: Structures of 8,8a-dehydro-6-deoxyerythronolide B and 8-hydroxy-6-deoxyerythronolide B.

FIG. 24: Structures of 3-O-rhamnosyl-8,8a-dehydro-6-deoxyerythronol-ide B and 3-O-rhamnosyl-8,8a dihydroxy-6-deoxyerythronolide B.

FIG. 25: DNA sequence (top strand: SEQ ID NO: 9; bottom strand: SEQ ID NO: 10) of the oleG1 start region (accession number AJ002638). First amino acid sequence is SEQ ID NO: 11 and second amino acid sequence is SEQ ID NO: 12.

FIG. 32: Structures of 5-O-mycaminosyl-erythromycin A and 5-O-mycaminosyl-4"-O-mycarosyl-erythromycin A.

FIG. 33: Sequence of the genes tylMl, tylM3 and tylB, showing 8 amino acid changes in tylB as compared to the published sequence (top: SEQ ID NO: 13; bottom: SEQ ID NO: 14).

FIG. 36: Restriction map of plasmid pGG1.

MATERIALS AND METHODS

Figure 1A:
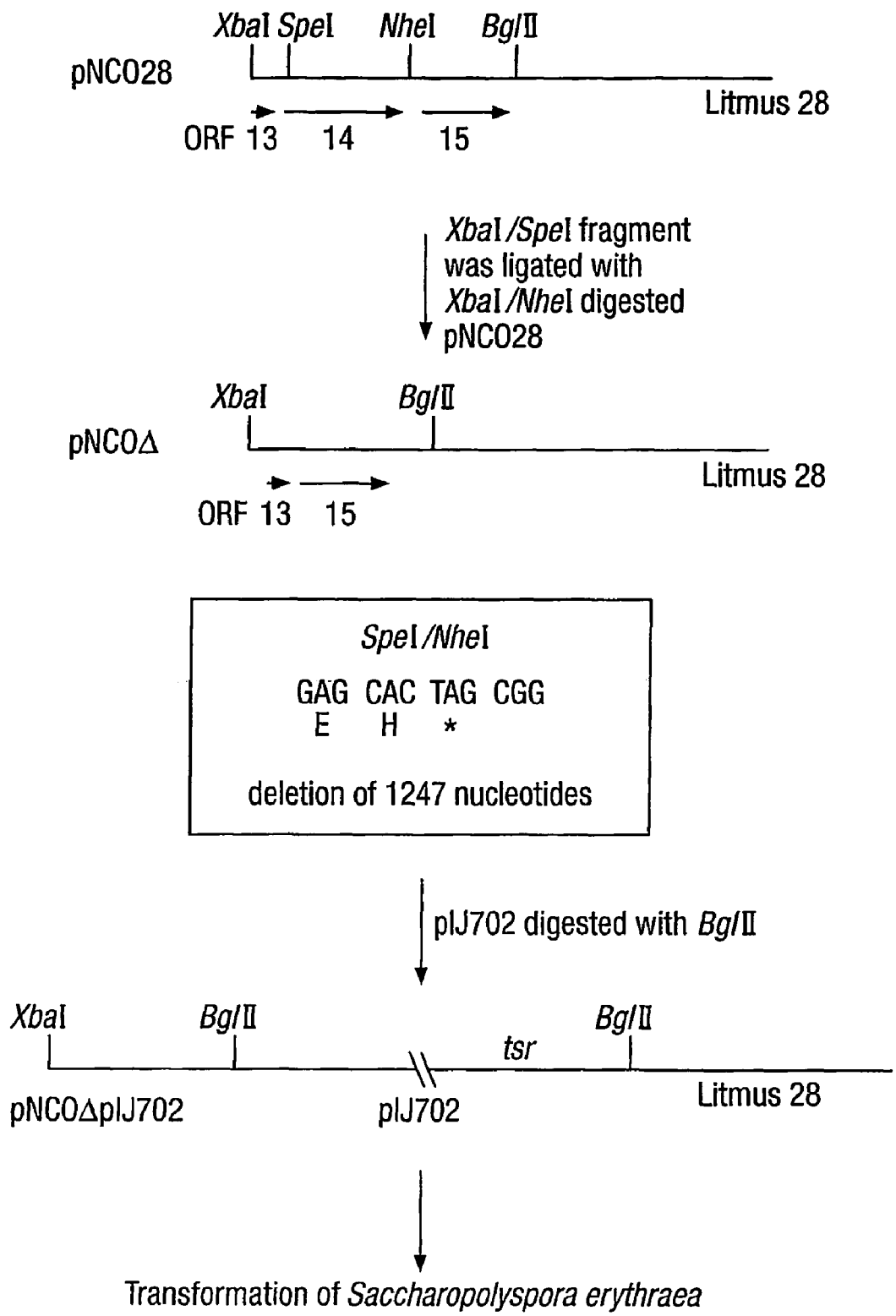
FIG. 1A: Scheme for the isolation of S. erythaea Δorfl4 containing a 1247-bp deletion in eryB:. tsr, thiostrepton resistance. SpeI/Nhel is SEQ ID NO: 1.

Escherichia coli XL1-Blue MR (Stratagene) and E. coli DH1B (GibcoBRL) were grown in 2.times.TY medium as described by Sambrook et al. (Molecular Cloning, A Laboratory Manual, 2nd Edition (1989) Cold Spring Harbor, N.Y., Cold Spring Harbor Press). Vectors Litmus28 and pUC18 were obtained from New England Biolabs and vector pQE-16 from QIAGEN. Vector pIJ702 (Katz et al. J. Gen. Microbiol. (1983) 129:2703-2714) was kindly provided by D. A. Hopwood (John Innes Institute, Norwich, UK). Vector pUC2G which contains a 6.2 kb BglII fragment from cosAB35 cloned into pUC18 was kindly provided by J. Salas (University of Oviedo, Spain). Vector pLQD1 which contains a 5076 bp PvuII fragment from cosmid cos25G8 cloned into pUC18 was kindly provided by J. Salas University of Oviedo, Spain).

Cosmid no 7 which has been isolated from a Streptomyces fradiae cosmid library, was kindly provided by J. Corts. E. coli transformants were selected with 100 ug/ml ampicillin.

The *Saccharopolyspora erythraea* NRRL 2338-red variant strain (Hessler et al., Appl. Microbiol. Biotechnol. (1997) 47:398-404) was kindly provided by J. M. Weber and was routinely maintained on M1-102 agar (Kaneda et al. J. Biol. Chem. (1962) 237:322-327), R2T20 (Yamamoto et al. J. Antibiot. (1986) 34:1304-1313), R2T2 (same as R2T (Weber et al. J. Bacterial. (1985)164:425-433), but without peptone), and TSB (Difco) for liquid cultures at 30° C. *Bacillus subtilis* ATCC 6633 was used in bioassays to assess erythromycin production as described (Gaisser et al. (1997), supra). These assays were modified to investigate erythromycin production after feeding with erythronolide B or 3-α-mycarosyl-erythronolide B kindly provided by J.-M. Michel (Hoechst Marion Roussel, Romainville, France). Both metabolites (10 µl of 10 mM stock solution) were applied to agar wells cut into the *S. erythraea* lawn and incubated at 30° C. overnight as described (Gaisser et al. (1997) supra) and the development of zones of inhibition in the *B. subtilis* lawn around *S. erythraea* colonies was assessed. Expression vectors in *S. erythraea* were derived from plasmid pCJR24 (Rowe et al., Gene (1998) 216:215-223). Plasmid-containing *S. erythraea* were selected with 25 µg/ml thiostrepton. To investigate the production of antibiotics, *S. erythraea* strains were grown in sucrose-succinate medium (Caffrey et al. (1992) FEBS Lett. 304:225-228) as described (Gaisser et al., (1997) supra) and the cells were harvested by centrifugation. Tylactone was kindly provided by B. Wilkinson of Glaxo Group Research, Stevenage, UK. 150 µl of a 100 mg/ml stock solution was added to a 500 ml *S. erythraea* expression culture.

DNA Manipulation and Sequencing

DNA manipulations, PCR and electroporation procedures were carried out as described in Sambrook et al. (1989) supra. Protoplast formation and transformation procedures of *S. erythraea* were as described (Gaisser et al., (1997) supra). Southern hybridizations were carried out with probes labelled with digoxigenin using the DIG DNA labelling kit (Boehringer Mannheim). DNA sequencing was performed by the method of Sanger et al. (P.N.A.S. USA (1977) 74:5463-5467), using automated DNA sequencing on double stranded DNA templates with an Applied Biosystems 373A sequencer. Sequence data were analysed using the Staden Programs (Staden, R. Nucl. Acids Res. (1984) 12:521-528) and the Genetics Computer Group (GCG, version 10) software package (Devereux et al., Nucl. Acids Res. (1984) 12:387-395).

Extraction and Mass Spectrometry 10 ml of each fermentation broth was centrifuged and the pH of the supernatant was adjusted to pH 9. The supernatant was extracted twice with an equal volume of ethyl acetate. The organic layer was dried over $Na_2SO_4$, evaporated to dryness and then redissolved in 0.3 ml acetonitrile/water (1:1 v/v). Mass spectrometry was performed on a BioQ (Micromass, Manchester, UK) or a Finnigan LCQ (Finnigan, Calif.) instrument. High resolution spectra were obtained on a Bruker BioApex II FT-ICR (Bruker, Bremen, FRG).

For NMR analysis, the bacterial broth was centrifuged and the pH of the supernatant was adjusted to about pH 9. The supernatant was extracted with three equal volumes of ethyl acetate, the extracts were combined, dried ($Na_2SO_4$) and evaporated under reduced pressure to yield a yellow solid. Final purification was achieved using reversed phase preparative HPLC on a Gilson 315 System using a 21 mm.times.250 mm Prodigy ODS3 column (Phenomenex, Macclesfield, UK.). The mobile phase was pumped at a flow rate of 21 ml/min as a binary system consisting of 45% $CH_3CN$, 55% 20 mM $NH_4OAc$ [pH 5.5 with HCOOH] increasing linearly to 95% $CH_3CN$ over 25 min.

$^1$H Nuclear Magnetic Resonance (NMR) spectra were acquired at 800 MHz on a Bruker Avance DRX800 and at 500 MHz on a Bruker Avance DRX500. $^{13}$C NMR spectra were acquired at 100 MHz on a Bruker Avance DRX400 spectrometer. Samples for NMR analysis were dissolved in $CD_3OD$ and the experiments were performed at 300 K. High Performance Liquid Chromatography (HPLC) was performed on a Hewlett Packard HP1100 liquid chromatograph. Liquid Chromatography Mass Spectrometry (LC-MS), Tandem Mass Spectrometry (MS/MS) and MS$^n$ spectra were obtained on a Finnigan MAT (San Jose, Calif.) LCQ. High resolution Quadrupole Time Of Flight MS/MS data were obtained on a Micromass (Macclesfield, U.K.) QTOF. High resolution MS$^n$ were obtained on a Bruker Daltonics BioApex II 4.7 T Fourier Transform Ion Cyclotron Resonance mass spectrometer using PEG as external calibrant.

Chromosomal Deletion of eryBV (FIG. 1A)

Vector pNCO28 (Gaisser et al, 1997) (FIG. 1A) was digested with XbaI/NheI and XbaI/SpeI, a 3.8 kb band and a 0.4 kb fragment were isolated, ligated and transformed into *E. coli* DH10B. A vector construct pNCOΔ containing the deletion of eryBV was isolated and the SpeI/NheI ligation site was verified by sequencing. After digestion with BglII, the plasmid was ligated with BglII-cut pIJ702 and used to transform *E. coli* DH10B. Plasmid pNCOΔpIJ702 was isolated and used to transform *S. erythraea* NRRL 2338 (red variant). Colonies were selected for thiostrepton resistance and integration into the chromosome was confirmed by Southern analysis. To allow for the second recombination event, integrants were subcultured at least four times in TSB medium (Difco) at 30° C. Single colonies were screened for thiostrepton sensitivity and for erythromycin production. The 1247 nt chromosomal deletion of eryBV was verified by using the 1.5 kb NcoI fragment of plasmid pNCOΔ to probe ClaI/PstI- and NcoI-digested chromosomal DNA of the wild type strain and of mutant Δorf14. Analysis of the wild type *S. erythraea* showed the expected 2.9 kb ClaI/PstI and 2.7 kb NcoI band after hybridization. When chromosomal DNA of Δorf14 was treated similarly, only a 1.6 kb ClaI/PstI and a 1.5 kb NcoI fragment were detected indicating that eryBV had been removed. The mutant Δorf14 was tested in a bioassay. No zones of inhibition were observed around the *S. erythraea* colonies in the *B. subtilis* lawn, indicating that no erythromycin A is produced by the mutant strain.

Figure 1B:
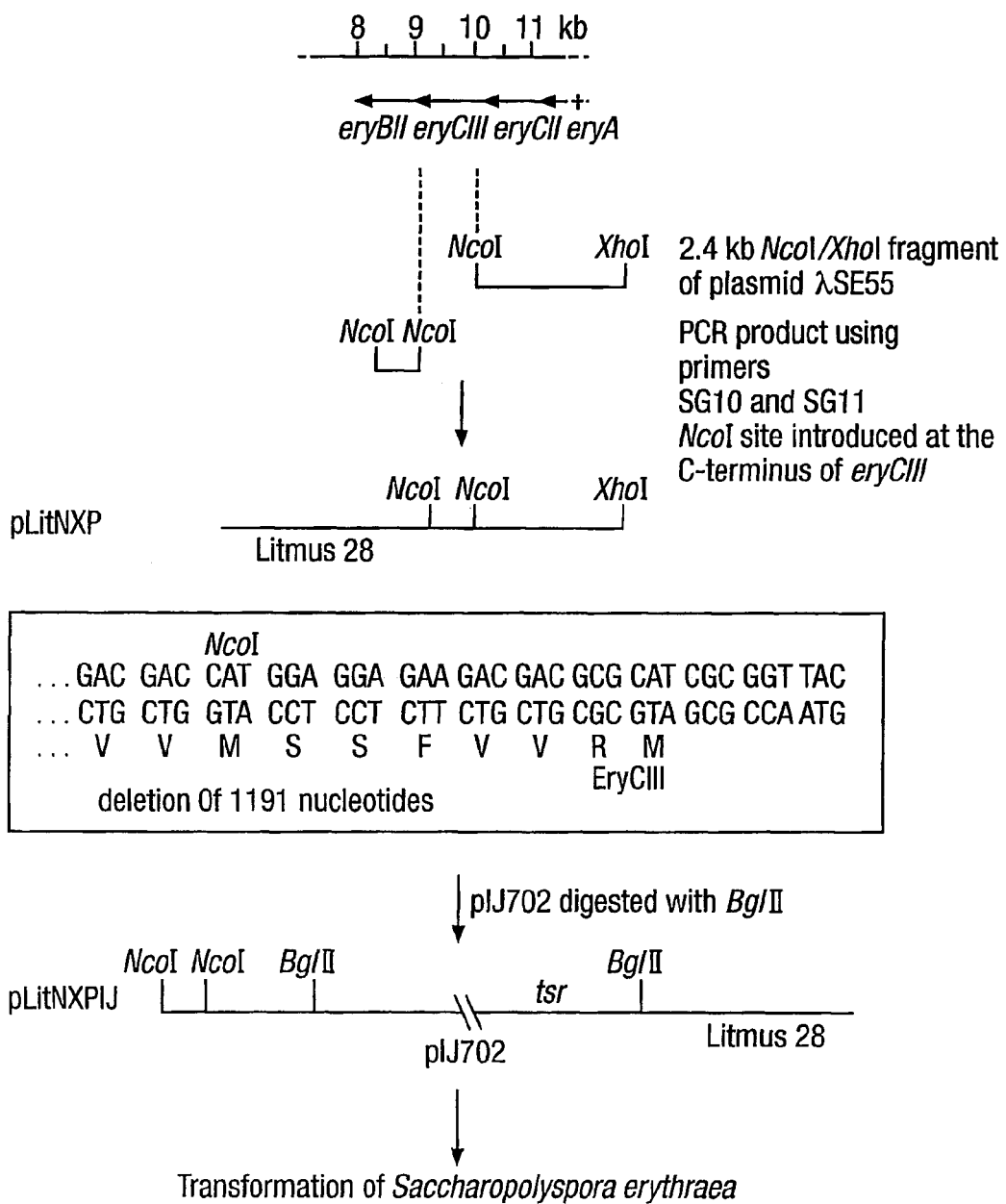
FIG. 1B: Scheme for the isolation of S. erythaea strain DM containing both a deletion in eryBV and a 1191-bp deletion in eryCIII. tsr, thiostrepton resistance. Provided sequence is SEQ ID NO: 2 (top strand) and SEQ ID NO: 3 (bottom strand).

Chromosomal Deletion of eryCIII (FIG. 1B)

Plasmid λSE55 (Haydock et al., Mol. Gen. Genet. (1991) 230:120-128) was digested with NcoI/XhoI (FIG. 1B) and a 2.4 kb fragment was cloned into NcoI/XhoI digested vector Litmus28. Plasmid pLitNX was isolated and its identity verified by restriction digestion and by sequencing. Using λSE55 as a template and primers SG10 5'-GGCGATGTGCCAGC-CCGCGAAGTT-3' (SEQ ID NO: 15) and SG11 5'-AGC-CGTCACCGGCCATGGTCGTCGGCATCT-3' (SEQ ID NO: 16), a 573 nt fragment was amplified using PCR, treated with T4 polynucleotide kinase and cloned into SmaI-cut pUC18. The sequence was checked, and this plasmid construct was then digested with NcoI and a 0.5 kb fragment was isolated, ligated into NcoI-digested pLitNX and used to transform *E. coli* DH10B. Plasmid pLitNXP was isolated and the correct insert was verified, by restriction digestion and sequencing, as bearing a 1191 nt deletion in eryCIII. The construct pLitNXP was digested with BglII and ligated into pIJ702 previously treated with BglII, and the mixture was used to transform *E. coli* DH10B. Plasmid pLitNXPIJ was isolated and used to transform the *S. erythraea* mutant Δorf14 as described. Integration was verified by Southern blot hybridization. After subculturing, single colonies were screened for thiostrepton sensitivity as described above. Thiostrepton sensitive colonies were grown in small patches and agar plugs taken from well-grown areas were placed on bioassay plates containing 3 alpha-mycarosyl-erythronolide B. No inhibition zone was observed around colonies of the isolated *S. erythraea* strain DM (Δorf14Δorf8). The 1247 nt chromosomal deletion was verified in Southern blot hybridizations as described for the mutant Δorf14. The 1191 nt chromosomal eryCIII deletion was verified using a digoxygenin-labelled 573 nt DNA fragment, amplified by primers SG10 and SG11, to probe NcoI- and ClaI/BglII-digested chromosomal DNA of the wild type strain and of the mutant DM (Δorf14Δorf8). Analysis of the wild type *S. erythraea* showed the expected 1.7 kb NcoI and 12.4 kb BglII bands after hybridization. When chromosomal DNA of DM was treated similarly, only an 11 kb BglII and a 0.5 kb NcoI fragment were detected indicating that 1.2 kb of the eryCIII gene had been removed.

Chromosomal Deletion of eryA

Figure 2:
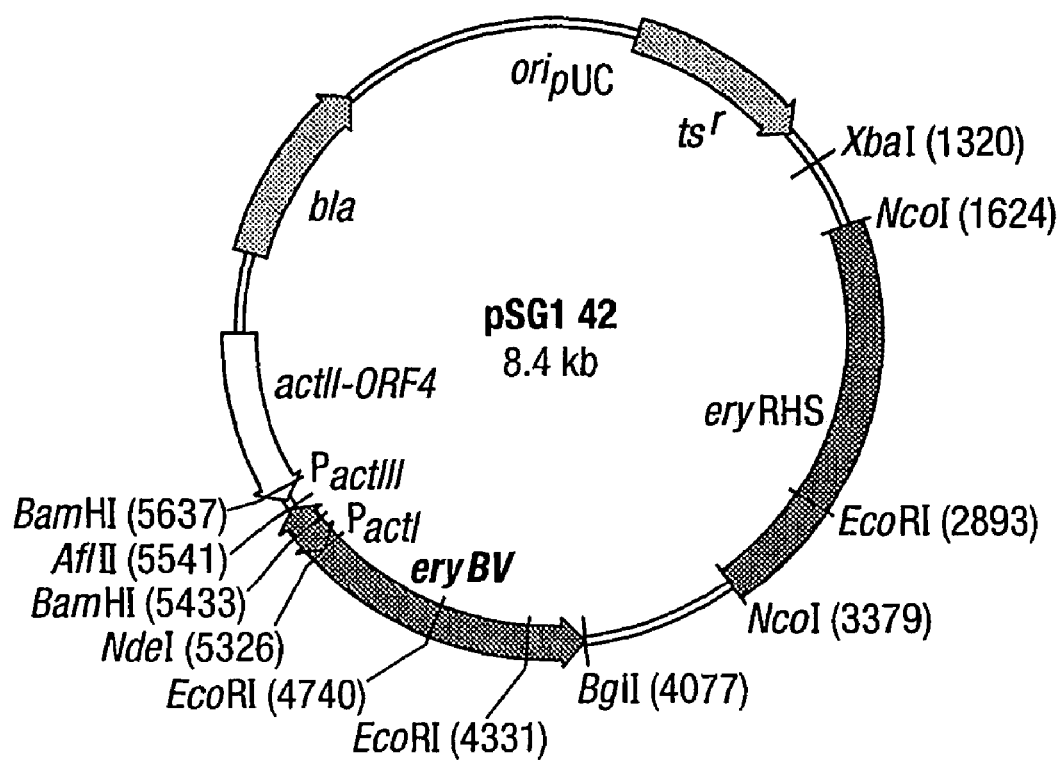
FIG. 2: Structure of expression plasmid pSG142. EryRHS denotes a DNA fragment from the ermE-distal flank of the erythromycin biosynthetic gene cluster.
Figure 3:
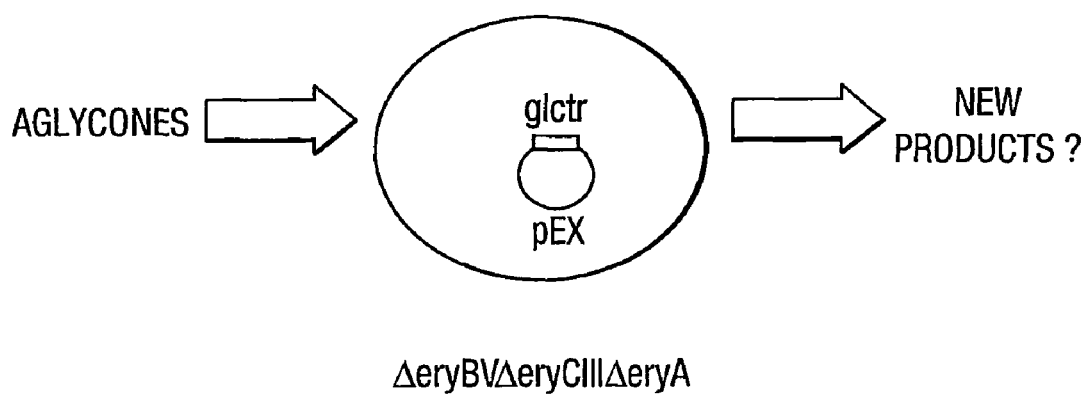
FIG. 3: General scheme for the screening of the cloned glycosyltransferase (glctr) for their ability to glycosylate aglycones in vivo.

To allow the feeding of different aglycones to a *S. erythraea* mutant strain housing heterologous glycosyltransferase genes, the eryA deletion previously described for JC2/Del60 (Rowe et al., (1998) supra) was also introduced into the *S. erythraea* mutant strain DM. *S. erythraea* SGT2 was isolated (FIG. 2) and all three deletions (ΔeryAΔBVΔCIII) were verified by Southern blot analysis. Culture broths of *S. erythraea* SGT2 were analysed by electrospray mass spectrometry. No peaks corresponding to either erythromycin A or precursor metabolites were found.

Construction of Expression Plasmid for eryBV

The gene eryBV was amplified by PCR using the primers 1518 5'-GGGGGATCCCATATGCGGGTACTGCT-GACGTCCTTCG-3' (SEQ ID NO: 17) and 1519 5'-GAAAAGATCTGCCGGCGTGGCGGCGCGT-GAGTTCCTC-3' (SEQ ID NO: 18), which introduce a BamHI and a NdeI site at the 5' end and a BglII site at 3' end of eryBV. After treatment with T4 polynucleotide kinase the PCR product was cloned into SmaI-cut pUC18 and the resulting plasmid used to transform *E. coli* DH10B. The sequence of eryBV in the isolated plasmid was checked, and this plasmid was then digested using the restriction enzymes BamHI and BglII, a 1.2 kb fragment was isolated and ligated into the identically-digested vector fragment of pQE-16, which introduced a C-terminal His$_6$-tag into EryBV. The pQE-16 derived plasmid was digested with NdeI and XbaI and a 2.2 kb fragment was isolated and ligated into vector pCJR24 previously cut with NdeI and XbaI, to give plasmid pSG2414. To allow the recombination of this plasmid into the genome of *S. erythraea*, a 1.7 kb NcoI fragment from cosmid cos6B (Gaisser et al., (1997) supra) from the ermE distal flank of the erythromycin biosynthetic cluster (Pereda et al., Gene (1997) 193:65-71) was isolated and cloned into the pQE-16 derived NcoI site. This final construct was named pSG142.

Construction of Expression Plasmid for eryCIII

For expression of eryCIII, primers SG14 5'-GAAAA-GATCTTCGTGGTTCTCTCC-TTCCTGCGGCCAG-3' (SEQ ID NO: 19) and SG15 5'-GGGGGATCCCATAT-GCGCGTCGTCTTCTCCTCCAT-3' (SEQ ID NO: 20) were used to amplify eryCIII with λSE55 as template. The 1287 bp DNA fragment was isolated, treated with T4 polynucleotide kinase and cloned into SmaI cut pUC18. After transformation into *E. coli* DH10B the construct was isolated and the sequence of eryCIII was verified. After digestion with NdeI/BglII, a 1.2 kb fragment was isolated, ligated with the vector fragment of NdeI/BglII digested pSG142 and used to transform *E. coli* DH10B. Plasmid pSGCIII was isolated.

Construction of Expression Plasmid for oleG2

For expression of oleG2, the primers Ole3 5'-GGCG-GATCCCATATGCGCGTAC-TGCTGACCTGCTTCGCC-3' (SEQ ID NO: 21) and Ole4 5'-CCAGATCTGCCCG-CATGGTTCCCGCCTCCTCGTCC-3' (SEQ ID NO: 22) were used to amplify oleG2 using plasmid pUC2G or chromosomal DNA of *Streptomyces antibioticus* as a template. The PCR fragment was isolated, treated with T4 polynucleotide kinase and cloned into SmaI cut pUC18. After transformation into *E. coli* DH10B the construct was isolated and the sequence of oleG2 was verified. After digestion with NdeI/BglII, a 1.3 kb fragment was isolated, ligated with the vector fragment of NdeI/BglII digested pSG142 and used to transform *E. coli* DH10B. Plasmid pSGOLEG2 was isolated.

Construction of Expression Plasmid for tylM2

For expression of tylM2 (Gandecha et al., Gene (1997) 184:197-203) the primers Tyl1 5'-GTGGAGATCTCCTTTC-CGGCGCGGATCGGGACCG-3' (SEQ ID NO: 23) and Tyl2 5'-GGGGGATCCCATATGCGGGTACTGCT-GACCTGTATCG-3' (SEQ ID NO: 24) were used to amplify tylM2 using cosmid no 7 as a template or chromosomal DNA of *Streptomyces fradiae*. Primer Tyl2 was chosen on the basis of sequence comparisons of known glycosyltransferases, which indicated the methionine at position 21 of the published sequence (accession no X81885) to be the start codon. The changes to the DNA sequence of tylM2 noted in a recent update (X81885/June 1999) were confirmed independently in this work. The PCR DNA fragment was isolated, treated with T4 polynucleotide kinase and cloned into SmaI cut pUC18. After transformation into *E. coli* DH10B the construct was isolated and the sequence of tylM2 was verified. After digestion with NdeI/BglII, a 1.3 kb fragment was isolated, ligated with the vector fragment of NdeI/BglII digested pSG142 and used to transform *E. coli* DH10B. Plasmid pSG-TYLM2 was isolated.

Construction of Expression Plasmid for desVII

For expression of desVII (Xue et al., (1998) P.N.A.S. USA, 95:12111-12116) the primers Pik1 5'-GGAGGATC-CCATATGCGCGTCCTGCTGACCTCGTTCG-3' (SEQ ID NO: 25) and Pik2 5'-GGGGTGCAGATCTGTGC-CGGGCGTCGGCCGGCGGG-3' (SEQ ID NO: 26) were used to amplify desVII using genomic DNA of *Streptomyces venezuelae* as a template. The PCR DNA fragment was isolated, treated with T4 polynucleotide kinase and cloned into SamI cut pUC18. After transformation into *E. coli* DH10B the construct was isolated and the sequence of desVII was verified. After digestion with NdeI/BglII, a 1.3 kb fragment was isolated, ligated with the vector fragment of NdeI/BglII digested pSG142 and used to transform *E. coli* DH10B. Plasmid pSGDESVII was isolated.

Construction of Expression Plasmid for tylH

For expression of tylH (Fouces et al., Microbiology, (1999) 145:855-868) the primers TylH1 5'-CCGCCCGGCCCA-GATCTCCGCGGCCCTCATGCGT-3' (SEQ ID NO: 27) and TylH2 5'-TTGAGGCCGCAGCGACATATGTC-CTCGTCCGGGGA-3' (SEQ ID NO: 28) were used to amplify tylH using genomic DNA of *Streptomyces fradiae* as a template. The PCR DNA fragment was isolated, treated with T4 polynucleotide kinase and cloned into SmaI cut pUC18. After transformation into *E. coli* DH10B the construct was isolated. After digestion with NdeI/BglII, a 1.6 kb fragment was isolated, ligated with the vector fragment of NdeI/BglII digested pSG142 and used to transform *E. coli* DH10B. Plasmid pSGTYLH1 was isolated.

Construction of Expression Plasmid for tylN

For expression of tylN (Fouces et al., 1999) the primers Tyl5 5'-GGGCATATGCGCATAGCGTTGCTGAC-CATGGGCT-3' (SEQ ID NO: 29) and Tyl4 5'-GGCCA-GATCTGCCGGGGGTGTGTGCCGTGGTCCGGG-3' (SEQ ID NO: 30) were used to amplify tylN using genomic DNA of *Streptomyces fradiae* as a template. The PCR DNA fragment was isolated, treated with T4 polynucleotide kinase and cloned into SmaI cut pUC18. After transformation into *E. coli* DH10B the construct was isolated. After digestion with NdeI/BglII, a 1.3 kb fragment was isolated, ligated with the vector fragment of NdeI/BglII digested pSG142 and used to transform *E. coli* DH10B. Plasmid pSGTYLN was isolated.

Construction of Expression Plasmids for both tylH and tylN

Plasmid pSGTYLH was digested with BglII and pSGTylN was digested with AflII/NheI. The fragments were submitted to fill-in reactions using Kienow polymerase (Sambrook et al., (1989) supra). The pSGTYLH vector derived DNA was isolated and ligated with the 1.5 kb fragment encoding TylN. *E. coli* DH10B was transformed with the ligation mixture. Plasmid pSGTYLHN was isolated.

Construction of Expression Plasmid for oleD

For expression of oleD (Hernandez et al., Gene (1993) 134:139-140) the primers OleD1 5'-CCGGATCCCATAT-GACCACCCAGACCACTCCCGCCCACATC-3' (SEQ ID NO: 31) and OLED2 5'-CGAGATCTCAAAGCG-GATCTCTGCCGGTCGGAACGGA-3' (SEQ ID NO: 32) were used to amplify oleD using pLQD1 (Luis M. Quiros) or chromosomal DNA of *Streptomyces antibioticus* as a template. The PCR DNA fragment was isolated, treated with T4 polynucleotide kinase and cloned into SmaI cut pUC18. After transformation into *E. coli* DH10B the construct was isolated. After digestion with NdeI/BglII, a 1.3 kb fragment was isolated, ligated with the vector fragment of NdeI/BglII digested pSG142 and used to transform *E. coli* DH10B. Plasmid pSGOLED was isolated.

Isolation of 3-O-rhamnosyl-erythronolide B and 3-O-rhamnosyl-6-deoxyerythronolide B The plasmid pSGOLEG2 was transformed into *S. erythraea* mutant DM cells and culture broths of the transformed strains were analysed as described by Gaisser et al. (1997) and by Gaisser et al. (1998). Analysis of the *S. erythraea* mutant DM(pSGOLEG2) by electrospray mass spectroscopy revealed the presence of only two distinct new peaks, at m/z 555 and 571 respectively, which were not present in the culture broth of the *S. erythraea* strain DM examined under the same conditions of growth, extraction and analysis. MS/MS experiments revealed that the ion with m/z of 571 fragmented into an ion with m/z of 425 (corresponding to the sodium salt of erythronolide B, EB-Na+) corresponding to the loss of m/z 146 (rhamnose). The fragmentation pattern of the ion of m/z 555 was identical to that of the fragment of m/z 571, but shifted lower by 16 mass units, indicating a missing hydroxy group. This was evidence that the compound with m/z 555 represents rhamnosyl-6-deoxyerythronolide B. To confirm these structures, 1.5 litres of culture broth were used to purify 4.6 mg of 3-O-rhamnosyl-erythronolide B and 2.7 mg of 3-O-rhamnosyl-6-deoxyerythronolide B. Both compounds were analysed and the structures were fully confirmed by $^1$H and $^{13}$C NMR.

TABLE 1

$^1$H NMR Data for 3-O-rhamnosyl-erythronolide B

| Proton | $\delta_H$ | multiplicity | coupling |
|---|---|---|---|
| 2-H | 2.84 | dq | 10.4, 6.8 |
| 3-H | 3.71 | d | 10.4 |
| 4-H | 2.16 | dd | 7.4, 3.6 |
| 5-H | 3.52 | d | 3.6 |
| 7-H$_a$ | 1.94 | dd | 14.7, 10.3 |
| 7-H$_b$ | 1.43 | dd | 14.7, 2.6 |
| 8-H | 2.70 | m | |
| 10-H | 3.03 | qd | 6.9, 1.7 |
| 11-H | 3.96 | dd | 9.7, 1.5 |
| 12-H | 1.65 | qd | 9.7, 7.1 |
| 13-H | 5.44 | ddd | 9.7, 4.4, 0.6 |
| 14-H$_a$ | 1.71 | m | |
| 14-H$_b$ | 1.49 | m | |
| 15-H$_3$ | 0.88 | dd | 7.4, 7.4 |
| 16-H$_3$ | 1.20 | d | 6.8 |
| 17-H$_3$ | 1.02 | d | 7.4 |
| 18-H$_3$ | 1.30 | s | |
| 19-H$_3$ | 1.13 | d | 7.1 |
| 20-H$_3$ | 0.96 | d | 6.8 |
| 21-H$_3$ | 0.94 | d | 7.1 |
| 1'-H | 4.88 | d | 1.9 |
| 2'-H | 3.94 | dd | 3.2, 1.9 |
| 3'-H | 3.64 | dd | 9.5, 3.2 |
| 4'-H | 3.42 | dd | 9.5, 9.5 |
| 5'-H | 3.85 | dq | 9.5, 6.2 |
| 6'-H$_3$ | 1.28 | d | 6.2 |

TABLE 2

$^{13}$C NMR Data for 3-O-rhamnosyl-erythronolide B

| Carbon | $\delta_c$ |
|---|---|
| C1 | 175.4 |
| C2 | 44.3 |
| C3 | 87.5 |
| C4 | 36.1 |
| C5 | 80.6 |
| C6 | 74.4 |
| C7 | 36.3 |
| C8 | 44.7 |
| C9 | 219.9 |
| C10 | 39.3 |
| C11 | 69.5 |
| C12 | 39.8 |
| C13 | 74.5 |
| C14 | 25.5 |
| C15 | 9.3 |
| C16 | 14.5 |
| C17 | 7.6 |
| C18 | 16.4 |
| C19 | 17.4 |
| C20 | 8.1 |
| C21 | 8.1 |
| C1' | 103.0 |
| C2' | 70.8 |
| C3' | 70.7 |
| C4' | 72.2 |
| C5' | 69.3 |
| C6' | 16.5 |

TABLE 3

$^1$H NMR Data for 3-O-rhamnosyl-6-deoxyerythronolide B

| Proton | $\delta_H$ | multiplicity | coupling |
|---|---|---|---|
| 2-H | 2.90 | m | |
| 3-H | 3.69 | m | |
| 4-H | 1.66 | m | |

TABLE 3-continued

¹H NMR Data for 3-O-rhamnosyl-6-deoxyerythronolide B

| Proton | $\delta_H$ | multiplicity | coupling |
|---|---|---|---|
| 5-H | 3.52 | d | 8.7 |
| 6-H | 1.63 | m | |
| 7-$H_a$ | 1.89 | m | |
| 7-$H_b$ | 0.96 | m | |
| 8-H | 2.68 | m | |
| 10-H | 2.89 | m | |
| 11-H | 3.75 | dd | 10.0, 1.8 |
| 12-H | 1.69 | m | |
| 13-H | 5.25 | dd | 9.1, 4.5 |
| 14-$H_a$ | 1.78 | m | |
| 14-$H_b$ | 1.53 | m | |
| 15-$H_3$ | 0.92 | dd | 9.4, 9.4 |
| 16-$H_3$ | 1.97 | d | 6.8 |
| 17-$H_3$ | 1.07 | d | 6.9 |
| 18-$H_3$ | 1.17 | d | 6.8 |
| 19-$H_3$ | 1.11 | d | 6.6 |
| 20-$H_3$ | 1.24 | d | 6.9 |
| 21-$H_3$ | 0.91 | d | 7.0 |
| 1'-H | 4.79 | d | 1.6 |
| 2'-H | 3.97 | dd | 3.2, 1.8 |
| 3'-H | 3.61 | dd | 9.6, 3.2 |
| 4'-H | 3.42 | dd | 9.6, 9.6 |
| 5'-H | 3.69 | dq | 9.6, 6.2 |
| 6'$H_3$ | 1.28 | d | 6.2 |

TABLE 4

¹³C NMR Data for 3-O-rhamnosyl-6-deoxyerythronolide B

| Carbon | $\delta_c$ |
|---|---|
| C1 | 177.0 |
| C2 | 42.6 |
| C3 | 83.1 |
| C4 | 41.5 |
| C5 | 76.4 |
| C6 | 36.2 |
| C7 | 33.6 |
| C8 | 44.4 |
| C9 | 213.3 |
| C10 | 44.9 |
| C11 | 70.0 |
| C12 | 40.9 |
| C13 | 76.0 |
| C14 | 25.2 |
| C15 | 5.9 |
| C16 | 13.8 |
| C17 | 8.5 |
| C18 | 19.5 |
| C19 | 14.8 |
| C20 | 14.1 |
| C21 | 8.3 |
| C1' | 103.0 |
| C2' | 70.6 |
| C3' | 70.8 |
| C4' | 72.2 |
| C5' | 69.4 |
| C6' | 16.6 |

Construction of Expression Plasmid for spnI,

The gene spnI was amplified by PCR using the primers SpnI1 5'-CTTCATATGAGTGAGATCGCAGTTGC-CCCCTGGTCG-3' (SEQ ID NO: 33) and SpnI2 5'-AACA-GATCTGCCGCCCTCGACGCCGAGCGCTTGCC-3' (SEQ ID NO: 34), which introduce a NdeI site at the 5' end and a BglII site at 3' end of spnI. Chromosomal DNA of *Saccharopolyspora spinosa* was used as a template. After treatment with T4 polynucleotide kinase the PCR product was cloned into SmaI-cut pUC18 and the resulting plasmid was used to transform *E. coli* DH10B. The sequence of spnI in the isolated plasmid was checked, and this plasmid was then digested using the restriction enzymes NdeI and BglII. A 1.2 kb fragment was isolated and ligated into the identically-digested vector fragment of pSG142, which introduced a C-terminal $His_6$-tag into SpnI. This final construct was named pSGSpnI (FIG. 6). Differences to the published DNA sequence accession A Y007564 were detected (FIG. 6B).

Construction of Expression Plasmid for spnK

For expression of spnK, primers SpnK1 5'-TCATCCATAT-GTCCACAACGCACGAGATCGAAACCGT-3' (SEQ ID NO: 35) and SpnK2 5'-TCTGCAGATCTCTCGTCCTC-CGCGCTGTTCACGTCGGCCA-3' (SEQ ID NO: 36) were used to amplify spnK with chromosomal DNA of *Saccharopolyspora spinosa* as a template. The 1.2 kb DNA fragment was isolated, treated with T4 polynucleotide kinase and cloned into SmaI cut pUC18. After transformation into *E. coli* DH10B the construct was isolated and the sequence of spnK was verified. After digestion with NdeI/BglII, a 1.2 kb fragment was isolated, ligated with the vector fragment of NdeI/BglII digested pSG142 and used to transform *E. coli* DH10B. Plasmid pSGSpnK was isolated (FIG. 6). A C-terminal $His_6$-tag was introduced into SpnK.

Construction of Expression Plasmid for spnH

For expression of spnH, the primers SpnH1 5'-TTCTA-GAGATCTACCACAACCTGGTATTCGTGGAGAA-3' (SEQ ID NO: 37) and SpnH2 5'-AACATATGCCCTCCCA-GAACGCGCTGTACCTGG-3' (SEQ ID NO: 38) were used to amplify spnH using chromosomal DNA of *Saccharopolyspora spinosa* as a template. The PCR fragment was isolated, treated with T4 polynucleotide kinase and cloned into SmaI cut pUC18. After transformation into *E. coli* DH10B the construct was isolated and the sequence of spnH was verified. After digestion with NdeI/BglII, a 0.9 kb fragment was isolated, ligated with the vector fragment of NdeI/BglII digested pSG142 and used to transform *E. coli* DH10B. Plasmid SGSpnH was isolated (FIG. 6).

Isolation of the Bioconversion Strains SGT2pSGSpnI, SGT2pSGSpnk and SGT2pSGSpnH

*Saccharopolyspora erythraea* SGT2 (Gaisser et al., 2000) was transformed with the plasmid constructs pSGSpnI, pSG-SpnK and pSGSpnH. The transformants were varified by isolating chromosomal DNA followed by PCR analysis. The PCR products were assessed by restriction digests and the pattern of DNA fragments for spnI, spnK and spnH was as expected (FIGS. 7, 8 and 9).

Preparation of 3-O-(2'-O-methylrhamnosyl)erythronolide B

Figure 10:
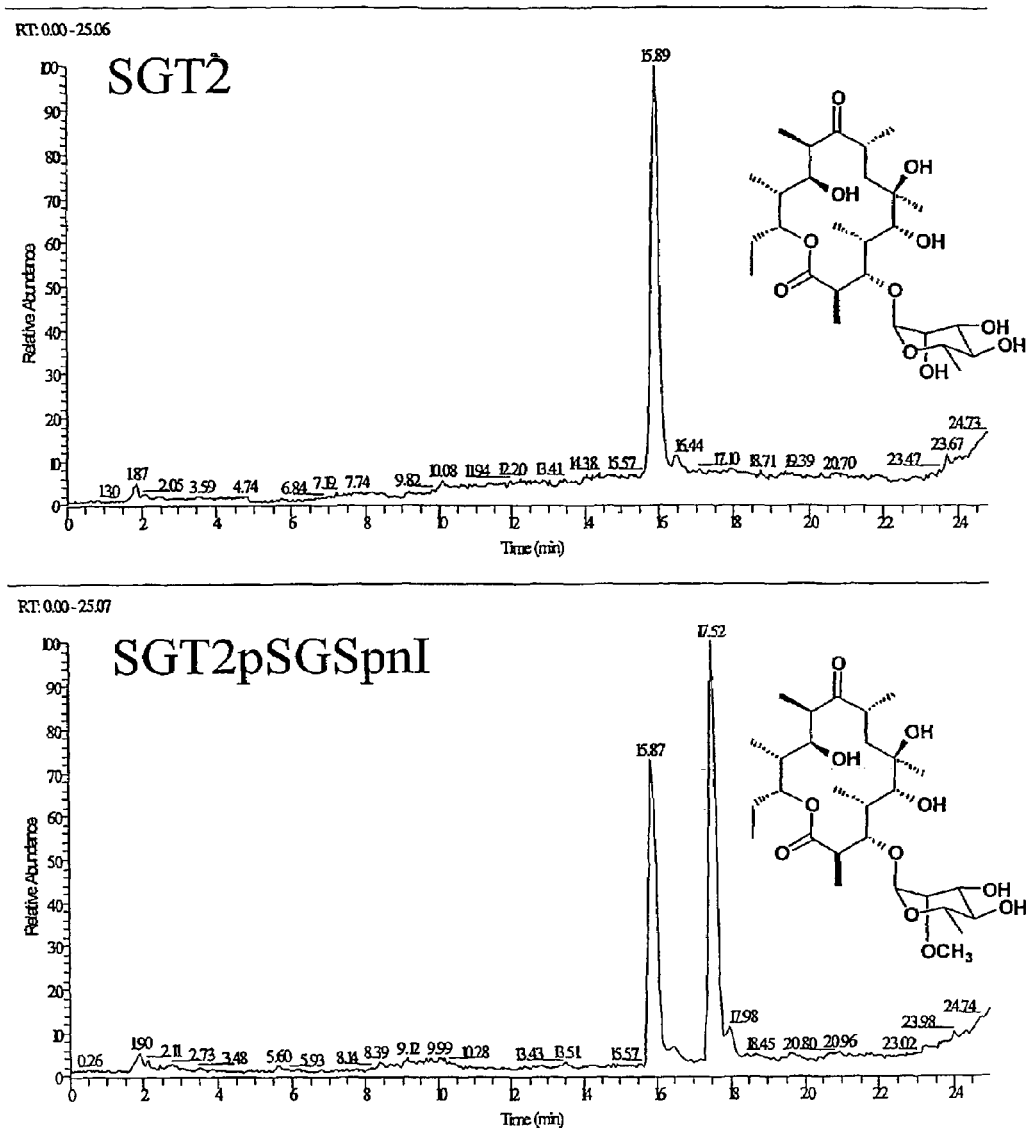
FIG. 10: Analysis of the culture supernatants of SGT2 and SGT2pSGSpnI after feeding of rhamnosyl-erythronolide B.

Feeding experiments using 3-O-rhamnosyl-erythronolide B (Gaisser et al., 2000) were carried out as described (Gaisser et al., 1997). The cultures of the strains SGT2 and SGT2pSGSpnI, were fed with 3-O-rhamnosyl-erythronolide B, incubated at 30° C. for 3 to 5 days and analysed using electrospray mass spectrometry (FIG. 10). A novel peak was visible in supernatants of SGT2pSGSpnI with a retention time of 17.5 minutes and m/z 545 ([M-$H_2$O]$H^+$) and m/z 585 ([M]$Na^+$).

Figure 11:
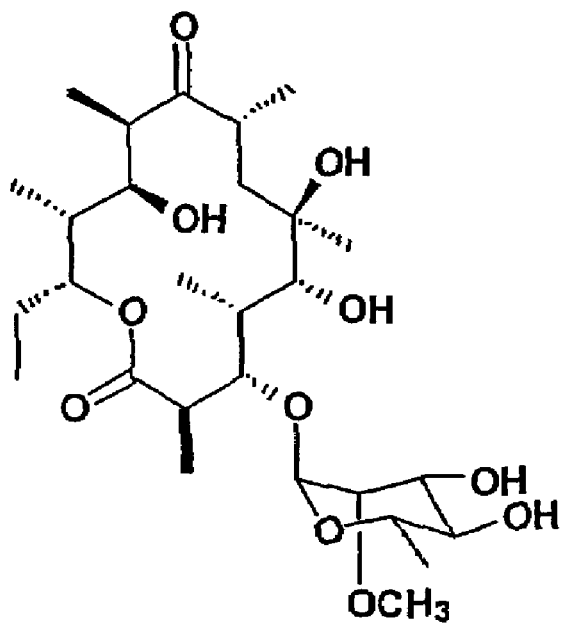
FIG. 11: Structure of 3-O-(2'-O-methylrhamnosyl)erythronolide B.

Isolation of 3-O-(2'-O-methylrhamnosyl)erythronolide B 1 l of DMpSGOleG2 culture supernatant containing 3-O-rhamnosyl-erythronolide B was filter sterilised and fed to cultures of SGT2pSGSpnI using standard microbiological techniques as described above. The new compound with the retention time of 17.5 minutes and m/z 545 ([M-$H_2$O]$H^+$) and m/z 585 ([M]$Na^+$) was isolated from the supernatant of these cultures as previously described (Gaisser et al., 2000). The novel compound was characterised as 3-O-(2'-O-methyl-rhamnosyl)-erythronolide B (FIG. 11).

TABLE 5

$^1$H and $^{13}$C NMR data for 3-O-(2'-O-methylrhamnosyl)erythronolide B

| Position | $\delta_H$ | Multiplicity | Coupling | $\delta_C$ |
|---|---|---|---|---|
| 1 | | | | 176.8 |
| 2 | 2.85 | dq | 10.2, 7.0 | 45.9 |
| 3 | 3.75 | d | 10.6 | 88.9 |
| 4 | 2.15 | m | | 37.8 |
| 5 | 3.51 | d | 3.9 | 81.8 |
| 6 | | | | 75.8 |
| 7 | 1.93 | dd | 14.5, 10.2 | 37.9 |
|   | 1.43 | dd | 14.5, 2.7 | |
| 8 | 2.71 | m | | 46.2 |
| 9 | | | | 220.8 |
| 10 | 3.04 | m | | 40.9 |
| 11 | 3.96 | dd | 10.4, 1.6 | 71.0 |
| 12 | 1.65 | m | | 41.3 |
| 13 | 5.44 | dd | 9.8, 4.7 | 76.1 |
| 14 | 1.73 | m | | 27.1 |
|   | 1.49 | m | | |
| 15 | 0.88 | dd | 7.4, 7.4 | 10.8 |
| 16 | 1.21 | d | 7.0 | 16.1 |
| 17 | 1.01 | d | 7.4 | 9.1 |
| 18 | 1.33 | s | | 26.6 |
| 19 | 1.13 | d | 7.0 | 19.0 |
| 20 | 0.96 | d | 6.7 | 9.6 |
| 21 | 0.94 | d | 7.0 | 9.7 |
| 1' | 4.93 | d | 1.4 | 100.8 |
| 2' | 3.54 | dd | 3.3, 1.7 | 82.3 |
| 3' | 3.68 | dd | 9.4, 3.2 | 72.1 |
| 4' | 3.34 | dd | 9.4, 9.4 | 73.9 |
| 5' | 3.82 | dq | 9.4, 6.3 | 70.7 |
| 6' | 1.25 | d | 6.3 | 17.9 |
| 7' | 3.44 | s | | 59.1 |

Feeding of 3-O-(2-O-methylrhamnosyl)erythronolide B

Figure 12:
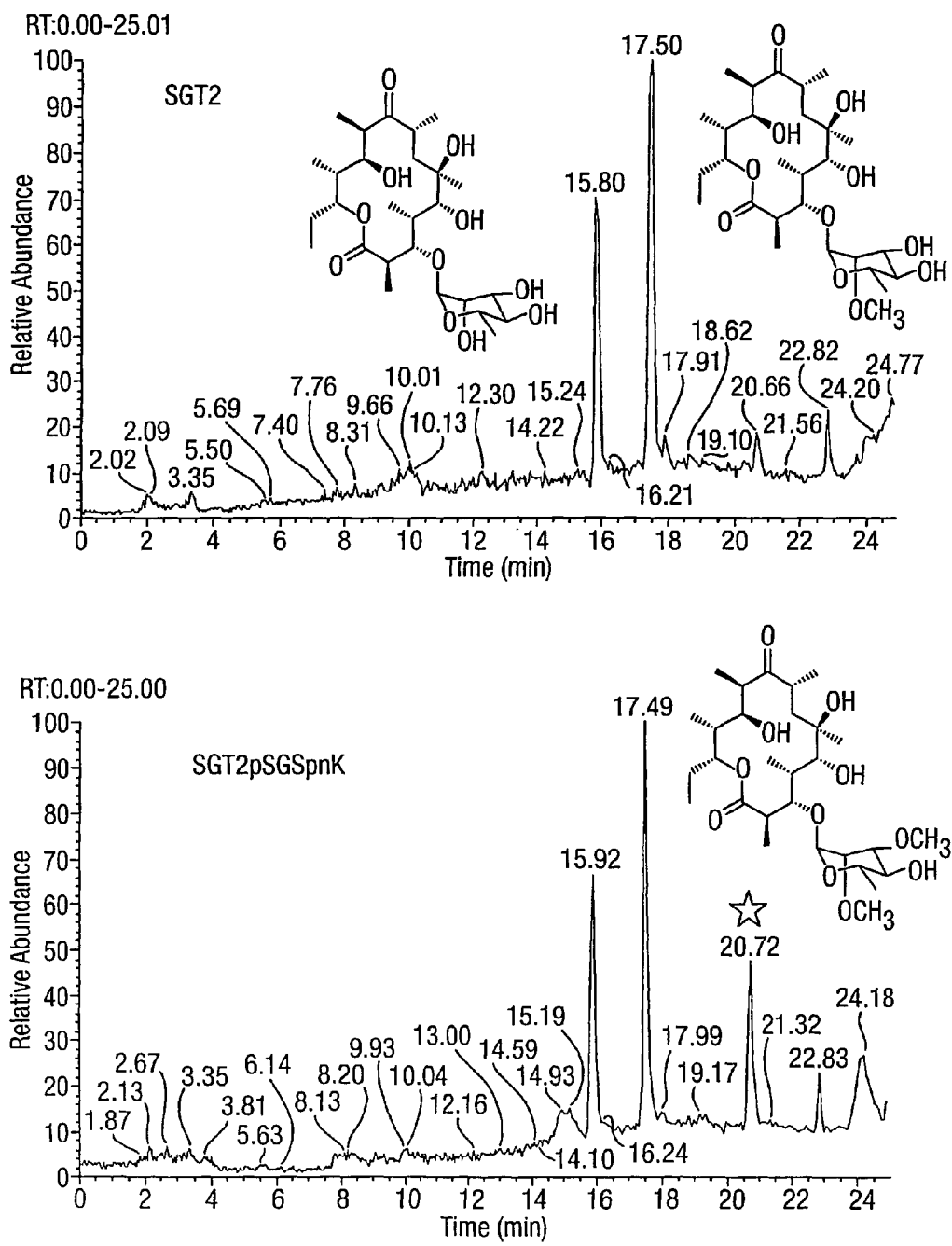
FIG. 12: Analysis of the culture supernatants of SGT2 and SGT2pSGSpnK after feeding with 3-O-(2'-O-methylrhamnosyl)erythronolide B.

3-O-rhamnosyl-erythronolide B was fed to cultures of SGT2pSGSpnI followed by an incubation at 30° C. The supernatants containing 3-O-(2'-O-methylrhamnosyl)erythronolide B were centrifuged, filter sterilised and added to cultures of the strains SGT2 and SGT2pSGSpnK using standard microbiological techniques. After incubation at 30° C. for several days the supernatants were analysed by electrospray mass spectrometry (FIG. 12). A new peak with a retention time of 20.7 minutes and m/z of 559 ([M-H$_2$O]H$^+$) and m/z of 599 ([M]Na$^+$) was detected which indicates the presence of 3-O-(2',3'-bis-O-methylrhamnosyl-)erythronolide B in the culture supernatant of the strain SGT2pSGSpnK. To prepare sufficient amounts of this novel compound for NMR analysis, plasmid pSGSpnIKH was isolated.

Construction of Expression Plasmid pSGSpnIKH

An expression plasmid which contains both genes, spnH and spnK, was isolated after digesting plasmid pSGSpnH with BglII and isolating the vector DNA. Plasmid pSGSpnK was digested with AflII/NheI and the 1.5 kb DNA band was isolated. Fill-in reactions were performed using the isolated DNA fragments as described in Sambrook et al., 1989 followed by ligation and transformation of E. coli DH10B. Plasmid pSGSpnHK was isolated (FIG. 13). Plasmid pSGSpnHK was digested with XbaI and the vector DNA was isolated. Plasmid pSGSpnI was digested with AflII/NheI and the 1.5 kb DNA band was isolated. Fill-in reactions were performed using the isolated DNA fragments as described in Sambrook et al., 1989 followed by ligation and transformation of E. coli DH10B. Plasmid pSGSpnIKH was isolated (FIG. 13) and S. erythraea SGT2 was transformed.

Figure 14:
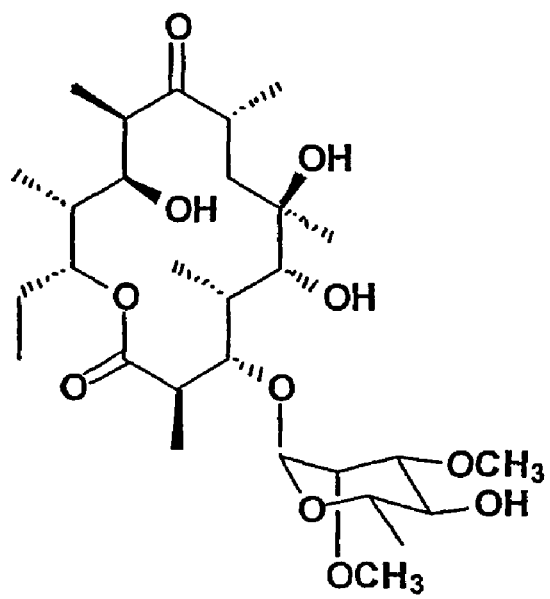
FIG. 14: Structure of 3-O-(2',3'-bis-O-methylrhamnosyl) erythronolid-e B.

Preparation of 3-O-(2',3'-bis-O-methylrhamnosyl)erythronolide B 1 l of DMpSGOleG2 culture supernatant containing 3-O-rhamnosyl-erythronolide B was filter sterilised and fed to cultures of SGT2pSGSpnIKH using standard microbiological techniques. The new compound was isolated from the supernatant of these cultures and analysed by NMR using the methods described for the preparation of 3-O-(2'-O-methylrhamnosyl)erythronolide B. The novel compound was characterised as 3-O-(2',3'-bis-O-methylrhamnosyl)erythronolide B (FIG. 14).

TABLE 6

$^1$H and $^{13}$C NMR data for 3-O-(2',3'-bis-O-methylrhamnosyl)erythronolide B

| Position | $\delta_H$ | Multiplicity | Coupling | $\delta_C$ |
|---|---|---|---|---|
| 1 | | | | 175.3 |
| 2 | 2.87 | dq | 10.2, 6.8 | 44.4 |
| 3 | 3.37 | br. d | 10.2 | 87.5 |
| 4 | 2.15 | qdd | 7.3, 3.9, 0.9 | 36.3 |
| 5 | 3.51 | d | 3.8 | 80.4 |
| 6 | | | | 74.4 |
| 7 | 1.93 | dd | 14.8, 10.4 | 36.4 |
|   | 1.44 | dd | 14.7, 2.7 | |
| 8 | 2.71 | dqd | 13.1, 7.1, 2.8 | 44.7 |
| 9 | | | | 219.3 |
| 10 | 3.04 | qd | 6.8, 1.7 | 39.4 |
| 11 | 3.97 | dd | 10.2, 1.7 | 69.6 |
| 12 | 1.65 | dqd | 10.4, 7.2, 0.9 | 39.8 |
| 13 | 5.44 | ddd | 9.8, 4.7, 0.9 | 74.7 |
| 14 | 1.72 | ddq | 14.0, 9.6, 7.3 | 25.6 |
|   | 1.50 | dqd | 14.0, 7.5, 4.6 | |
| 15 | 0.88 | dd | 7.4, 7.4 | 9.4 |
| 16 | 1.23 | d | 6.9 | 14.6 |
| 17 | 1.03 | d | 7.4 | 7.7 |
| 18 | 1.34 | s | | 25.1 |
| 19 | 1.14 | d | 7.1 | 17.5 |
| 20 | 0.96 | d | 6.8 | 8.2 |
| 21 | 0.94 | d | 7.1 | 8.2 |
| 1' | 4.95 | d | 1.7 | 99.5 |
| 2' | 3.75 | dd | 3.2, 1.9 | 76.8 |
| 3' | 3.37 | dd | 9.4, 3.0 | 80.5 |
| 4' | 3.43 | dd | 9.4, 9.4 | 71.3 |
| 5' | 3.85 | dq | 9.4, 6.4 | 69.3 |
| 6' | 1.26 | d | 6.2 | 16.5 |
| 7' | 3.45 | s | | 57.6 |
| 8' | 3.48 | s | | 56.5 |

Figure 15:
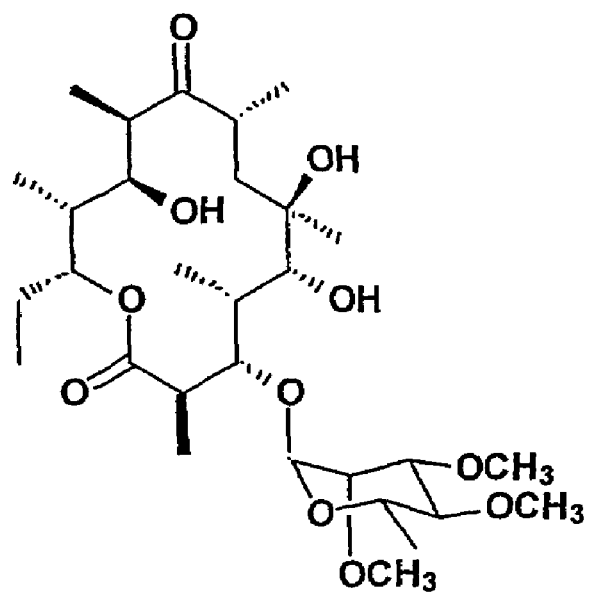
FIG. 15: Structure of 3-O-(2',3',4'-tris-O-methylrhamnosyl)erythron-olide B.

A small peak with m/z 613 was detected and the MS/MS analysis indicated that this peak represented 3-O-(2',3',4'-tris-O-methylrhamnosyl-)erythronolide B (FIG. 15).

Formation of 3-O-rhamnosylerythromycins and 3-O-rhamnosyl-6-deoxyerythromycins

The plasmid pSGCIII was transformed into S. erythraea SGT2 cells to produce mutant strain SGT2, pSGCIII and culture broths of the transformed strain were analysed as described by Gaisser et al. (1997) and by Gaisser et al. (1988). Supernatants from culture broths of S. erythraea mutant DM (pSGOLEG2) containing 3-O-rhamnosyl-erythronolide B were fed to SGT2pSGCIII cells. Analysis of the supernants using electrospray mass spectrometry, revealed the presence of a new peak at m/z 706 corresponding to 3-O-rhamnosyl-erythromycin D.

Both compounds were isolated using a gene cassette approach as described below.

Isolation of 3-O-(2'-O-methylrhamnosyl)erythromycin D 1 l of DMpSGOleG2 culture supernatant which contained 3-O-rhamnosyl-erythronolide B was filter sterilised and fed to cultures of SGT2pSGSpnI using standard microbiological techniques. The culture supernatant was analysed for 3-O-(2'-

O-methylrhamnosyl)erythronolide B and extracted as described in Materials and Methods. The crude extract was dissolved in 1 ml methanol and added to cultures of SGT2pSGeryCIII followed by an incubation at 30° C. for four days. The supernatant was analysed and a major peak at m/z 720 was detected. The novel compound was analysed using the same methods as described for the preparation of 3-O-(2'-O-methylrhamnosyl)erythronolide B. The novel compound was identified as 3-O-(2'-O-methylrhamnosyl) erythromycin D (FIG. 16B).

TABLE 7

$^{1}$H and $^{13}$C NMR data for 3-O-(2'-O-methylrhamnosyl)erythromycin D

| Position | $\delta_H$ | Multiplicity | Coupling | $\delta_C$ |
|---|---|---|---|---|
| 1 | | | | 175.9 |
| 2 | 2.93 | dq | 9.4, 7.3 | 44.6 |
| 3 | 4.19 | d | 9.0 | 82.1 |
| 4 | 2.16 | m | | 39.4 |
| 5 | 3.59 | overlaps with 2' | | 83.7 |
| 6 | | | | 73.8 |
| 7 | 1.99 | dd | 14.9, 8.5 | 37.7 |
|   | 1.54 | dd | 14.9, 4.7 | |
| 8 | 2.80 | m | | 42.8 |
| 9 | | | | 218.7 |
| 10 | 2.98 | qd | 6.8, 1.7 | 40.4 |
| 11 | 3.99 | dd | 10.2, 1.3 | 69.2 |
| 12 | 1.65 | dq | 9.8, 7.3 | 40.1 |
| 13 | 5.35 | ddd | 9.4, 4.7, 0.9 | 74.8 |
| 14 | 1.74 | ddq | 14.1, 9.4, 7.3 | 25.2 |
|    | 1.51 | dqd | 14.1, 7.3, 4.7 | |
| 15 | 0.89 | dd | 7.3, 7.3 | 9.2 |
| 16 | 1.25 | d | 6.8 | 14.8 |
| 17 | 1.12 | d | 7.3 | 8.3 |
| 18 | 1.42 | s | | 26.1 |
| 19 | 1.12 | d | 6.8 | 8.3 |
| 20 | 0.97 | d | 6.8 | 7.6 |
| 21 | 0.93 | d | 7.3 | 8.2 |
| 1' | 5.01 | d | 1.3 | 98.0 |
| 2' | 3.59 | overlaps with 5 | | 80.6 |
| 3' | 3.71 | dd | 9.4, 3.4 | 70.6 |
| 4' | 3.40 | dd | 9.4, 9.4 | 72.1 |
| 5' | 3.75 | dq | 9.4, 6.0 | 69.8 |
| 6' | 1.32 | d | 6.4 | 17.3 |
| 7' | 3.46 | s | | 57.6 |
| 1" | 4.38 | d | 7.3 | 103.0 |
| 2" | 3.27 | dd | 10.7, 7.3 | 70.7 |
| 3" | 2.80 | m | | 63.9 |
| 4" | 1.77 | m | | 30.2 |
|    | 1.28 | m | | |
| 5" | 3.75 | dq | 9.0, 6.0 | 67.7 |
| 6" | 1.20 | d | 6.0 | 20.2 |
| 7" | 2.43 | s | | 38.9 |

Bioactivity of 3-O-(2'-O-methylrhamnosyl)erythromycin D

Figure 17:
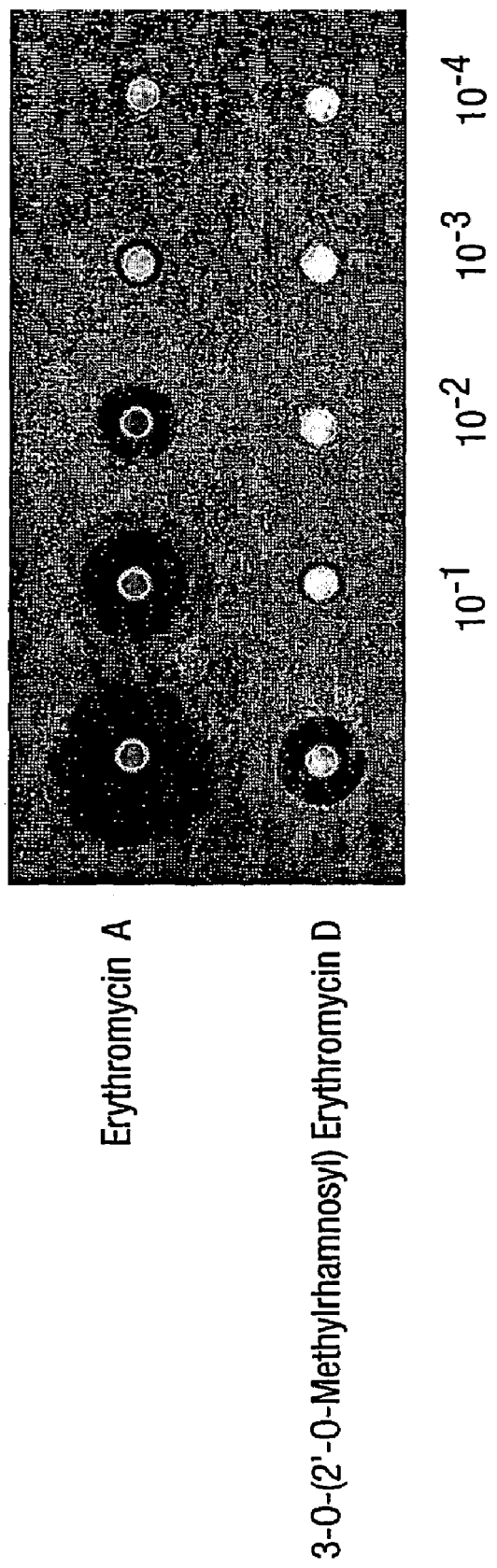
FIG. 17: Bioassay of 3-O-(2'-O-methylrhamnosyl)erythromycin D and erythromycin A.

*Bacillus subtilis* ATCC 6633 was used in bioassays as described previously (Gaisser et al., 1998). To assess the bioactivity of 3-O-(2'-O-methylrhamnosyl)erythromycin D, 1.1 mg aliquots of erythromycin A (Sigma) and of 3-O-(2'-O-methylrhamnosyl)erythromycin D were each dissolved in 200 µl of methanol, and series of 10-fold dilutions were prepared. Filter discs were soaked with 10 µl of these solutions and placed on 2.times.TY plates overlaid with agar inoculated with an overnight culture of *B. subtilis* as described previously (Gaisser et al., 1997). The development of zones of inhibition in the *B. subtilis* lawn was assessed. The size of the halos in the bacterial lawn around the filter discs indicated that the bioactivity of 3-O-(2'-O-methylrhamnosyl) erythro-mycin D was about 100-fold less compared to erythromycin A with *Bacillus subtilis* ATCC 6633 as indicator strain (FIG. 17).

Isolation of 3-O-(2',3'-bis-O-methylrhamnosyl)erythromycin D 1 l of DMpSGOleg2 culture supernatant which contained 3-O-rhamnosyl-erythronolide B was filter sterilised and fed to cultures of SGT2pSGSpnHKI using standard microbiological techniques. The culture supernatant was analysed for 3-O-(2',3'-bis-O-methylrhamnosyl)erythronoli-de B and extracted as described in Materials and Methods. The fraction which contained 3-O-(2',3'-bis-O-methylrhamnosyl)erythronolide B was isolated. The dried extract of 3-O-(2',3'-bis-O-methylrhamnosyl)erythrono-lide B was dissolved in 1 ml methanol and added to cultures of SGT2pSGeryCIII followed by an incubation at 30° C. for four days. The supernatant was analysed. A major peak with m/z of 734 was detected. The compound was isolated and analysed using the methods described for the preparation of 3-O-(2'-O-methylrhamnosyl)erythronolide B. The novel compound was identified as 3-O-(2',3'-bis-O-methylrhamnosyl)erythromycin D (FIG. 16C).

TABLE 8

$^{1}$H and $^{13}$C NMR data for 3-O-(2', 3'-bis-O-methylrhamnosyl)erythromycin D

| Position | $\delta_H$ | Multiplicity | Coupling | $\delta_C$ |
|---|---|---|---|---|
| 1 | | | | 176.0 |
| 2 | 2.93 | dq | 9.4, 6.8 | 44.8 |
| 3 | 4.20 | dd | 9.4, 0.9 | 82.5 |
| 4 | 2.18 | dq | 7.7, 7.3 | 39.2 |
| 5 | 3.61 | d | 7.7 | 84.0 |
| 6 | | | | 74.2 |
| 7 | 1.99 | dd | 14.9, 8.5 | 37.8 |
|   | 1.52 | dd | 14.9, 4.7 | |
| 8 | 2.81 | m | | 42.8 |
| 9 | | | | 219.2 |
| 10 | 2.96 | qd | 6.8, 1.7 | 40.5 |
| 11 | 3.99 | dd | 10.2, 1.7 | 69.4 |
| 12 | 1.65 | dqd | 10.2, 7.3, 0.9 | 39.9 |
| 13 | 5.36 | ddd | 9.4, 4.7, 1.3 | 74.9 |
| 14 | 1.74 | ddq | 14.1, 9.4, 7.3 | 25.4 |
|    | 1.50 | dqd | 14.1, 7.3, 4.7 | |
| 15 | 0.90 | dd | 7.3, 7.3 | 9.3 |
| 16 | 1.27 | d | 7.3 | 14.8 |
| 17 | 1.13 | d | 7.3 | 8.4 |
| 18 | 1.43 | s | | 26.3 |
| 19 | 1.11 | d | 6.8 | 17.2 |
| 20 | 0.97 | d | 6.8 | 7.7 |
| 21 | 0.92 | d | 7.3 | 8.3 |
| 1' | 5.02 | d | 2.1 | 98.4 |
| 2' | 3.80 | dd | 2.6, 2.6 | 76.6 |
| 3' | 3.39 | dd | 9.0, 3.0 | 80.4 |
| 4' | 3.49 | dd | 9.0, 9.0 | 70.9 |
| 5' | 3.75 | dq | 9.0, 6.4 | 70.2 |
| 6' | 1.32 | d | 6.4 | 17.2 |
| 7' | 3.49 | s | | 57.5 |
| 8' | 3.46 | s | | 56.3 |
| 1" | 4.44 | d | 7.3 | 102.5 |
| 2" | 3.37 | dd | 7.3, 3.4 | 69.9 |
| 3" | 3.21 | m | | 65.0 |
| 4" | 1.91 | m | | 29.9 |
|    | 1.42 | m | | |
| 5" | 3.75 | m | | 70.0 |
| 6" | 1.25 | d | 6.4 | 20.1 |
| 7" | 2.68 | s | | 38.5 |

Construction of the *Saccharopolyspora erythraea* Strain SGT 3 (ΔeryCIIIΔeryBVΔeryBVI)

To prevent contamination with mycarosyl-erythronolide B in feeding assays, the *Saccharopolyspora erythraea* strain SGT3 (ΔeryCIIIΔeryBVΔeryBVI) was isolated using plasmid pHol (Gaisser et al., 1997). The transformation of the *S. erythraea* strain DM and the isolation of the mutant SGT3 were performed as described (Gaisser et al., 1997). To investigate the thiostrepton sensitive mutants no 31, 33, 34 and 25, chromosomal DNA was analysed using PCR analysis. Chromosomal DNA was subjected to PCR using the primers as described earlier (Gaisser et al., 1997). The expected 360 bp fragment was amplified from wild type DNA and two bands of roughly 100 and 300 bp of size were detected after PstI restriction digest. In samples with the chromosomal DNA of SGT3 as a template, a 300 bp fragment was amplified which was found to be resistant to digestion by PstI. This result indicates the introduction of a 60 bp deletion in eryBVI into the genome of SGT3. This strain is used as background for the expression of the gene cassettes described below.

Construction of Expression Plasmid for oleP

For expression of oleP, the primers OleP1 5'-CTCCAG-CAAAGGACACACCCATATGACCGATACGCACA-3' (SEQ ID NO: 39) and OleP2 5'-CGGCAGATCTGCCGGC-CGTCACCAGGAGACGATCTGG-3' (SEQ ID NO: 40) were used to amplify oleP using plasmid 3gh2 as a template. The PCR fragment was isolated, treated with T4 polynucleotide kinase and cloned into SamI cut pUC18. After transformation into *E. coli* DH10B the construct was isolated and the sequence of oleP was verified. After digestion with NdeI/BglII, a 1.3 kb fragment was isolated, ligated with the vector fragment of NdeI/BglII digested pSG142 and used to transform *E. coli* DH10B. Plasmid pSGOleP was isolated.

Feeding of Erythronolides to Strain SGT2pSGOleP

*Saccharopolyspora erythraea* SGT2 (Gaisser et al., 2000) was transformed with the plasmid construct pSGOleP as described in Materials and Methods. The transformants were verified by isolating chromosomal DNA followed by PCR analysis. Feeding experiments using 6-deoxyerythronolide B, erythronolide B, 3-O-mycarosyl-erythronolide B, 3-O-rhamnosyl-erythronolide B (Gaisser et al., 2000), and erythromycin A were carried out as described (Gaisser et al., 1997). The cultures of the strains SGT2 and SGT2pSGOleP were fed with these compounds, incubated at 30° C. for 3 to 5 days and analysed using electrospray mass spectrometry. Novel peaks were visible in supernatants of SGT2pSGOleP fed with 6-deoxyerythronolide B (m/z 434 [M]NH$_4^+$), 3-O-mycarosyl-erythronolide B (m/z 578 [M]NH$_4^+$ and m/z 580 [M]NH$_4^+$) and 3-O-rhamnosyl-erythronolide B (m/z 580 [M]NH$_4^+$ and m/z 582 [M]NH$_4^+$). Novel peaks could not be detected in supernatants that contained erythronolide B and erythromycin A. MS/MS analysis of these new compounds indicated the presence of 8,8a-epoxy- or 8,8a-dihydroxy derivatives of 6-deoxyerythronolide B, 3-O-mycarosyl-erythronolide B, and 3-O-rhamnosyl-erythronolide B.

Preparation of 8a-hydroxy-3-O-mycarosyl Erythronolide B and $^8$-epoxy-$^3$-O-mycarosyl Erythronolide B 2.5 l of culture supernatant of SGT2pSGOleP fed with 60 mg of 3-O-mycarosyl-erythronolide B were grown and the novel compounds were isolated using methods described in Materials and Methods. The structures of these compounds were confirmed by NMR analysis using the methods described for the preparation of 3-O-(2'-O-methylrhamnosyl) erythronolide B. The 3-O-mycarosyl erythronolide B derived compounds were identified as 8a-hydroxy-3-O-mycarosyl erythronolide B and 8,8a-epoxy-3-O-mycarosyl erythronolide B (FIG. 21).

TABLE 9

$^1$H NMR Data for 8a-hydroxy-3-O-mycarosyl erythronolide B

| Proton | $\delta_H$ | multiplicity | coupling (Hz) |
|---|---|---|---|
| 2-H | 2.87 | dq | 10.1, 7.0 |
| 3-H | 3.75 | dd | 10.0, 1.2 |
| 4-H | 2.15 | m | |
| 5-H | 3.55 | d | 3.5 |
| 7-H$_a$ | 1.49 | dd | 14.6, 3.0 |
| 7-H$_b$ | 1.84 | dd | 14.6, 10.3 |
| 8-H | 2.83 | m | |
| 8a-H$_a$ | 3.66 | dd | 11.0, 6.0 |
| 8a-H$_b$ | 3.71 | dd | 11.0, 9.1 |
| 10-H | 3.07 | qd | 6.9, 1.8 |
| 11-H | 3.93 | dd | 10.2, 1.8 |
| 12-H | 1.66 | m | |
| 13-H | 5.44 | ddd | 9.5, 4.9, 1.2 |
| 14-H$_a$ | 1.49 | dqd | 16.9, 7.3, 4.8 |
| 14-H$_b$ | 1.73 | ddq | 16.9, 9.5, 7.3 |
| 15-H$_3$ | 0.88 | d | 7.3 |
| 16-H$_3$ | 1.18 | d | 6.9 |
| 17-H$_3$ | 1.02 | d | 7.3 |
| 18-H$_3$ | 1.33 | s | |
| 19-H$_3$ | 0.96 | d | 6.8 |
| 20-H$_3$ | 0.94 | d | 7.1 |
| 1'-H | 5.02 | dd | 3.9, 1.1 |
| 2'-H$_a$ | 1.84 | dd | 14.5, 4.2 |
| 2'-H$_b$ | 2.08 | dd | 14.5, 1.2 |
| 4'-H | 2.98 | d | 9.7 |
| 5'-H | 4.06 | dq | 9.8, 6.2 |
| 6'-H$_3$ | 1.28 | d | 6.2 |
| 7'-H$_3$ | 1.22 | s | |

TABLE 10

$^{13}$C NMR Data for 8a-hydroxy-3-O-mycarosyl erythronolide B

| Carbon | $\delta_C$ |
|---|---|
| 1 | 175.3 |
| 2 | 44.4 |
| 3 | 86.4 |
| 4 | 36.3 |
| 5 | 80.1 |
| 6 | 74.4 |
| 7 | 31.0 |
| 8 | 52.9 |
| 8a | 63.5 |
| 9 | 217.3 |
| 10 | 40.6 |
| 11 | 69.6 |
| 12 | 39.6 |
| 13 | 74.6 |
| 14 | 25.4 |
| 15 | 9.3 |
| 16 | 14.4 |
| 17 | 7.5 |
| 18 | 24.7 |
| 19 | 7.2 |
| 20 | 8.2 |
| 1' | 99.2 |
| 2' | 40.8 |
| 3' | 69.5 |
| 4' | 76.3 |
| 5' | 65.5 |
| 6' | 16.8 |
| 7' | 24.7 |

TABLE 11

$^1$H NMR Data for 8,8a-epoxy-3-O-mycarosyl erythronolide B

| Proton | $\delta_H$ | multiplicity | coupling (Hz) |
|---|---|---|---|
| 2-H | 2.89 | dq | 10.4, 7.0 |
| 3-H | 3.74 | dd | 10.4, 1.3 |
| 4-H | 2.21 | m | |
| 5-H | 3.48 | d | 3.4 |
| 7-H$_a$ | 1.50 | d | 14.9 |
| 7-H$_b$ | 2.62 | d | 14.9 |
| 8a-H$_a$ | 2.52 | d | 5.5 |
| 8a-H$_b$ | 2.67 | d | 5.5 |
| 10-H | 3.12 | qd | 6.8, 1.9 |
| 11-H | 4.22 | dd | 10.4, 1.9 |
| 12-H | 1.67 | qd | 7.0, 1.3 |
| 13-H | 5.47 | ddd | 9.8, 4.7, 1.3 |
| 14-H$_a$ | 1.51 | m | |
| 14-H$_b$ | 1.75 | m | |
| 15-H$_3$ | 0.88 | dd | 7.3, 7.3 |
| 16-H$_3$ | 1.20 | d | 7.3 |
| 17-H$_3$ | 1.03 | d | 7.3 |
| 18-H$_3$ | 1.43 | s | |
| 19-H$_3$ | 0.97 | d | 6.8 |
| 20-H$_3$ | 0.95 | d | 7.0 |
| 1'-H | 5.02 | dd | 4.2, 1.3 |
| 2'-H$_a$ | 1.84 | dd | 14.5, 4.3 |
| 2'-H$_b$ | 2.08 | dd | 14.5, 1.3 |
| 4'-H | 2.98 | d | 9.8 |
| 5'-H | 4.06 | dq | 9.8, 6.2 |
| 6'-H$_3$ | 1.27 | d | 6.2 |
| 7'-H$_3$ | 1.22 | s | |

TABLE 12

$^{13}$C NMR Data for 8,8a-epoxy-3-O-mycarosyl erythronolide B

| Carbon | $\delta C$ |
|---|---|
| 1 | 175.4 |
| 2 | 44.4 |
| 3 | 86.7 |
| 4 | 36.2 |
| 5 | 81.0 |
| 6 | 75.2 |
| 7 | 35.0 |
| 8 | 62.5 |
| 8a | 50.0 |
| 9 | 210.5 |
| 10 | 44.1 |
| 11 | 68.9 |
| 12 | 39.5 |
| 13 | 74.6 |
| 14 | 25.5 |
| 15 | 9.4 |
| 16 | 14.6 |
| 17 | 7.5 |
| 18 | 25.9 |
| 19 | 7.7 |
| 20 | 8.2 |
| 1' | 99.4 |
| 2' | 40.7 |
| 3' | 69.5 |
| 4' | 76.2 |
| 5' | 65.3 |
| 6' | 16.8 |
| 7' | 24.6 |

Preparation of 8,8a-dehydro-6-deoxyerythronolide B and 8-hydroxy-6-deoxyerythronolide B Plasmid pSGOleP was used to transform the 6-deoxyerythronolide B producer strain *S. erythraea* SGT1 (ΔeryBV, ΔeryCIII, ΔeryF) as described in Materials and Methods. The transformants were verified by isolating chromosomal DNA followed by PCR analysis. Cultures of SGT1 and SGT1pSGOleP were grown as described previously (Gaisser et al., 2000) and the supernatants were analysed using electrospray mass spectrometry as described in Materials and Methods. Two major compounds in the supernatant were purified and analysed using NMR techniques as described for the preparation of 3-O-(2'-O-methylrhamnosyl)-erythronolide B. The product with m/z 401 [M-H$_2$O]H$^+$ was identified as the 8,8a-dihydroxy derivative of 6-deoxyerythronolide B recently disclosed (Shah et al., 2000). The compound with m/z of 385 [M]H$^+$ was confirmed as 8,8a-dehydro-6-deoxyerythronolide B (FIG. 22). The structure of a further, minor compound of the culture supernatant was identified as 8-hydroxy-6-deoxyerythronolide B (FIG. 22).

TABLE 13

$^1$H NMR Data for 8,8a-dehydro-6-deoxyerythronolide B

| Proton | δH | multiplicity | coupling (Hz) |
|---|---|---|---|
| 2-H | 2.70 | dq | 9.8, 6.8 |
| 3-H | 3.55 | ovrlp | |
| 4-H | 1.69 | ovrlp | |
| 5-H | 3.55 | ovrlp | |
| 6-H | 1.91 | m | |
| 7-H$_a$ | 2.11 | dd | 17.1, 7.7 |
| 7-H$_b$ | 2.45 | dd | 17.1, 3.8 |
| 8a-H$_a$ | 5.38 | s | |
| 8a-H$_b$ | 5.66 | s | |
| 10-H | 3.23 | dq | 6.8, 1.7 |
| 11-H | 3.60 | dd | 10.2, 1.7 |
| 12-H | 1.70 | ovrlp | |
| 13-H | 5.24 | ddd | 9.4, 4.7, 2.1 |
| 14-H$_a$ | 1.52 | ddq | 14.1, 9.4, 7.3 |
| 14-H$_b$ | 1.77 | dqd | 14.1, 7.3, 4.7 |
| 15-H$_3$ | 0.90 | dd | 7.3, 7.3 |
| 16-H$_3$ | 1.18 | d | 6.8 |
| 17-H$_3$ | 1.03 | d | 6.8 |
| 18-H$_3$ | 1.12 | d | 6.8 |
| 19-H$_3$ | 0.97 | d | 6.8 |
| 20-H$_3$ | 0.96 | d | 7.3 |

TABLE 13

$^{13}$C NMR Data for 8,8a-dehydro-6-deoxyerythronolide B

| Carbon | $\delta_C$ |
|---|---|
| 1 | 178.7 |
| 2 | 45.3 |
| 3 | 75.5 |
| 4 | 42.3 |
| 5 | 77.7 |
| 6 | 35.9 |
| 7 | 33.2 |
| 8 | 150.4 |
| 8a | 120.6 |
| 9 | 208.8 |
| 10 | 44.9 |
| 11 | 71.9 |
| 12 | 42.1 |
| 13 | 76.9 |
| 14 | 26.7 |
| 15 | 10.9 |
| 16 | 15.2 |
| 17 | 8.9 |
| 18 | 20.2 |
| 19 | 6.5 |
| 20 | 10.0 |

TABLE 14

$^1$H NMR Data for 8-hydroxy-6-deoxyerythronolide B (CDCl$_3$)

| Proton | δH | multiplicity | coupling (Hz) |
|---|---|---|---|
| 2-H | 2.63 | dq | 10.2, 6.8 |
| 3-H | 3.61 | dd | 10.2, 3.0 |
| 4-H | 1.56 | m | |
| 5-H | 3.53 | br · s | |
| 6-H | 1.40 | m | |
| 7-H$_a$ | 1.74 | m | |
| 7-H$_b$ | 1.96 | dd | 14.9, 3.4 |
| 10-H | 3.05 | qd | 6.8, 0.9 |
| 11-H | 3.45 | d | 9.8 |
| 12-H | 1.72 | m | |
| 13-H | 5.45 | ddd | 9.4, 4.7, 0.9 |
| 14-H$_a$ | 1.50 | m | |
| 14-H$_b$ | 1.72 | m | |
| 15-H$_3$ | 0.90 | t | 7.3, 7.3 |
| 16-H$_3$ | 1.25 | d | 6.8 |
| 17-H$_3$ | 1.05 | d | 7.3 |
| 18-H$_3$ | 1.15 | d | 6.8 |
| 19-H$_3$ | 1.42 | s | |
| 20-H$_3$ | 1.11 | d | 6.8 |
| 21-H$_3$ | 0.90 | d | 7.3 |

TABLE 15

$^{13}$C NMR Data for 8-hydroxy-6-deoxyerythronolide B (CDCl$_3$)

| Carbon | δ$_x$ |
|---|---|
| 1 | 175.6 |
| 2 | 43.9 |
| 3 | 77.8 |
| 4 | 41.3 |
| 5 | 79.4 |
| 6 | 36.0 |
| 7 | 39.2 |
| 8 | 79.7 |
| 9 | 218.7 |
| 10 | 38.8 |
| 11 | 69.4 |
| 12 | 40.1 |
| 13 | 75.2 |
| 14 | 25.6 |
| 15 | 10.3 |
| 16 | 14.8 |
| 17 | 7.7 |
| 18 | 20.2 |
| 19 | 26.9 |
| 20 | 9.6 |
| 21 | 8.9 |

Strategy to Isolate Gene Cassettes

Figure 18:
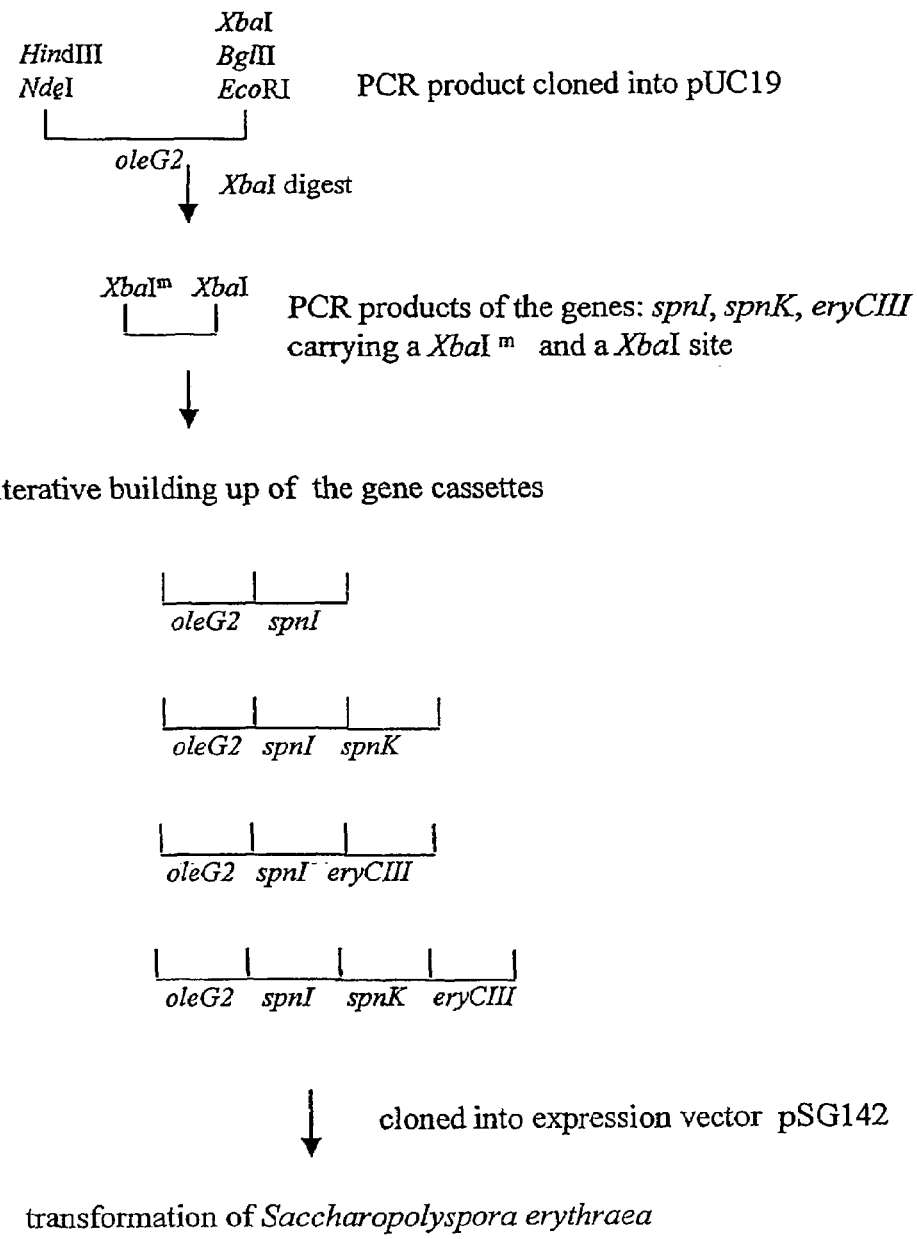
FIG. 18: Strategy to isolate gene cassettes of oleG2, spnI, spnH, spnK and eryCIII.

The strategy to prepare gene cassettes with different combinations of glycosyltransferase- and methyltransferase genes is adapted from a technique previously described (WO 077181 A2) to build gene cassettes expressed under the control of the actII-Orf4 regulator. The expression of these gene cassettes in a suitable strain background is a powerful approach to generate novel post-PKS modified polyketides in a random or directed fashion. The method is based upon the introduction of XbaI restriction sites at the 3' and 5'-end of the PCR fragments. The introduction of a XbaI site at the 5'-end of the PCR fragment which is sensitive to the Dam methylase of the strain background will protect this site from further XbaI digest. To retain the Shine Dalgarno sequence 5' of the respective gene the pSG142 derived constructs which contain these genes were used as a template. Using plasmid DNA isolated from dam⁻ host strains such as E. coli ET12567, the amplified genes were isolated as XbaI fragments. Using a host strain with an active Dam methylase such as E. coli DM10B these fragments were sequentially cloned into gene cassettes. This technique provides the means to build gene cassettes of different length and different order using the same strategy over and over again. An overview of the strategy described here and the isolated gene cassettes is depicted in FIG. 18.

The following example of this methodology was based upon the isolation of a PCR fragment of oleG2 into which a HindIII and a NdeI restriction site was introduced at the 5'-end of the fragment and a XbaI, BglII and EcoRI site at the 3'-end of the PCR fragment. This fragment was digested using the restriction enzymes HindIII and EcoRI and it was cloned into pUC19 which was digested identically. Plasmid pSGcasoleG2 was isolated. The genes spnI, spnK, spnH and eryCIII were amplified using PCR techniques. A XbaI restriction site was introduced at the 5'-end which is sensitive to methylation by the Dam methylase of the strain background. At the 3'-end a XbaI site was introduced. The pSG142 derived constructs which contain these genes were used as a template. The PCR fragments were treated with T4 polynucleotide kinase as described above and cloned into SamI cut pUC18. The DNA sequences of these clones were confirmed by sequencing analysis. After transforming the constructs into a dam⁻ strain background, the DNA was isolated and digested using XbaI. The XbaI fragments of the inserts of around 0.8-1.3 kb of size were isolated and ligated into the XbaI cut pSGcasOleG2. After building the gene cassettes in pUC19, each construct was digested using the restriction enzymes NdeI/BglII and the DNA fragment encoding the gene cassette was isolated and cloned into the NdeI/BglII digested vector DNA of pSG142. These plasmids were transformed into SGT3. The transformants were analysed as described above.

The following primers were used:

```
casoleG21
5' GGGGAAGCTTGCCGACGATGACGACGACCAC    (SEQ ID NO: 41)
CGGACGAACGCATCGATTAATTTAAG casoleG22
5' GGGGAATTTCAGATCTGGTCTAGAGGTCAGC    (SEQ ID NO: 42)
CCGCATGGUCCCGCCTCCTCGTCCGCGTCCGCCG
CT casspnI3
5' GGGTCTAGATCCGGACGAACGCATCGATTAA    (SEQ ID NO: 43)
TTAAGGAGGACAGATATGAGTGAGATCGCAGTTG
CCCC casspnI4
5' GGGGTGTAGAGGTCAGCCGCCCTCGACGCCG    (SEQ ID NO: 44)
AGCGCTTGCCGGGGCACGAACCCCGGGGCGGCAG
GCT casspnK1
5' GGGTCTAGATCCGGACGAACGCATCGATTAA    (SEQ ID NO: 45)
TTAAGGAGGACAGATATGTCCACAACGCACGAGA
TCG casspnK2
5' GGGGTCTAGAGGTCAGTCGTCCTCCGCGCTG    (SEQ ID NO: 46)
TTCACGTCGGCCAGGTGCAATATGTC caseryCIII1
5' GGGTCTAGATCCGGACGAACGCATCGATTAA    (SEQ ID NO: 47)
TTAAGGAGGACAGATATGCGCGTCGTGTTGTCCT
C caseryCIII2
5' GGGGTCTAGAGGTCATCGTGGTTCTCTCTCC    (SEQ ID NO: 48)
TGCGGCCAGTTCCTCGCA.
```

Analysis of SGT3pSGcasoleG2spnI

The clone SGT3pSGcasoleG2spnI was isolated using the approach described above. The cells were grown as described in Materials and Methods and the culture supernatant was analysed. As expected, 3-O-(2'-O-methylrhamnosyl)erythronolide B and 3-O-(2'-O-methylrhamnosyl)-6-deoxyerythronolide B were detected.

Analysis of SGT3pSGcasoleG2spnIspnK

Figure 19:
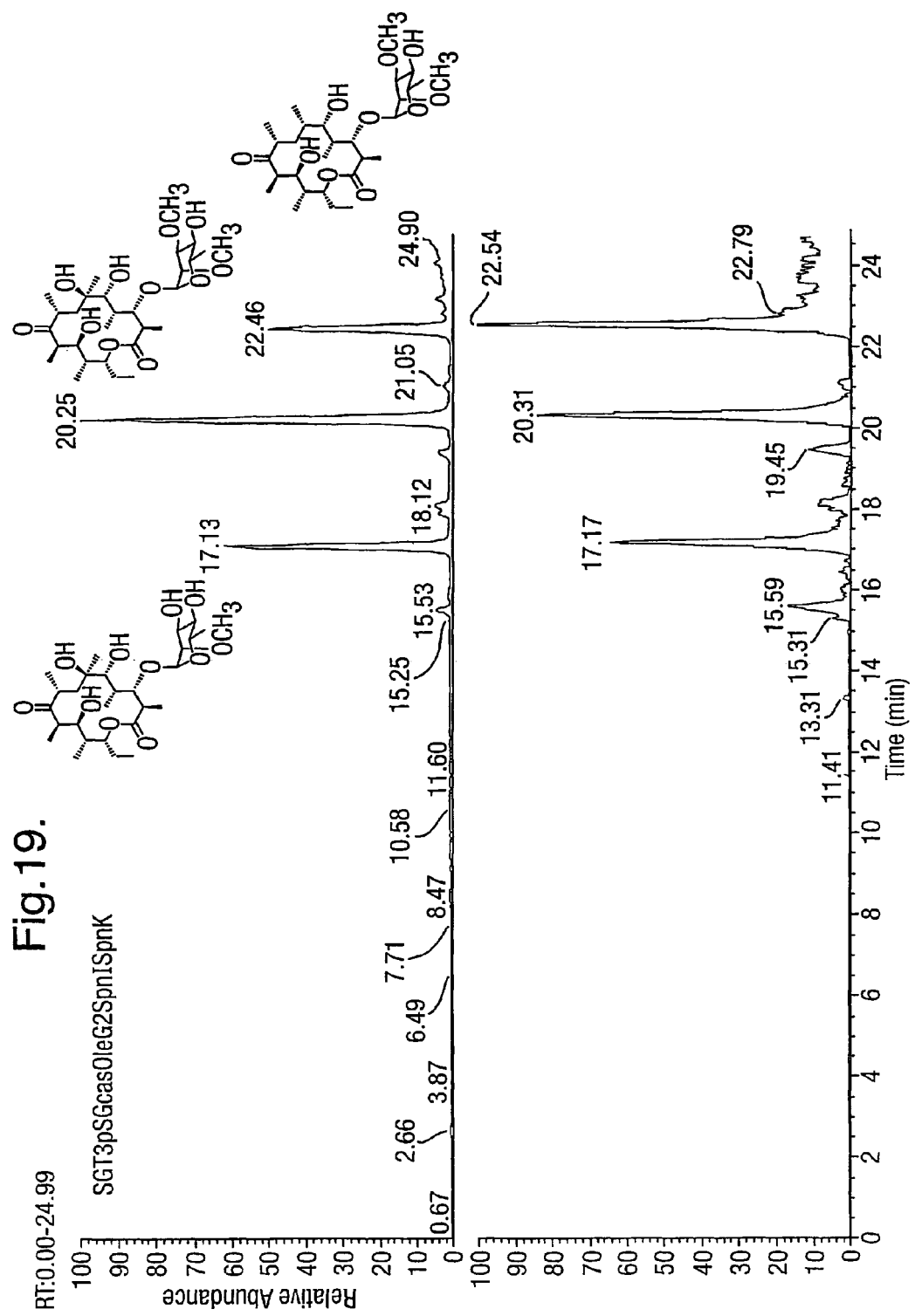
FIG. 19: Results of the analysis of the culture supernatant of SGT3pSGcasoleG2spnIspnK.

SGT3pSGcasoleG2spnIspnK was isolated using the approach described above. The cells were grown as described in Materials and Methods and the culture supernatant was analysed. As expected, 3-O-(2'-O-methylrhamnosyl)-erythronolide B and 3-O-(2',3'-bis-O-methylrhamnosyl)erythronolide B were detected (FIG. 19). The culture supernatant also contained a further novel compound which was isolated and the structure was confirmed by NMR analysis using the methods described for the preparation of 3-O-(2'-O-methylrhamnosyl)erythronolide B. The structure of the novel compound was characterised as 3-O-(2',3'-bis-O-methylrhamnosyl)-6-deoxyerythronolide B (FIG. 19).

TABLE 16

$^1$H and $^{13}$C NMR data for 3-O-(2',3'-bis-O-methylrhamnosyl)-6-dEB

| Position | δH | Multiplicity | Coupling | δ$_C$ |
|---|---|---|---|---|
| 1 | | | | 178.4 |
| 2 | 2.89 | dq | 8.1, 7.3 | 46.2 |
| 3 | 3.37 | overlap | | 84.1 |
| 4 | 1.68 | m | | 43.1 |
| 5 | 3.49 | d | 9.2 | 77.8 |
| 6 | 1.66 | m | | 37.1 |
| 7 | 1.01 | m | | 35 |
|   | 1.86 | m | | |
| 8 | 2.68 | m | | 45.8 |
| 9 | | | | 218 |
| 10 | 2.95 | qd | 6.8, 1.9 | 43.8 |
| 11 | 3.73 | dd | 10.2, 1.7 | 72.1 |
| 12 | 1.65 | m | | 42 |
| 13 | 5.25 | ddd | 9.2, 5.3, 1.3 | 77.4 |
| 14 | 1.54 | m | | 26.5 |
|    | 1.80 | m | | |
| 15 | 0.92 | dd | 7.3, 7.3 | 10.8 |
| 16 | 1.27 | d | 6.4 | 15.3 |
| 17 | 1.08 | d | 7.0 | 10 |
| 18 | 1.16 | d | 6.4 | 20.6 |
| 19 | 1.13 | d | 6.6 | 16.4 |
| 20 | 0.98 | d | 6.8 | 7.5 |
| 21 | 0.92 | d | 7.0 | 9.7 |
| 1' | 4.97 | d | 1.5 | 100.7 |
| 2' | 3.77 | overlap | | 78.1 |
| 3' | 3.33 | dd | 9.4, 3.0 | 81.8 |
| 4' | 3.42 | dd | 9.4, 9.4 | 72.8 |
| 5' | 3.67 | dq | 9.4, 6.2 | 70.9 |
| 6' | 1.25 | d | 6.0 | 18.1 |
| 7' | 3.45 | s | | 58.9 |
| 8' | 3.47 | s | | 57.9 |

Analysis of SGT3pSGoleG2spnIspnKeryCIII

SGT3pSGoleG2spnIspnKeryCIII was isolated using the methods described above. The cells were grown as described in Materials and Methods. The culture supernatants of SGT3pSGcasoleG2spnIspnKeryCIII contained only small amounts of compounds with an attached desosamine sugar residue.

Analysis of SGT3pSGoleG2spnIspnKeryCIIIhis

Figure 20:
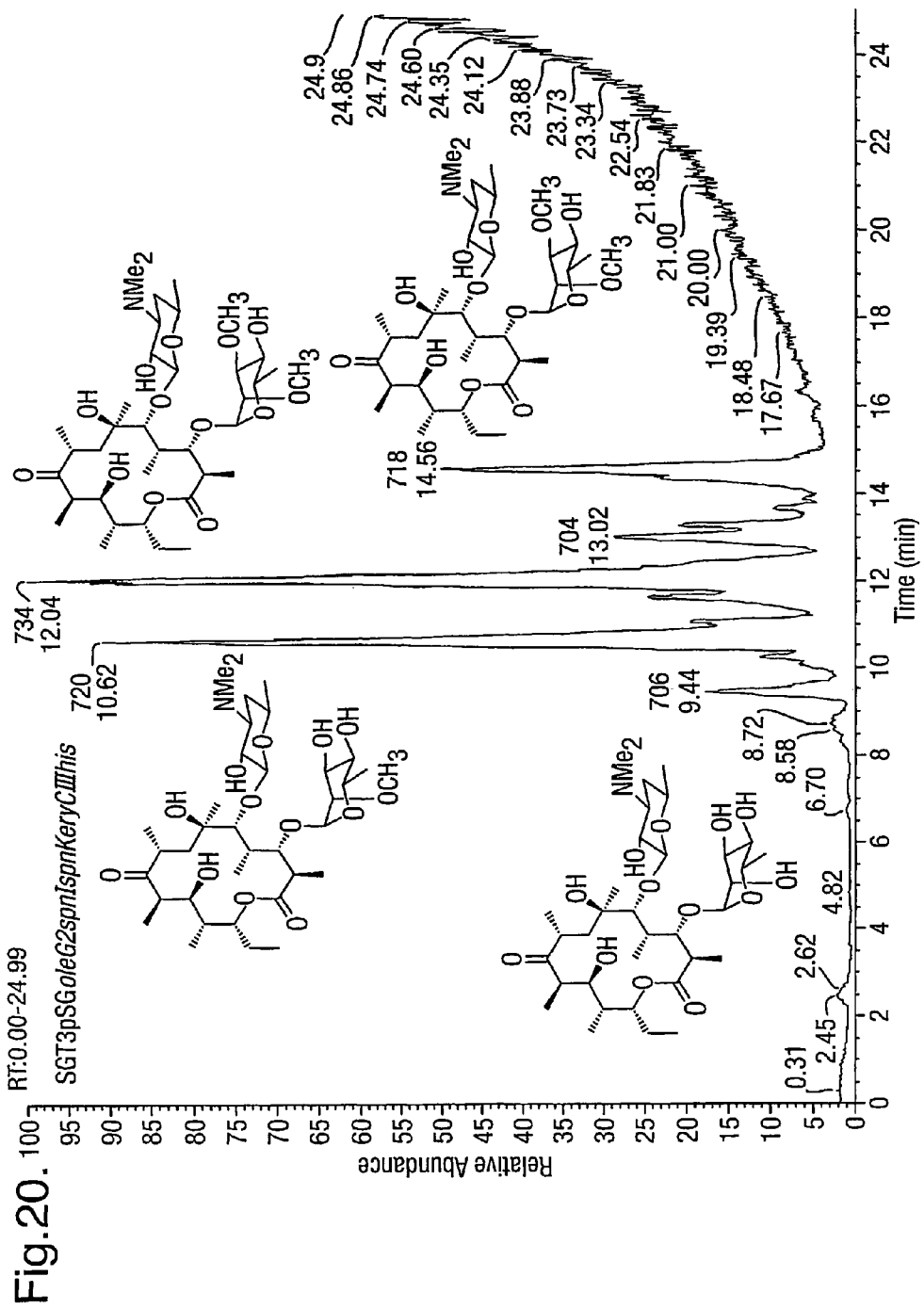
FIG. 20: Results of the analysis of the culture supernatant of SGT3pSGcasoleG2spnIspnKeryCIII.

The PCR product using the primer combination of caseryCIII2 and SG14 was isolated using the methods described for the construction of expression plasmid for eryCIII. The gene cassette pSGcasoleG2spnIspnKeryCIIIhis was created using the approach described above. Strain SGT3pSGcasoleG2spnIspnKeryCIIIhis was isolated and cells were grown as described in Materials and Methods. The culture supernatant of the clone was assessed using techniques described in Materials and Methods. Compounds 3-O-mannosyl erythromycin D, 3-O-(2'-O-methyl rhamnosyl erythromycin D, 3-O-(2',3'-bis-O-methyl rhamnosyl erythromycin D), 3-O-(2'-O-methyl rhamnosyl)-6-deoxyerythromycin D and 3-O-(2',3'-bis-O-methyl rhamnosyl)-6-deoxy erythromycin D were detected (FIG. 20). The introduction of the his$_6$-tag at the C-terminus of EryCIII therefore seems to improve glycosyl transfer of the desosamine sugar residue to its substrates. This result indicates that the expression of the last gene of the gene cassette can be improved by introducing the his$_6$-tag fusion at the C-terminal end of the protein.

OleP Cassette

Figure 23:
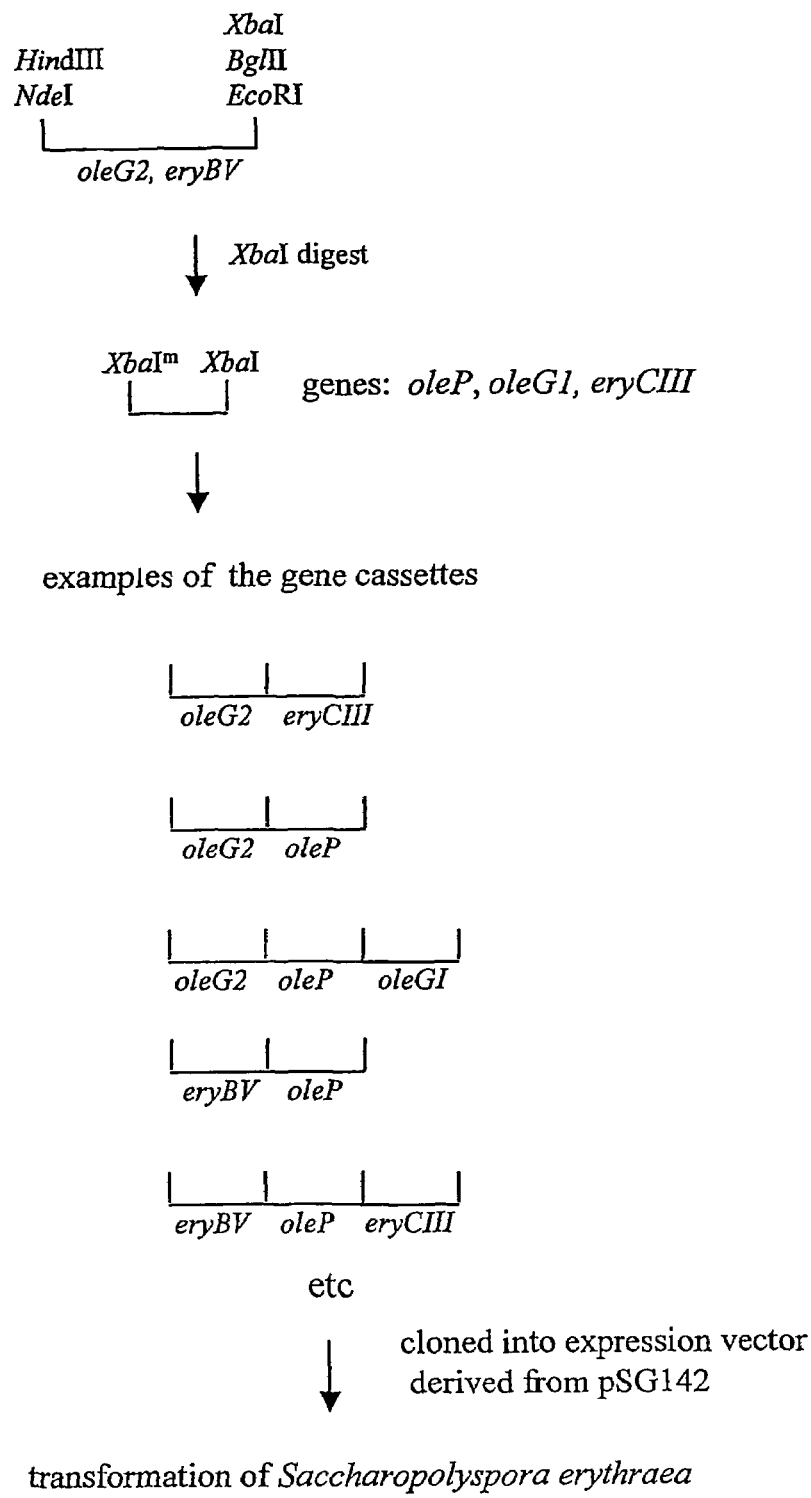
FIG. 23: Scheme for the construction of gene cassettes and transformation into S. erythraea.

To include oleP into the arrangements of gene cassettes, primers OlePcass1 5'-GGGTCTAGATCCGGACGAACG-CATCGATTAATTAAGGAGGACAGATATGA CCGATACGCACACCGGACCGACACC-3' (SEQ ID NO: 49) and OlePCass2 5'-GGGGTCTAGAGGTCACCAG-GAGACGATCTGGCGTTCCAGTCCGCGGATCA -3' (SEQ ID NO: 50) were used. The PCR fragment—using plasmid pSGOleP as template—was isolated, treated with T4 polynucleotide kinase and cloned into SmaI cut pUC18. After transformation into E. coli DH10B the construct was isolated and verified. Plasmid pSGOlePcass was used to transform the dam$^-$ Escherichia coli strain ET12567. The plasmid DNA was isolated and after digestion with XbaI, a 1.3 kb fragment was isolated, ligated with the vector fragment of XbaI digested constructs and used to transform E. coli DH10B. An overview over these constructs is given in FIG. 23.

Preparation of 3-O-rhamnosyl-8,8a-dehydro-6-deoxyerythronolide B

S. erythraea strain SGT1pSGcasoleG2leP was isolated using the methods described above and 4 l of cells were grown as described in Material and Methods. The culture supernatant were isolated and analysed as described for the preparation of 3-O-(2'-O-methylrhamnosyl)erythronolide B. Two novel compounds, 3-O-rhamnosyl-8,8a-dehydro-6-deoxyerythronolide B and 3-O-rhamnosyl-8,8a-dihydroxy-6-deoxyerythronolide B were detected (FIG. 24). The structure of 3-O-rhamnosyl-8,8a-dehydro-6-deoxyerythronolide B was confirmed by NMR analysis.

TABLE 17

$^1$H NMR Data for 3-O-rhamnosyl-8,8a-dehydro-6-deoxyerythronolide B

| Proton | δ$_H$ | multiplicity | coupling (Hz) |
|---|---|---|---|
| 2-H | 2.80 | dq | 7.3, 7.3 |
| 3-H | 3.76 | dd | 7.5, 2.6 |
| 4-H | 1.66 | m | |
| 5-H | 3.48 | dd | 7.9, 2.6 |
| 6-H | 2.00 | m | |
| 7-H$_a$ | 2.18 | m | |
| 7-H$_b$ | 2.39 | d | 16.4 |
| 8a-H$_a$ | 5.42 | s | |
| 8a-H$_b$ | 5.68 | s | |
| 10-H | 3.21 | m | |
| 11-H | 3.68 | m | |
| 12-H | 1.72 | m | |
| 13-H | 5.18 | ddd | 9.2, 4.9, 1.3 |
| 14-H$_a$ | 1.53 | m | |
| 14-H$_b$ | 1.77 | m | |
| 15-H$_3$ | 0.90 | dd | 7.3, 7.3 |
| 16-H$_3$ | 1.20 | d | 7.3 |
| 17-H$_3$ | 1.06 | d | 6.8 |
| 18-H$_3$ | 1.12 | d | 6.8 |
| 19-H$_3$ | 0.98 | d | 6.8 |

TABLE 17-continued

¹H NMR Data for 3-O-rhamnosyl-8,8a-dehydro-6-deoxyerythronolide B

| Proton | $\delta_H$ | multiplicity | coupling (Hz) |
|---|---|---|---|
| 20-H$_3$ | 0.96 | d | 7.3 |
| 1'-H | 4.83 | obscured | |
| 2'-H | 3.96 | dd | 3.2, 1.7 |
| 3'-H | 3.62 | dd | 9.6, 3.2 |
| 4'-H | 3.42 | dd | 9.6, 9.6 |
| 5'-H | 3.69 | m | |
| 6'-H$_3$ | 1.28 | d | 6.2 |

TABLE 18

¹³C NMR Data for 3-O-rhamnosyl-8,8a-dehydro-6-deoxyerythronolide B

| Carbon | $\delta C$ |
|---|---|
| 1 | 177.3 |
| 2 | 45.0 |
| 3 | 81.1 |
| 4 | 42.0 |
| 5 | 75.5 |
| 6 | 33.3 |
| 7 | 31.2 |
| 8 | 148.4 |
| 8a | 119.3 |
| 9 | 210.2 |
| 10 | 43.8 |
| 11 | 71.1 |
| 12 | 40.5 |
| 13 | 76.0 |
| 14 | 25.1 |
| 15 | 9.3 |
| 16 | 13.7 |
| 17 | 8.6 |
| 18 | 18.3 |
| 19 | 8.8 |
| 20 | 8.8 |
| 1' | 102.4 |
| 2' | 70.5 |
| 3' | 70.9 |
| 4' | 72.2 |
| 5' | 69.3 |
| 6' | 16.6 |

Construction of Expression Plasmid for oleG1

Figure 26:
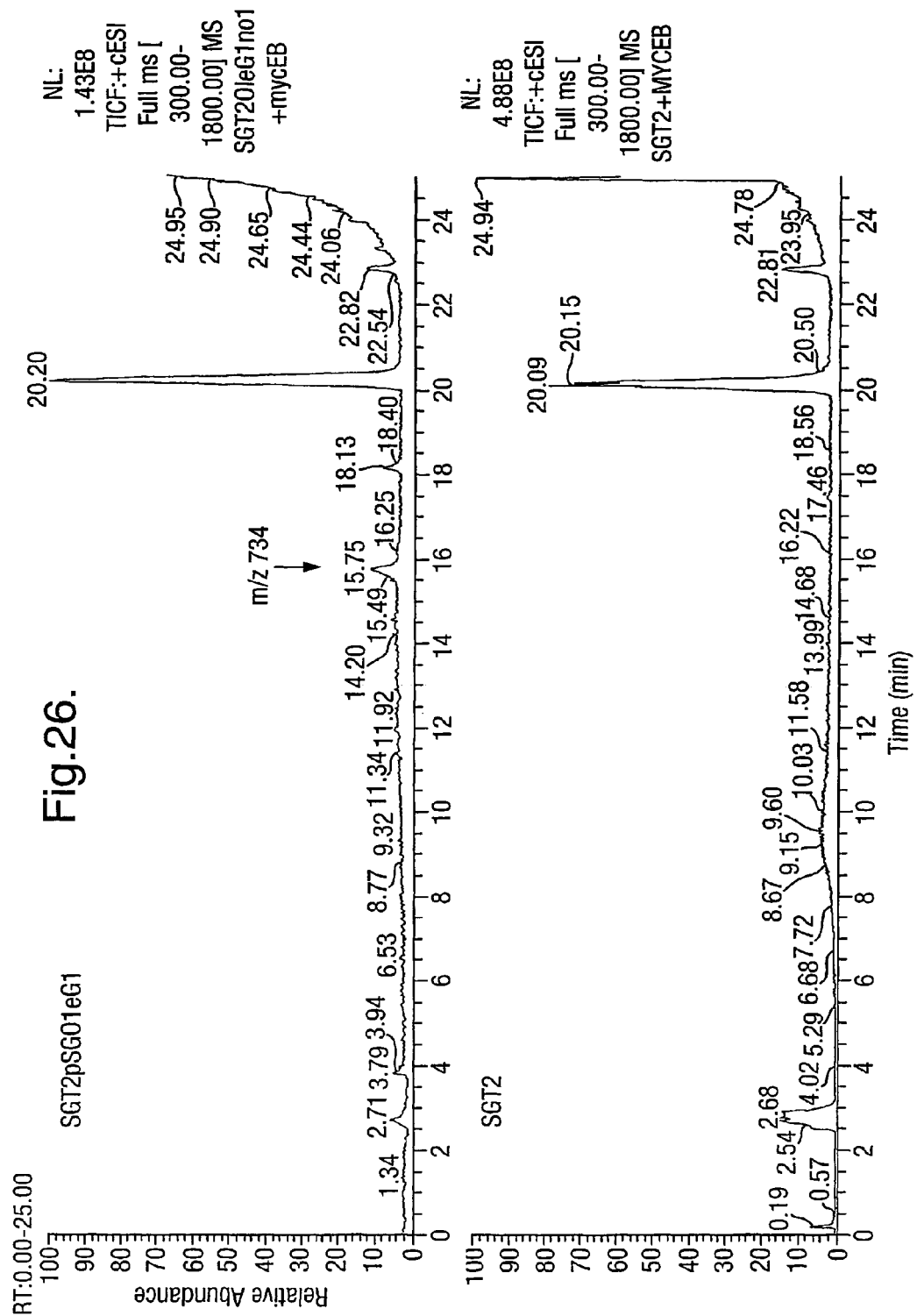
FIG. 26: Results of the complementation of the eryCIII mutation in S. erythraea SGT2 and SGT2pSGOleG1. 3-O-mycarosyl erythronolide B was fed to the cultures as described previously (Gaisser et al., 2000). The presence of 3-O-mycarosyl erythronolide B is indicated by a peak of a retention time of 20 min. The peak of a retention time of 15.7 and 734 m/z indicates the presence of erythromycin A.

To establish which of the various possible start codons in the published sequence (accession number AJ002638) is used for the expression of oleG1 (FIG. 25), various constructs were tested by measuring the complementation of the eryCIII mutation in *S. erythraea* SGT2 after feeding with 3-O-mycarosyl erythronolide B using techniques described in Materials and Methods. Complementation indicated by the production of small amounts of erythromycin A was only observed when vector pSGOleG1 was used (FIG. 26). Plasmid pSGOleG1 was isolated using the primers 7390 5'-CCGCCATATGAGCATCGCGTCGAACG-GCGCGCGCTCGGC-3' (SEQ ID NO: 51) Ole2 5'-TCA-GATCTCCGCCTTCCCGCCATCGCGCCGGTGGCAT-3' (SEQ ID NO: 52) to amplify oleG1. The cloning procedure was as described for the construction of the expression plasmid for oleG2. Expression vectors using the published start codon or one of the following ATG codons indicated in FIG. 25 did not complement the eryCIII mutation of SGT2 after feeding with 3-O-mycarosyl erythronolide B. This result indicates that the correct start codon which is required for the expression of oleG1 is the ATG overlapping with the oleP1 stop codon (FIG. 25).

6-deoxyerythronolide B as a Substrate for oleG2, but not oleG1

Figure 27:
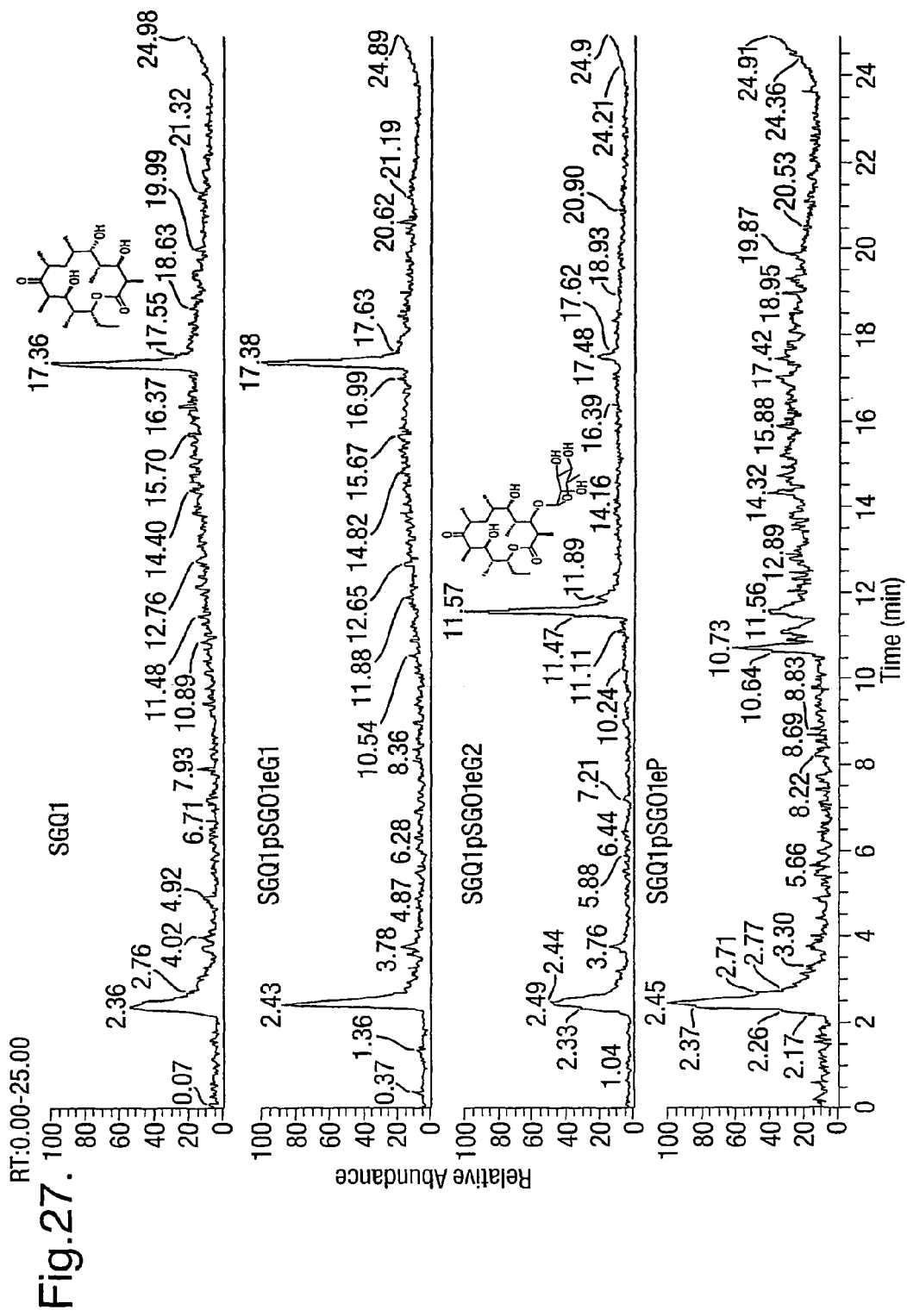
FIG. 27: Results of the feeding of 6-deoxyerythronolide B to SGQ1, SGQ1pSGOleG1, SGQ1pSGOleG2 and SGQ1pSGOeP. Structures of the major compounds are indicated.

The *S. erythraea* mutant SGQ1 (SGT2DeryF) was created starting with SGT2 by introducing a deletion in the eryF gene as described above using standard microbiological techniques. SGQ1 was transformed with the plasmid constructs pSGOleG2, pSGOleP and pSGOleG1 and feeding experiments using the sterile filtered culture supernatants of SGT1 containing 6-deoxyerythronolide B were carried out as described in Materials and Methods. The results indicate, that both, OleG2 and to a smaller extent OleP, accept 6-deoxyerythronolide B as a substrate (FIG. 27). 6-deoxyerythronolide B is not a substrate for OleG1.

3-O-rhamnosyl-6-deoxyerythronolide B as a Substrate for oleP

Figure 28:
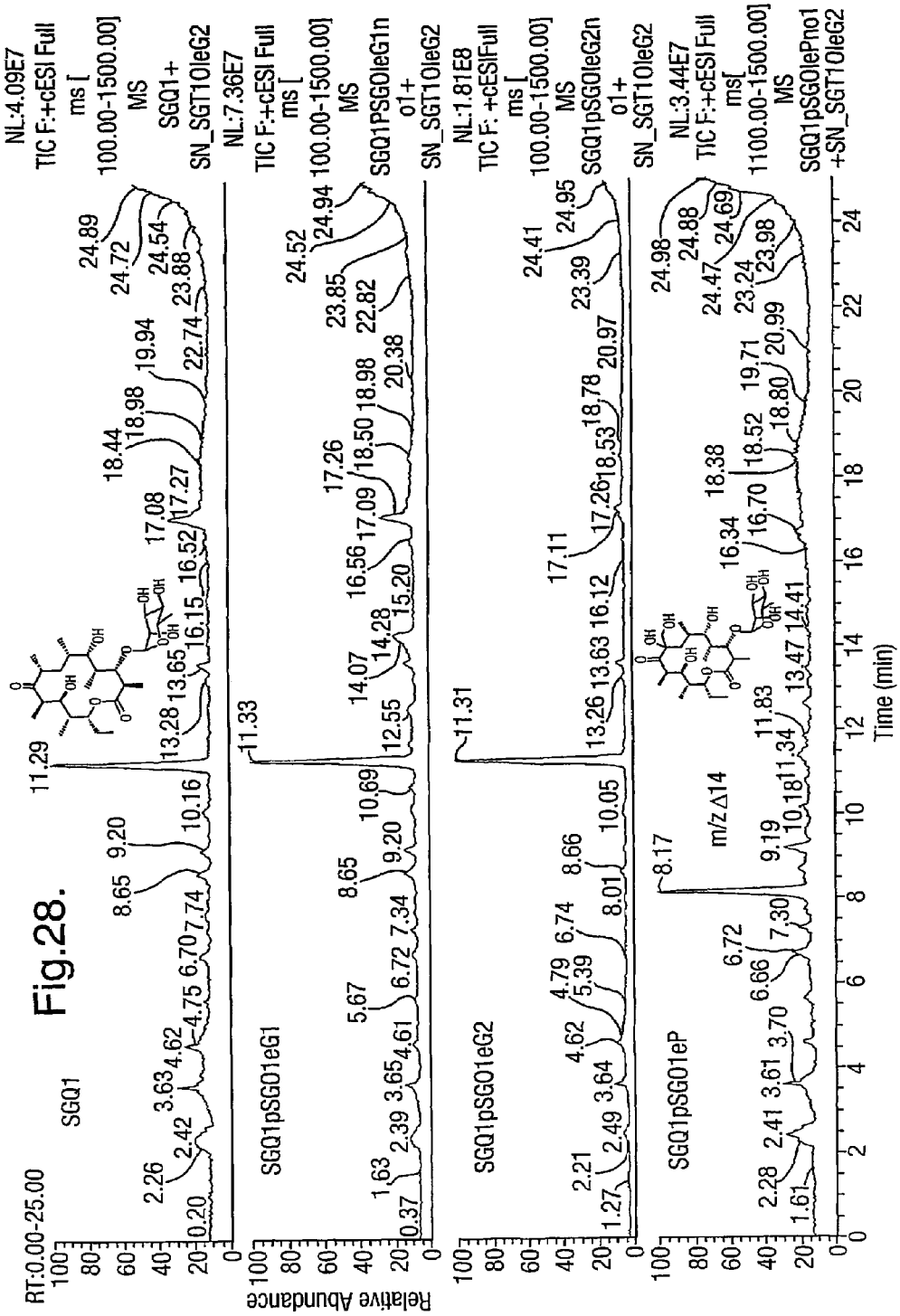
FIG. 28: Results of the feeding of 3-O-rhamnosyl-6-deoxyerythronoli-de B to SGQ 1, SGQ1SGOleG1, SGQ1pSGOleG2 and SGQ1pSGOleP. Structures of the major compounds are indicated.
Figure 29:
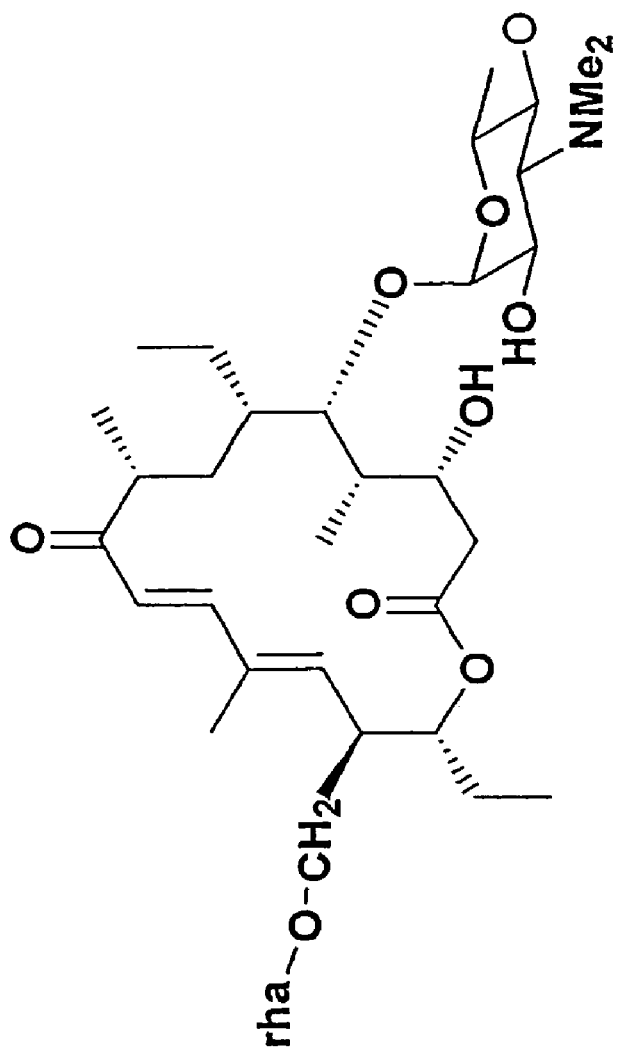
FIG. 29: Structure of 23-O-rhamnosyl-5-O-mycaminosyl-tylactone.
Figure 30:
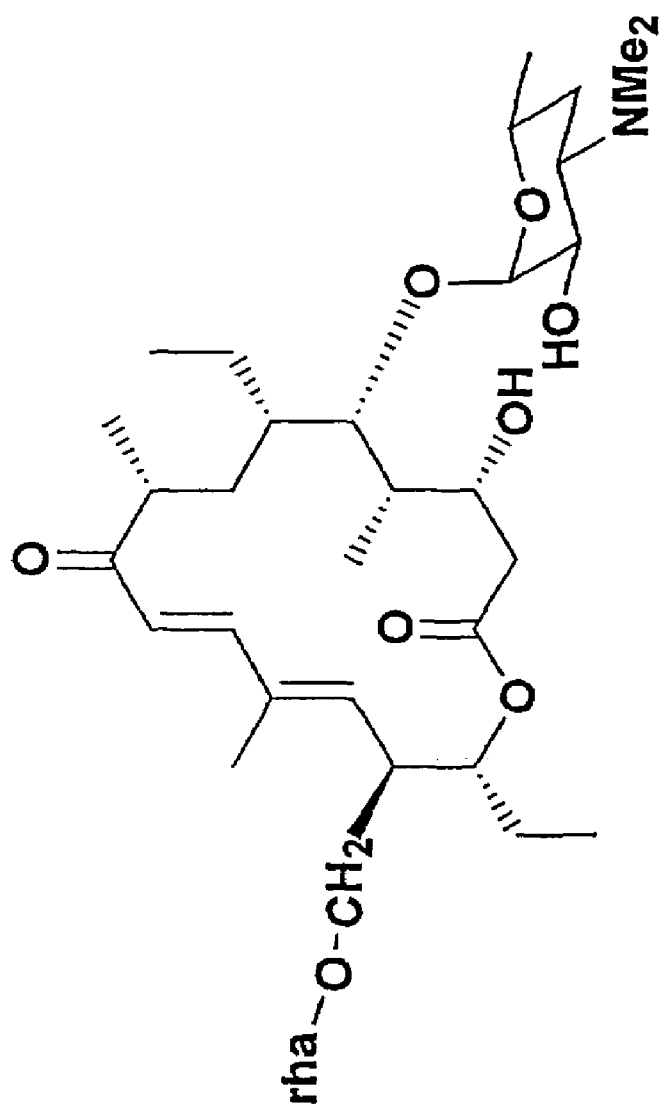
FIG. 30: Structure of 23-O-rhamnosyl-5-O-desosaminyl-tylactone.
Figure 31:
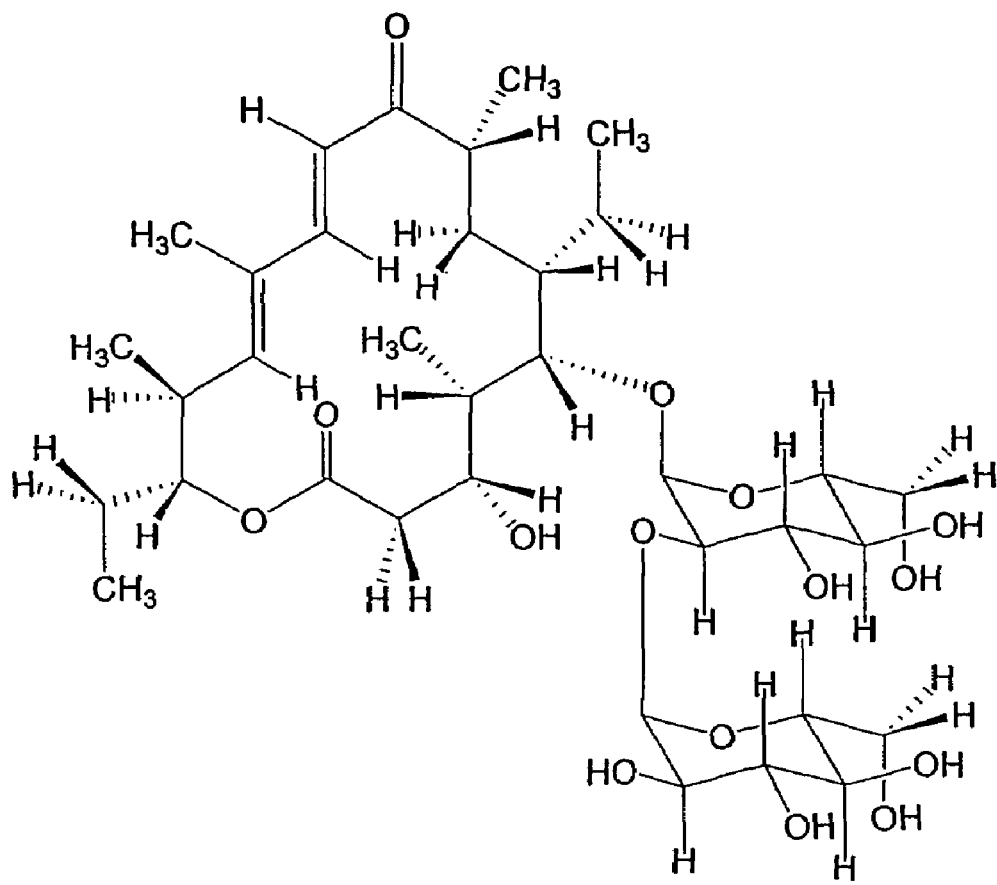
FIG. 31: Structure of 5-O-(2'-O-)bis-glucosyl-tylactone.

Culture supernatants of SGT1pSGOleG2 containing 3-O-rhamnosyl-6-deoxyerythronolide B was sterile filtered and were added to cultures of SGQ1, SGQ1pSGOleG2, SGQ1pSGOleP and SGQ1pSGOleG1 using standard microbiological techniques. The analysis of these culture supernatants indicates that 3-O-rhamnosyl-6-deoxyerythronolide B is a substrate for OleP but not for OleG1 (FIG. 28).

Feeding of 8,8a-epoxy-3-O-mycarosyl Erythronolide B

Cell cultures of SGT1pSGOleG1 were grown as described in Material and Methods and fed with 8,8a-epoxy-3-O-mycarosyl erythronolide B as described earlier (Gaisser et al., 2000). The culture supernatant was analysed using techniques described above and the results indicate that 8,8a-epoxy-3-O-mycarosyl erythronolide B is a substrate for OleG1.

Expression of pSGcassOleG2EryCIII in SGT3

The gene oleG2 was amplified using the primers casoleG21 and casoleG22 (see above) and the DNA of plasmid pSGOleG2 as a template (Gaisser et al., 2000). The PCR product was ligated into SamI cut pUC18 and transformed into the *Escherichia coli* strain DH10B. The sequence of the PCR product was verified. The resulting plasmid was digested using the restriction enzymes EcoRI and HindIII followed by a ligation into EcoRIHindIII digested pUC19 and transformation of *E. coli* DH10B. The resulting plasmid was named pSGcassOleG2.

The gene eryCIII was amplified using the primers caseryCIII and caseryCIII2 (see above) and the DNA of plasmid pSGEryCIII as a template. The PCR product was ligated into SamI cut pUC18 and transformed into the *Escherichia coli* strain DH10B. The sequence of the PCR produce was verified. The resulting plasmid was transformed into the dam *Escherichia coli* strain ER12567. The DNA of the transformant was isolated and digested using the restriction enzyme Xbai. The 1.3 kb DNA fragment was isolated and ligated into XbaI digested pSGcassOleG2 and transformed into *E. coli* DH10B. The correct orientation of eryCIII was assessed using restriction digests and plasmid pOleG2EryCIII was isolated. A DNA band of about 2.8 kb was isolated after a restriction digest using NdeI, BglII and DraI followed by a ligation into the NdeI/BglII digested expression vector pSG142 and transformation of *E. coli* DH10B. Plasmid pSGcassOleG2EryCIII was isolated and used to transform the *S. erythraea* mutant SGT3. Thiostrepton resistant colonies were selected. Culture supernatants of these strains were isolated as described (Gaisser et al., 1997) and analysed using electrospray mass spectrometry. A peak with the retention time of 9.2 and the m/z of 706 was detected which indicates the presence of rhamnosyl-erythromycin D in the supernatant. Another peak with m/z 690 was also found which indicates the presence of rhamnosyl-6-deoxyerythromycin D in the supernatant (see FIG. 16).

Anti-microbial activity of the resulting erythromycin analogues was demonstrated through development of zones of inhibition in a lawn of erythromycin-sensitive *Bacillus subtilis* around plugs of the transformed cells in a standard bioassay.

Isolation of 5-O-glucosyl- and 5-O-desosaminyl-tylactone

Figure 5A:
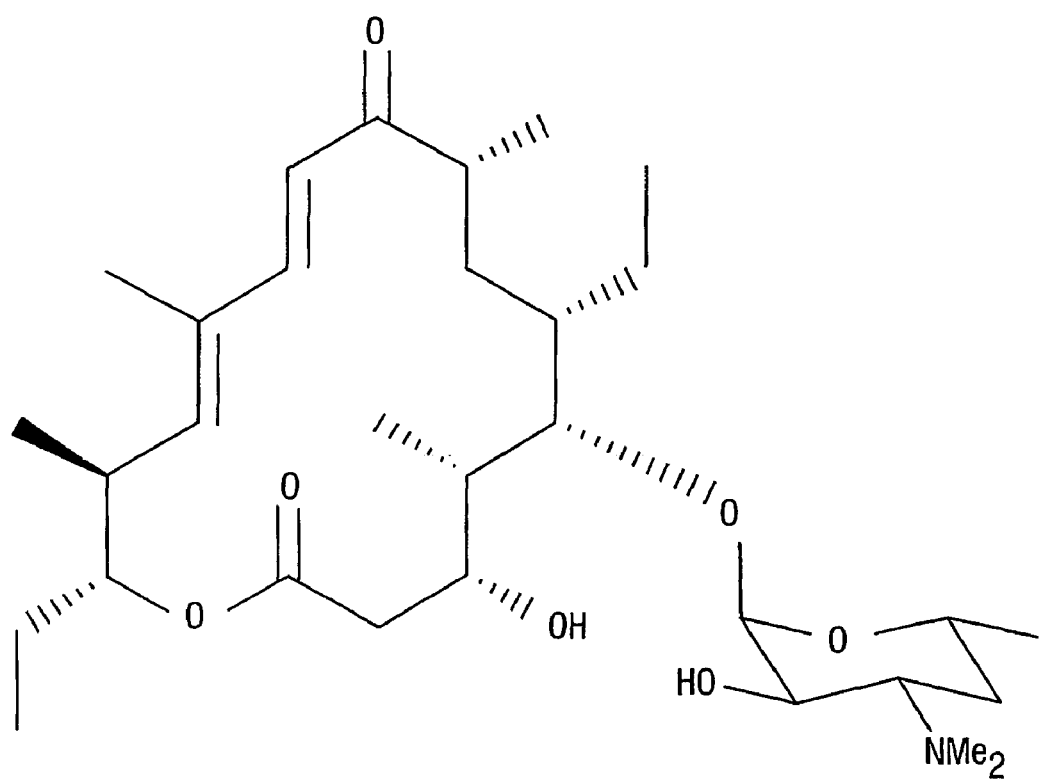
FIG. 5A: Structure of 5-O-desosaminyltylactone.
Figure 5B:
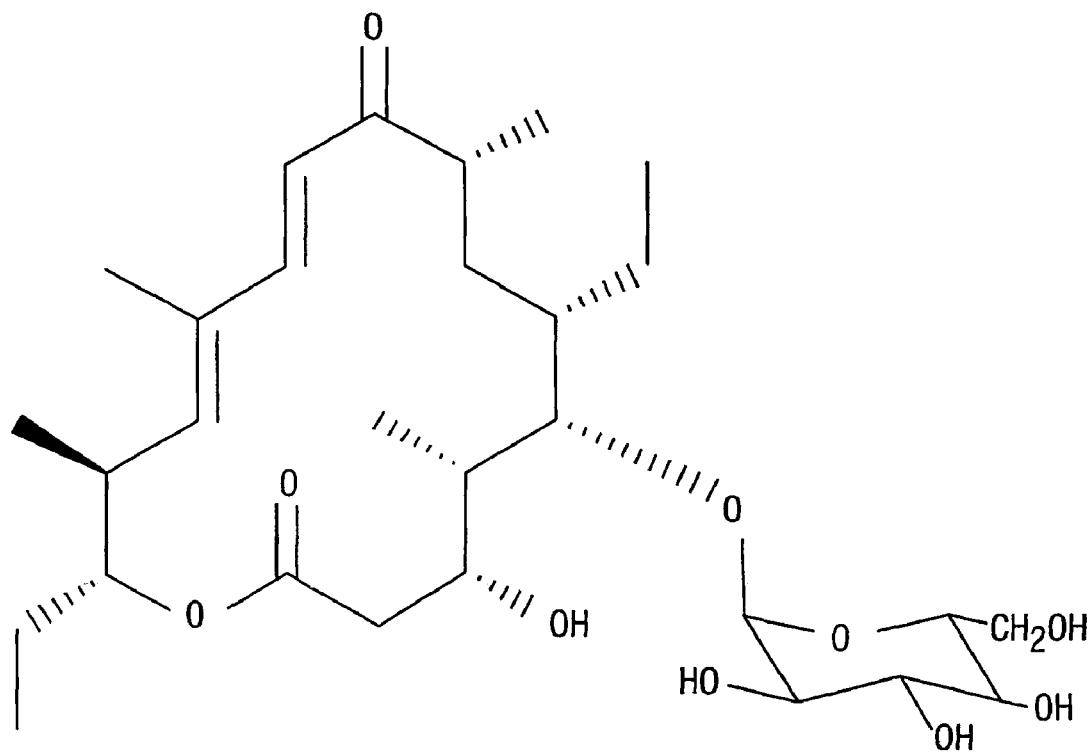
FIG. 5B: Structure of 5-O-glucosyltylactone.

Analysis of the tylactone standard using electrospray mass spectrometry showed a major peak at m/z 377 and minor peaks at m/z 359 and m/z 417. When tylactone was supplied to strain SGT2, in which both eryBV and eryCIII are deleted, peaks at m/z 557 and 579 were detected in the culture supernatants which would correspond to glucosylated derivatives of tylactone. This confirmed the presence of another glycosyltransferase in *S. erythraea* which accepts tylactone as a substrate. However, the analysis of the culture supernatant of *S. erythraea* SGT2(pSGTYLM2) fed with tylactone revealed a major peak at m/z 552, which fragmented into peaks at m/z 158 and m/z 359 in MS/MS experiments, indicating the presence of 5-O-desosaminyl-tylactone in the expression medium of *S. erythraea* SGT2(pSGTYLM2). The putative glucosyl- and desosaminyl-tylactones (2.2 mg and 2.0 mg respectively from 1.5 l of culture broth) were analysed and the structures were fully confirmed as 5-O-glucosyl- and 5-O-desosaminyl-tylactone by using $^1$H and $^{13}$C NMR (see FIGS. 5A and 5B respectively).

TABLE 19

$^1$H NMR Data for 5-desosaminyl-tylactone

| Proton | $\delta_H$ | Multiplicity | Coupling |
|---|---|---|---|
| 2-H$_a$ | 2.49 | dd | 17.4, 9.6 |
| 2-H$_b$ | 2.04 | d | 17.4 |
| 3-H | 3.72 | d | 9.6 |
| 4-H | 1.70 | m | |
| 5-H | 3.77 | d | 9.6 |
| 6-H | 1.11 | m | |
| 7-H$_a$ | 1.72 | m | |
| 7-H$_b$ | 1.45 | m | |
| 8-H | 2.64 | m | |
| 10-H | 6.47 | m | 15.4 |
| 11-H | 7.27 | d | 15.4 |
| 13-H | 5.70 | d | 10.4 |
| 14-H | 2.81 | ddq | 10.2, 10.2, 6.5 |
| 15-H | 4.72 | ddd | 9.7, 9.7, 2.5 |
| 16-H$_a$ | 1.90 | m | |
| 16-H$_b$ | 1.60 | m | |
| 17-H$_3$ | 0.96 | dd | 7.4, 7.4 |
| 18-H$_3$ | 1.04 | D | 6.8 |
| 19-H$_a$ | 1.60 | m | |
| 19-H$_b$ | 1.42 | m | |
| 20-H$_3$ | 0.85 | dd | 7.2, 7.2 |
| 21-H$_3$ | 1.19 | d | 6.9 |
| 22-H$_3$ | 1.84 | br·s | |
| 23-H$_3$ | 1.08 | d | 6.5 |
| 1'-H | 4.28 | d | 7.3 |
| 2'-H | 3.37 | dd | 10.5, 7.3 |
| 3'-H | 3.20 | ddd | 11.4, 11.4, 4.0 |
| 4'-H$_a$ | 1.93 | m | |
| 4'-H$_b$ | 1.44 | m | |
| 5'-H | 3.61 | dq | 10.2, 6.1 |
| 6'-H$_3$ | 1.26 | d | 6.1 |
| 7'(CH$_3$)$_2$ | 2.70 | s | |

TABLE 20

$^{13}$C NMR Data for 5-desosaminyl-tylactone

| Carbon | $\delta_c$ |
|---|---|
| C1 | 173.6 |
| C2 | 39.7 |
| C3 | 67.0 |
| C4 | 40.9 |
| C5 | 78.6 |
| C6 | 39.4 |
| C7 | 33.3 |
| C8 | 44.7 |
| C9 | 205.5 |
| C10 | 118.2 |
| C11 | 148.1 |
| C12 | 133.3 |
| C13 | 146.0 |
| C14 | 38.3 |
| C15 | 78.4 |
| C16 | 23.9 |
| C17 | 8.4 |
| C18 | 8.3 |
| C19 | 20.5 |
| C20 | 10.8 |
| C21 | 16.3 |
| C22 | 11.4 |
| C23 | 14.3 |
| C' | 103.3 |
| C2' | 69.3 |
| C3' | 65.0 |
| C4' | 29.7 |
| C5' | 67.8 |
| C6' | 19.5 |
| N7'-(CH$_3$)$_2$ | 38.5 |

TABLE 21

$^1$H NMR Data for 5-glucosyl-tylactone

| Proton | $\delta_H$ | Multiplicity | Coupling |
|---|---|---|---|
| 2-H$_a$ | 2.49 | dd | 17.4, 9.6 |
| 2-H$_b$ | 2.05 | d | 17.4 |
| 3-H | 3.74 | br·d | 9.9 |
| 4-H | 1.68 | m | |
| 5-H | 3.77 | br·d | 9.4 |
| 6-H | 1.11 | m | |
| 7-H$_a$ | 1.72 | m | |
| 7-H$_b$ | 1.48 | m | |
| 8-H | 2.66 | dqd | 11.8, 6.9, 3.6 |
| 10-H | 6.44 | d | 15.5 |
| 11-H | 7.23 | d | 14.9 |
| 13-H | 5.67 | d | 10 |
| 14-H | 2.78 | ddq | 10.3, 10.3, 6.6 |
| 15-H | 4.68 | ddd | 9.1, 9.1, 2.7 |
| 16-H$_a$ | 1.86 | m | |
| 16-H$_b$ | 1.58 | m | |
| 17-H$_3$ | 0.94 | dd | 7.3, 7.3 |
| 18-H$_3$ | 1.04 | d | 6.9 |
| 19-H$_a$ | 1.43 | m | |
| 19-H$_b$ | 1.64 | m | |
| 20-H$_3$ | 0.87 | t | 7.3 |
| 21-H$_3$ | 1.19 | d | 6.9 |
| 22-H$_3$ | 1.85 | br·s | |
| 23-H$_3$ | 1.07 | d | 6.6 |
| 1'-H | 4.28 | d | 7.8 |
| 2'-H | 3.17 | dd | 9.2, 7.8 |
| 3'-H | 3.33 | m | |
| 4'-H | 3.34 | m | |
| 5'-H | 3.19 | m | |
| 6'-H$_a$ | 3.82 | dd | 11.6, 2.6 |
| 6'-H$_b$ | 3.72 | dd | 11.6, 4.8 |

TABLE 22

$^{13}$C NMR Data for 5-glucosyl-tylactone

| Carbon | $\delta_c$ |
|---|---|
| C1 | 173.6 |
| C2 | 39.8 |
| C3 | 66.9 |
| C4 | 41.1 |
| C5 | 79.1 |
| C6 | 39.6 |
| C7 | 33.4 |
| C8 | 45.1 |
| C9 | 205.7 |
| C10 | 118.6 |
| C11 | 148.2 |
| C12 | 133.9 |
| C13 | 146.3 |
| C14 | 38.4 |
| C15 | 78.6 |
| C16 | 24.3 |
| C17 | 8.6 |
| C18 | 8.2 |
| C19 | 21.3 |
| C20 | 10.9 |
| C21 | 16.5 |
| C22 | 11.1 |
| C23 | 14.9 |
| C' | 103.1 |
| C2' | 74.3 |
| C3' | 76.7 |
| C4' | 70.2 |
| C5' | 75.9 |
| C6' | 61.2 |

Production of 23-hydroxy 5-O-mycaminosyl tylactone

The *S. erythraea* strain SGT2pSGTylM2 was grown as described previously (Gaisser et al., 1997). Tylactone was fed to these cultures after 48 h (compared to 24 h in previous feedings). Analysis of the supernatants using electrospray mass spectroscopy revealed the presence of a new peak at m/z 552 which was identified as 5-O-desosaminyl-tylacton-e. A second peak with m/z 568 was also detected in this supernatant and MS/MS analysis of this compound confirmed the presence of 5-O-mycaminosyl-tylactone in the expression medium of *S. erythaea* strain SGT2pSGTylM2. An aliquot of this supernatant was used to feed cultures of SGT2pSGTYLH. Analysis of the supernatants revealed a shift of the 5-O-mycaminosyl-tylactone peak of m/z 568 to 584 m/z. This result indicates that 5-O-mycaminosyl-tylactone was further processed by the expression of the TylH locus (Fouces et al., 1999). The TylH locus consists of two genes, tylH1 (3Fe4S-type ferrodoxin) and tylH2 (P450 type cytochrome), postulated to form the oxidoreduction system involved in C23 oxidation) to produce 23-hydroxy 5-O-mycaminosyl tylactone in the culture supernatant.

Production of 23-O-rhamnosyl 5-O-mycaminosyl tylactone

An aliquot of the supernatant containing 5-O-mycaminosyl-tylactone was used to feed cultures of *S. erythraea* SGT2pSGTYLHN. Analysis of the supernatants using electrospray mass spectrosopy revealed the presence of a new peak at m/z 730. The shift by m/z 146 indicated the presence of 23-rhamnosyl 5-O-mycaminosyl tylactone in the culture supernatant.

Isolation of 5-O-(2'-O)-bis-glucosyl-tylactone

Cultures of SGT2pSGOLED are fed with tylactone. The supernatants of these cultures contain a new product with m/z consistent with the structure of diglucosyl-tylactone. The compound was purified as described above and the structure fully confirmed by $^1$H and $^{13}$C NMR

TABLE 23

$^1$H NMR Data for 5-O(2'-O)-bis-glucosyl-tylactone

| Proton | $\delta_H$ | multiplicity | coupling |
|---|---|---|---|
| 2-$H_a$ | 2.05 | d | 17.5 |
| 2-$H_b$ | 2.48 | dd | 17.5, 9.6 |
| 3-H | 3.73 | br·d | 9.8 |
| 4-H | 1.74 | m | |
| 5-H | 3.78 | d | 9.4 |
| 6-H | 1.11 | m | |
| 7-$H_a$ | 1.45 | m | |
| 7-$H_b$ | 1.75 | m | |
| 8-H | 2.65 | m | |
| 10-H | 6.46 | d | 15.3 |
| 11-H | 7.23 | d | 15.3 |
| 13-H | 5.66 | d | 10.2 |
| 14-H | 2.78 | ddq | 10.2, 10.2, 6.4 |
| 15-H | 4.68 | ddd | 10.2, 9.4, 2.6 |
| 16-$H_a$ | 1.58 | m | |
| 16-$H_b$ | 1.86 | m | |
| 17-$H_3$ | 0.94 | dd | 7.3, 7.3 |
| 18-$H_3$ | 1.07 | d | 6.8 |
| 19-$H_a$ | 1.43 | m | |
| 19-$H_b$ | 1.63 | m | |
| 20-$H_3$ | 0.88 | dd | 7.3, 7.3 |
| 21-$H_3$ | 1.21 | d | 6.8 |
| 22-$H_3$ | 1.85 | s | |
| 23-$H_3$ | 1.07 | d | 6.6 |
| 1'-H | 4.42 | d | 7.7 |
| 2'-H | 3.43 | m | |
| 3'-H | 3.52 | dd | 9.0, 9.0 |
| 4'-H | 3.37 | m | |
| 5'-H | 3.21 | m | |
| 6'-$H_a$ | 3.70 | m | |
| 6''-$H_b$ | 3.82 | dd | 11.5, 2.6 |
| 1''-H | 4.56 | d | 7.7 |
| 2''-H | 3.27 | m | |
| 3''-H | 3.37 | m | |
| 4''-H | 3.28 | m | |
| 5''-H | 3.29 | m | |
| 6''-$H_a$ | 3.71 | m | |
| 6''-$H_b$ | 3.89 | br·d | 11.9 |

TABLE 24

$^{13}$C NMR Data for 5-O(2'-O)-bis-glucosyl-tylactone

| Carbon | $\delta_c$ |
|---|---|
| C1 | 173.4 |
| C2 | 40.0 |
| C3 | 66.9 |
| C4 | 40.9 |
| C5 | 78.7 |
| C6 | 39.6 |
| C7 | 33.5 |
| C8 | 45.2 |
| C9 | 205.7 |
| C10 | 118.8 |
| C11 | 148.5 |
| C12 | 133.9 |
| C13 | 146.4 |
| C14 | 38.5 |
| C15 | 78.5 |
| C16 | 24.4 |
| C17 | 8.6 |
| C18 | 8.3 |
| C19 | 21.1 |
| C20 | 11.1 |
| C21 | 16.6 |
| C22 | 11.8 |
| C23 | 15.0 |
| C1' | 101.0 |
| C2' | 81.7 |
| C3' | 76.2 |
| C4' | 70.1 |

TABLE 24-continued

<sup>13</sup>C NMR Data for 5-O(2'-O)-bis-glucosyl-tylactone

| Carbon | δ$_c$ |
|---|---|
| C5' | 75.8 |
| C6' | 61.2 |
| C1" | 104.3 |
| C2" | 74.2 |
| C3" | 76.6 |
| C4" | 70.0 |
| C5" | 77.1 |
| C6" | 61.6 |

Using the approach described for the creation of gene cassettes a strategy was developed to isolate 5-O-mycaminosyl-erythromycin A and 5-O-mycaminosyl-(4"-O-mycarosyl)-erythromycin A (FIG. 32).

Isolation of a Gene Cassette Encoding the Mycaminose Biosynthetic Pathway

A gene cassette was isolated encoding the genes responsible for the synthesis of TDP-D-mycaminose by amplifying tylMIII, tylB and tylMI from the tylosin biosynthetic gene cluster (accession numbers sf08223 and x81885) using chromosomal DNA of *Streptomyces fradiae* and the following primers:

```
TylM31 (SEQ ID NO: 53)
5' GGCGGGGAGAGAGGAGAGCATATGAACACGGCA GCGGGCCCGACC;

TylM32 (SEQ ID NO: 54)
5' CCCCCTCTAGAGGTCACTCGGGGACATACGGGGCGACGGGCAGCCG;

TylMI1 (SEQ ID NO: 55)
5' GGGGGTCTAGATCTTAATTAAGGAGGACAACCATGGCCCATTCATCCG
CCACGGCCGGACCGCAGGCCGA;

TylMI2 (SEQ ID NO: 56)
5' GGGGGTCTAGAGGCATATGTGTCGTCCITAATTAATCACCGGGTTTTC
TCCCTTCGCTCCGGGGAGCCCGGT;

TylB1 (SEQ ID NO: 57)
5' CCCCCTCTAGATCTTAKITAAGGAGGACACCCATGACAGGGCTGCCGC
GGCCCGCCGTCCGGGTG;
and TylB2 (SEQ ID NO: 58)
5' GGGGGTCTAGAGGTCACGGGCCTTCCTCCCAGGAGTCCAGCGCGGCGG
A.
```

The PCR fragments were cloned into SamI cut pUC18 using standard cloning techniques as described in Materials and Methods. The sequences of the cloned fragments were verified by DNA sequence analysis. No difference to the published sequence was detected for tylMI or tyIM3, but changes were detected in tylB which resulted in the change of 8 amino acid regions compared to the published sequence of TylB (FIG. 33).

Figure 34:
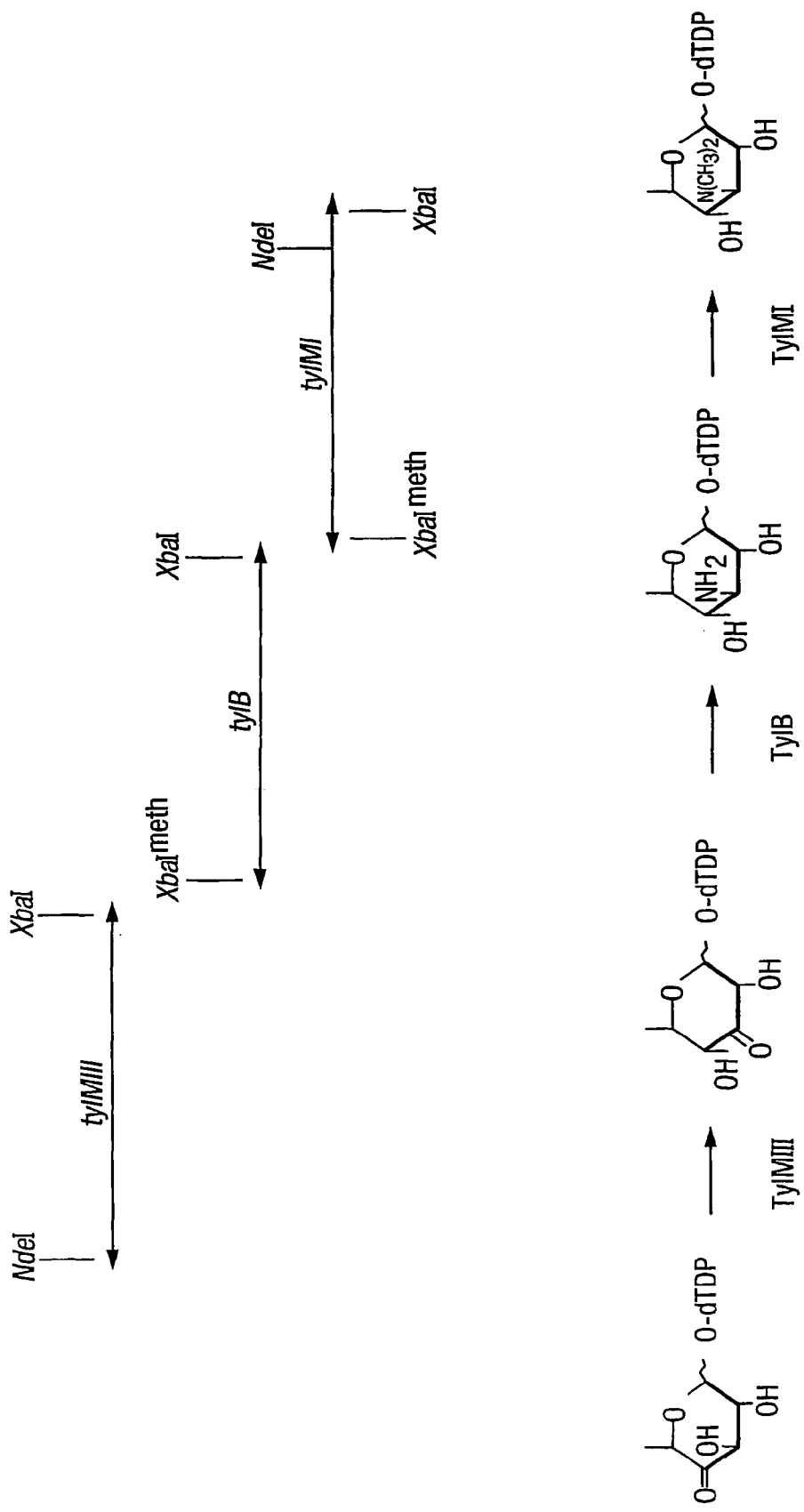
FIG. 34: Assembly of gene cassettes in pUC18 to produce constructs pUC18tylMII-tylB and pUC18tylMIII-tylB-tyMI.
Figure 35:
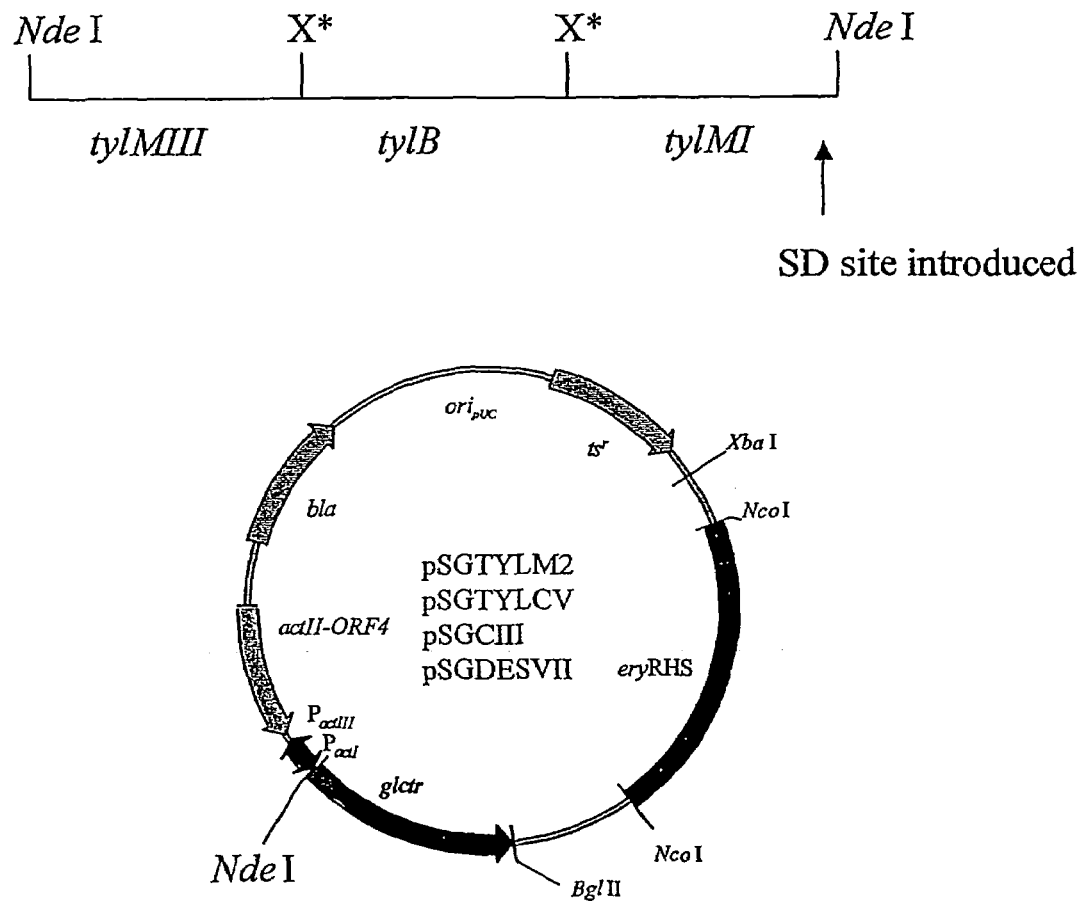
FIG. 35: Restriction maps for pSGCIII, pSGTYLM2, pSGDESVII and pSGTYLCV.

The gene cassettes were assembled in pUC18 using the approach described above (FIG. 34). The constructs pUC18tylMIII-tylB and pUC18tylMIII-tylB-tylMI were isolated and confirmed by restriction digests. Plasmid pUC18tylMIII-tylB-tylMI was digested with NdeI and the insert of about 3.5 kb was isolated and ligated into NdeI digested pSGCIII, pSGTYLM2, pSGDESVII and pSGTYLCV (FIG. 35). The correct orientation was confirmed using restriction digests.

Isolation of *S. erythraea* GG1

Plasmid pNCO62 (Gaisser et al., 1997) was isolated from a dam⁻ *Escherichia coli* host strain and digested with the restriction enzymes BalI/BclI. To introduce a 0.9 kb deletion into eryCIV as previously described (Salah-Bey et al., 1998) the ends of the DNA fragment were filled-in using standard microbiological techniques followed by a ligation step and electroporation of *E. coli* DH10B. Plasmid pGG17 was isolated and confirmed by sequence analysis and restriction digest. To introduce a selectable marker into this construct, a 1.1 kb fragment containing the thiostrepton resistance gene was isolated using plasmid pIB060 and ligated into pGG17 to generate pGG1 (FIG. 36). This plasmid was used to introduce the eryCIV deletion into the genome of *S. erythraea* wild type. To isolate the *S. erythraea* strain GG1 techniques described previously (Gaisser et al., 1998) were used.

Isolation of *S. erythraea* SGQ2

Figure 37:
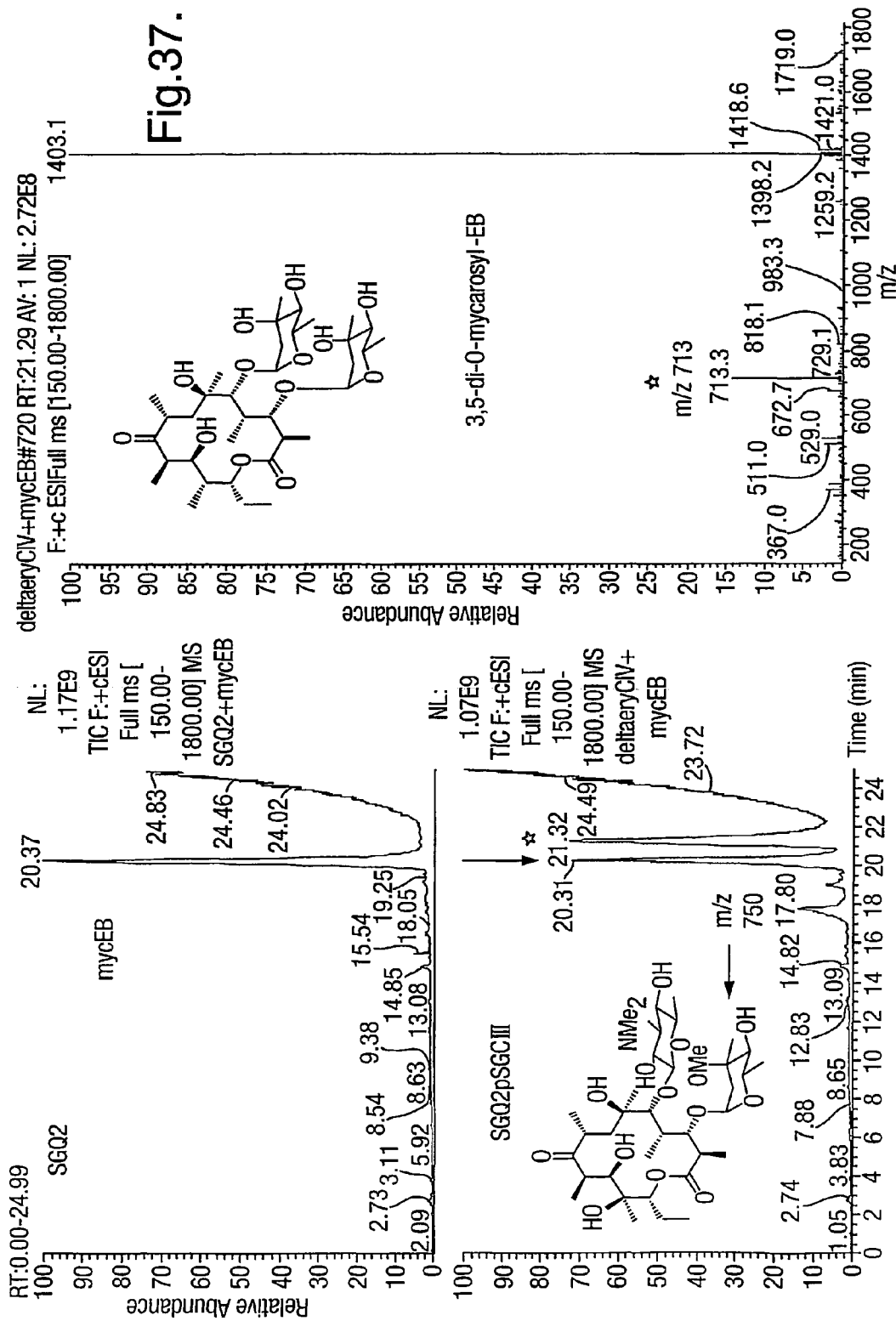
FIG. 37: Mass spectra of novel compounds 5-O-mycaminosyl-erythromycin A and 3,5-di-O-mycarosyl-erythronolide B.

Plasmid pGG1 was used to introduce a 0.9 kb deletion in eryCIV (Salah-Bey et al., 1998) into the *S. erythraea* mutant strain SGT2 to create the quadruple mutant SGQ2, using the microbiological techniques described previously (Gaisser et al., 1998). To verify the mutant, plasmid pSGCIII was used to transform SGQ2 and SGQ2pSGCIII was isolated. The cells were grown as described in Material and Methods and feeding with 3-O-mycarosyl erythronolide B was carried out as described (Gaisser et al., 2000). The supernatant of the cell culture was assessed using techniques described in Materials and Methods and two novel peaks with 750 m/z and 713 m/z were detected (FIG. 37). Using MS/MS techniques described in Materials and Methods these novel compounds were identified as 5-O-mycaminosyl-erythromycin A and 3,5-di-O-mycarosyl-erythronolide B.

Improved Production of 5-O-mycaminosyl-erythromycin A

The plasmid produced by the cloning of the mycaminose gene cassette tylMIII-tylB-tylM1 in correct orientation into the NdeI site of the plasmid pSGCIII was used to transform SGQ2 and strain SGQ2p(mycaminose)CIII was isolated. The cells were grown as described in Materials and Methods and feeding with mycarosyl-erythronolide B was carried out as described (Gaisser et al., 2000). The supernatant of the cell culture was analysed using HPLC-MS as desrided in Materials and Methods and peaks with 750 m/z and 713 m/z were detected, but the amount of the material with 750 m/z, corresponding to 5-O-mycaminosyl-erythromyc-in A, was significantly increased relative to the other peaks.

Construction of Expression Plasmid for tylCV

For expression of tylCV the primers TylCV1 5'-GCCT-GACGAAGGGTCCTGCCATATGGCTCATATTGCATT (SEQ ID NO: 59) and TylCV2 5'-GCGTGGGCCGGCCG-GAGATCTGGCCGCGGGGGACAGCA (SEQ ID NO: 60) were used to amplify tylCV using genomic DNA of *S. fradiae* as template. The PCR fragment was isolated and cloned as described for the construction of expression plasmid of eryCIII. After digestion with NdeI/BglII a 1.2 kb fragment was isolated, ligated into pSG142 digested with the same restriction enzymes and used transform *E. coli* DH10B as described above. Plasmid pSGTYLCV was isolated.

Production of 5-O-mycaminosyl-(4"-O-mycarosyl) erythromycin A

The plasmid pSGTylCV was used to transform SGQ2 and strain SGQ2pSGTylCV was isolated. The cells were grown as described in Materials and Methods and a filtered supernatant from strain SGQ2p(mycaminose)CIII, containing 5-O-mycaminosyl-erythromycin A, was carried out as described for similar experiments previously (Gaisser et al., 2000). The supernatant of the cell culture of strain SGQ2pSGTylCV was analysed using HPLC-MS as described in Materials and Methods and a novel peak with 894 m/z was detected, corresponding to 5-O-mycaminosyl-(4"-O-mycarosyl) erythromycin A.

REFERENCES

The references cited herein are all incorporated by reference.

Caffrey, P. et al., (1992) FEBS 304: 225-228.
Devereux, J. et al., (1984) Nucl Acids Res 12: 387-395.
Fouces, R. et al., (1999) Microbiol 145: 855-868.
Gaisser, S. et al., (1997) Mol Gen Genet 256: 239-251.
Gaisser, S. et al., (2000) Mol Microbiol 36: 391-401.
Gandecha, A. R et al., (1997) Gene 184: 197-203.
Haydock, S. F. et al., (1991) Mol Gen Genet 230: 120-128.
Hernandez, C. et al., (1993) Gene 134: 139-140.
Hessler, P. E. et al., (1997) Appl Microbiol Biotechnol 47: 398-404.
Kaneda, T. et al., (1962) J Biol Chem 237: 322-327.
Katz, E. et al., (1983) J Gen Microbiol 129: 2703-2714.
Pereda, A. et al., (1997) Gene 193: 65-71.
Sambrook, J. et al., (1989) 2nd ed. Cold Spring Harbor Laboratory Press, N.Y.
Sanger, F. et al., (1977) Proc Natl Acad Sci USA 74: 5463-5467.
Staden, R. (1984) Nucl Acids Res 12: 521-528.
Weber, J. M. et al., (1985) J Bacteriol 164: 425-433.
Yamamoto, H. et al., (1986) J Antibiot 34: 1304-1313.
Xue, Y. et al., (1998) Proc Natl Acad Sci USA 95: 12111-12116.
Olano et al., (1998) Mol Gen Genet 259: 299-308.
Rodriguez et al., (1995) FEMS Microbiol. Letters 127: 117-120.
Shah et al., (2000) J Antibiot 53: 502-508.
Spagnoli et al., (1983) J Antibiot 36: 365-375.

The invention claimed is:

1. A hybrid glycosylated product which comprises:
   (a) at least one rhamnose or substituted rhamnose sugar linked to an erythronolide or an erythromycin either at the 3 position or 5 position or at both the 3 and 5 positions of said erythronolide or erythromycin, wherein the hybrid glycosylation product is other than 3-rhamnosyl-5-desosaminyl-erythronolide B, 3-rhamnosyl-6-deoxy-erythromycin B, 3-rhamnosyl-erythronolide B, and 3-rhamnosyl-6-deoxyerythronolide B;
   (b) at least one mycarose or substituted mycarose sugar linked to an erythronolide or an erythromycin either at the 5 position or at both the 3 and 5 positions of said erythronolide or erythromycin;
   (c) at least one mycaminose or substituted mycaminose sugar linked to an erythronolide or an erythromycin either at the 3 position or at both the 3 and 5 positions of said erythronolide or erythromycin;
   or combinations of (a), (b) and (c) sugar substituents on an erythronolide or erythromycin.

2. A compound selected from the group consisting of:
   3-O-(2'-O-methyirhamnosyl)erythronolide B,
   3-O-(2',3'-bis-O-methylrhamnosyl)erythronolide B,
   3-O-(2',3',4'-tris-O-methylrhamnosyl)erythronolide B,
   8a-hydroxy-3-O-mycarosyl-erythronolide B,
   8,8a-epoxy-3-O-mycarosylerythronolide B,
   8,8a-dehydro6-deoxyerythronolide B,
   8-hydroxy-6-deoxyerythronolide B,
   3-O-(2'-O-methyirhamnosyl) erythromycin D,
   3-O-(2',3'-bis-O-rnethylrhamnosyl) erythromycin D,
   3-O-(2',3',4'-tris-O-methylrhamnosyl) erythromycin D,
   5-O-mycaminosyl-4"-O-mycarosyl erythromycin A,
   3-O-rhamnosyl-8,8a-dehydro-6-deoxyerythrolide B,
   3-O-rhamnosyl-8,8a-dihyciroxy-erythronolide B, and
   3,5 di-O-mycarosyl erythronolide B.

* * * * *

UNITED STATES PATENT AND TRADEMARK OFFICE
CERTIFICATE OF CORRECTION

PATENT NO. : 7,482,137 B2 Page 1 of 1
APPLICATION NO. : 11/580263
DATED : January 27, 2009
INVENTOR(S) : Peter F. Leadlay et al.

It is certified that error appears in the above-identified patent and that said Letters Patent is hereby corrected as shown below:

Column 70, line 11 claim 2
  Please delete "methyirhamnosyl" and insert therefor --methylrhamnosyl--.

Column 70, line 15 claim 2
  Please delete "mycarosylerythronolide" and insert therefor --mycarosyl-erythronolide--.

Column 70, line 16 claim 2
  Please delete "dehydro6" and insert therefor --dehydro-6--.

Column 70, line 18 claim 2
  Please delete "methyirhamnosyl" and insert therefor --methylrhamnosyl--.

Column 70, line 19 claim 2
  Please delete "rnethylrhamnosyl" and insert therefor --methylrhamnosyl--.

Column 70, line 22 claim 2
  Please delete "deoxyerythrolide" and insert therefor --deoxyerythronolide--.

Column 70, line 23 claim 2
  Please delete "dihyciroxy" and insert therefor --dihydroxy--.

Signed and Sealed this

Thirtieth Day of June, 2009

JOHN DOLL
*Acting Director of the United States Patent and Trademark Office*